US012653717B1

(12) United States Patent
Horn

(10) Patent No.: US 12,653,717 B1
(45) Date of Patent: Jun. 16, 2026

(54) SYSTEMS AND METHODS FOR STABILIZATION AND ALIGNMENT OF VISION CORRECTION

(71) Applicant: VAZO Therapeutics, LLC, Coronado, CA (US)

(72) Inventor: Gerald Horn, Highland Park, IL (US)

(73) Assignee: VAZO Therapeutics, LLC, Coronado, CA (US)

( * ) Notice: Subject to any disclaimer, the term of this patent is extended or adjusted under 35 U.S.C. 154(b) by 0 days.

(21) Appl. No.: 19/432,421

(22) Filed: Dec. 24, 2025

Related U.S. Application Data

(63) Continuation-in-part of application No. 19/336,123, filed on Sep. 22, 2025.
(Continued)

(51) Int. Cl.
A61F 9/008 (2006.01)

(52) U.S. Cl.
CPC ...................... A61F 9/00804 (2013.01); *A61F 2009/00846* (2013.01); *A61F 2009/00872* (2013.01); *A61F 2009/00897* (2013.01)

(58) Field of Classification Search
CPC ........ A61F 9/00804; A61F 2009/00846; A61F 2009/00872; A61F 2009/00897;
(Continued)

(56) References Cited

U.S. PATENT DOCUMENTS 5,645,550 A    7/1997   Hohla
6,802,837 B2   10/2004   Donitzky
(Continued)

FOREIGN PATENT DOCUMENTS

WO     1990012618 A1   11/1990
WO      9853881 A1   12/1998
(Continued)

OTHER PUBLICATIONS

Zhou, Yuehua et al., "Anterior Segment Optical Coherence Tomography Measurement of LASIK Flaps: Femtosecond Laser vs Microkeratome," Journal of Refractive Surgery, 2011;27(6):408-416, Oct. 29, 2010.
(Continued)

*Primary Examiner* — Carl H Layno
*Assistant Examiner* — Anh-Khoa N Dinh
(74) *Attorney, Agent, or Firm* — FisherBroyles, LLP; John K. Shimmick

(57) ABSTRACT

A patient is provided with a fixation stimulus comprising a plurality of colors, which helps to entrain the fixation of the subject on a fixation target, calm the subject, and provide verification that the patient is appropriately aligned. A processor can be configured to cycle the fixation stimulus through the plurality of colors at regular intervals over a plurality of cycles. A parallax imaging system such as a stereoscopic microscope is used to generate images that combine the left and right views, which can improve alignment and centration. Alignment targets can be provided that allow the use of vernier acuity to determine alignment with the subject. The fixation stimulus and alignment system can be used with many optical therapies, such as contact lenses and laser vision correction.

18 Claims, 22 Drawing Sheets

Related U.S. Application Data

(60) Provisional application No. 63/788,499, filed on Apr. 14, 2025.

(58) Field of Classification Search
CPC .... A61N 1/40; A61N 1/36002; A61N 1/0476;
A61N 1/32; A61N 1/0492; A61N 1/326;
A61N 1/0408; A61N 1/0456; A61N
1/36034; A61N 1/0496; A61N 1/36025;
A61N 1/403; A61N 1/3603; A61N 1/18;
A61N 1/0484; A61N 1/06; A61N 1/205;
A61N 1/327; A61N 1/0529; A61N 1/08;
A61N 1/0428; A61N 1/044
See application file for complete search history.

(56) References Cited

U.S. PATENT DOCUMENTS

| | | | |
|---|---|---|---|
| 8,231,221 | B2 | 7/2012 | Donitzky |
| 8,282,629 | B2 | 10/2012 | Mrochen |
| 10,238,539 | B2 | 3/2019 | Lemonis |
| RE47,550 | E | 8/2019 | Lemonis |
| 2004/0057119 | A1* | 3/2004 | Sagehashi ........... A61F 9/00821 359/618 |
| 2007/0055221 | A1* | 3/2007 | Lubatschowski ....... A61F 9/008 606/5 |
| 2010/0068141 | A1* | 3/2010 | Kaushal .................... A61P 9/10 606/4 |
| 2012/0130357 | A1* | 5/2012 | Triebel ................... A61F 9/009 606/4 |
| 2022/0031503 | A1* | 2/2022 | Dorin ...................... A61F 9/008 |

FOREIGN PATENT DOCUMENTS

| | | | |
|---|---|---|---|
| WO | 1999018868 | A1 | 4/1999 |
| WO | 1999044492 | A1 | 9/1999 |
| WO | 1999062442 | A1 | 12/1999 |
| WO | 2000000097 | A1 | 1/2000 |
| WO | 2000045759 | A1 | 8/2000 |
| WO | 0066022 | A1 | 11/2000 |
| WO | 2000076435 | A1 | 12/2000 |
| WO | 0108547 | A2 | 2/2001 |
| WO | 2001035847 | A1 | 5/2001 |
| WO | 0145606 | A2 | 6/2001 |
| WO | 0150990 | A2 | 7/2001 |
| WO | 2002024093 | A1 | 3/2002 |
| WO | 0238078 | A2 | 5/2002 |
| WO | 0246801 | A3 | 2/2003 |
| WO | 2003090867 | A1 | 11/2003 |
| WO | 2004003468 | A1 | 1/2004 |
| WO | 2004003597 | A2 | 1/2004 |
| WO | 2007095596 | A2 | 8/2007 |
| WO | 2008131909 | A1 | 11/2008 |
| WO | 2009124695 | A1 | 10/2009 |
| WO | 2010000278 | A1 | 1/2010 |
| WO | 2010028663 | A1 | 3/2010 |
| WO | 2010105637 | A1 | 9/2010 |
| WO | 2010108501 | A1 | 9/2010 |
| WO | 2010135685 | A1 | 11/2010 |
| WO | 2011098098 | A1 | 8/2011 |
| WO | 2012041349 | A1 | 4/2012 |
| WO | 2013057307 | A1 | 4/2013 |
| WO | 2017019117 | A1 | 2/2017 |
| WO | 2017083315 | A1 | 5/2017 |
| WO | 2018009898 | A1 | 1/2018 |
| WO | 2023141552 | A1 | 7/2023 |
| WO | 2025006182 | A1 | 1/2025 |

OTHER PUBLICATIONS

Basmak, H., et al., "Measurement of Angle Kappa With Synoptophore and Orbscan II in a Normal Population," Journal of Refractive Surgery, 23:456-460 (May 2007).

Curcio, C.A., et al., "Human Photoreceptor Topography," The Journal of Comparative Neurology, 292:497-523 (1990).

Duncan, R.O., et al., "Cortical Magnification within Human Primary Visual Cortex Correlates with Acuity Thresholds," Neuron, 38:659-671 (May 22, 2003).

Hashemi, H., et al., "Distribution of Angle Kappa Measurements With Orbscan II in a Population-based Survey," Journal of Refractive Surgery, 26(12):966-971 (2010). https://doi.org/10.3928/1081597X-20100114-06.

Horton, J.C., et al., "The Representation of the Visual Field in Human Striate Cortex: A Revision of the Classic Holmes Map," Arch Ophthalmol, 109:816-824 (Jun. 1991).

Howard, I. P., & Rogers, B. J. (1995). Binocular Vision and Stereopsis. Oxford University Press. (736 pages). https://academic.oup.com/book/3243.

Livingstone, M.S., et al., "Psychophysical Evidence for Separate Channels for the Perception of Form, Color, Movement, and Depth," The Journal of Neuroscience 7(11):3416-3468 (Nov. 1987).

Manzanera, Silvestre, et al. "Distribution of Achromatizing Pupil Positions and First Purkinje Reflections in a Normal Population." Investigative Ophthalmology & Visual Science 54.15 (2013): 4281-4281. https://iovs.arvojournals.org/article.aspx?articleid=2149126&utm_source=chatgpt.com.

Martinez-Conde, S., et al., "The Role of Fixational Eye Movements in Visual Perception," Nature Reviews | Neuroscience, 5:229-240 (Mar. 2004).

Schor, C., et al., "Binocular Fusion Limits are Independent of Contrast, Luminance Gradient and Component Phases," Vision Res., 29(7):821-835 (1989). https://doi.org/10.1016/0042-6989(89)90094-1.

Thaler, L., et al., "What is the best fixation target? The effect of target shape on stability of fixational eye movements," Vision Research 76:31-42 (2013).

Uozato, H., et al., "Centering Corneal Surgical Procedures," American Journal of Ophthalmology, 103:264-275 (Mar. 1987). https://www.ajo.com/article/S0002-9394(21)00230-0/abstract.

Westheimer, G., "The Spatial Grain of the Perifoveal Visual Field," Vision Research, 22:157-162 (1982).

Westheimer, G., "Visual Hyperacuity. In Progress in Sensory Physiology," vol. 1, pp. 1-30, Springer (1975).

Williams, David R., "Imaging single cells in the living retina," Vision Research, 51:1379-1396 (2011).

Zhou, Y., et al., "Anterior Segment Optical Coherence Tomography Measurement of LASIK Flaps: Femtosecond Laser vs Microkeratome," Journal of Refractive Surgery, 27(6):408-416 (2010).

Wavelight EX500 Excimer Laser System, Alcon Inc., printed Dec. 13, 2025, 16 pages.

Wavelight EX500 Excimer Laser User Manual, Alcon Inc., Rev. 09, Jun. 17, 2019, Item No. 6672 2001, 346 pages.

Zeiss MEL 90, Advanced excimer laser technology, printed Dec. 13, 2025, 21 pages.

Press Release Zeiss MEL 90 excimer laser receives US FDA approval; completes Corneal Refractive Workflow, printed Dec. 13, 2025, 11 pages.

Sheetal Brar MD, Smile for myopia and myopic astigmatism—Increasing procedural ease and efficiency with the Visumax 800 femtosecond laser, 1 page.

Bausch + Lomb Receives FDA Approval for Teneo Excimer Laser Platform for Myopia and Myopic Astigmatism LASIK Vision Correction Surgery, Jan. 8, 2024, 7 pages.

Brandenburg, Traeson M., et al. "Comparison of Zeiss MEL90 and Alcon WaveLight EX500 Excimer Lasers in FDA Premarket Approval Trials for the Treatment of Myopia, Hyperopia, and Mixed Astigmatism." Journal of Clinical Medicine 14.15 (2025): 5403.

Summary of Safety and Effectiveness Data (SSED), Ophthalmic Excimer Laser System, Alcon Labs, Inc., PMA P020050/S023, 36 pages.

WaveLight EX500 Addendum Procedure Manual Innoveyes Treatments, Alcon, Rev. 00g, Mar. 4, 2025, Item No. 6675 2029, 54 pages.

MEL 90 Professional Use Information, Laser-Assisted In Situ Keratomileusis (LASIK) for the correction of myopia and hyperopia

(56) References Cited

OTHER PUBLICATIONS with or without astigmatism and mixed astigmatism, 000000-2179-684-ProfUseInf-MEL 90 LASIK-en-US-211124, 226 pages.

Schwind Amaris 1050RS, printed Dec. 13, 2025, 6 pages.

Schwind eye-tech-solutions—specialist for eyesight surgery, printed Dec. 13, 2025, 6 pages.

Bausch + Lomb Technolas Teneo 317 Model 2 Excimer Laser, printed Dec. 13, 2025, 2 pages.

Bausch + Lomb Teneo Excimer Laser Platform, printed Dec. 13, 2025, 15 pages.

Bausch + Lomb Teneo 317 Model 2M2—the refractive [R]evolution, printed Dec. 13, 2025, 4 pages.

Arbelaez, Maria Clara, and Samuel Arba Mosquera. "The Schwind Amaris total-tech laser as an all-rounder in refractive surgery." Middle East African Journal of Ophthalmology 16.1 (2009): 46-53.

Harris, William F. "Chief nodal axes of a heterocentric astigmatic eye and the Thibos-Bradley achromatic axis." Vision research 73 (2012): 40-45.

Hibbs, John S. "Contracting With Managed Health Care Plans in the Present Health Care Environment." American Journal of Ophthalmology. vol. 103, Issue 3. Mar. 1987, 7 pages.

* cited by examiner

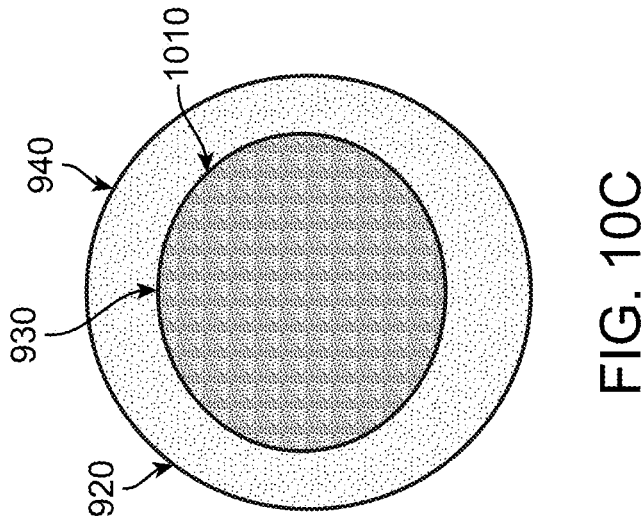
FIG. 10C
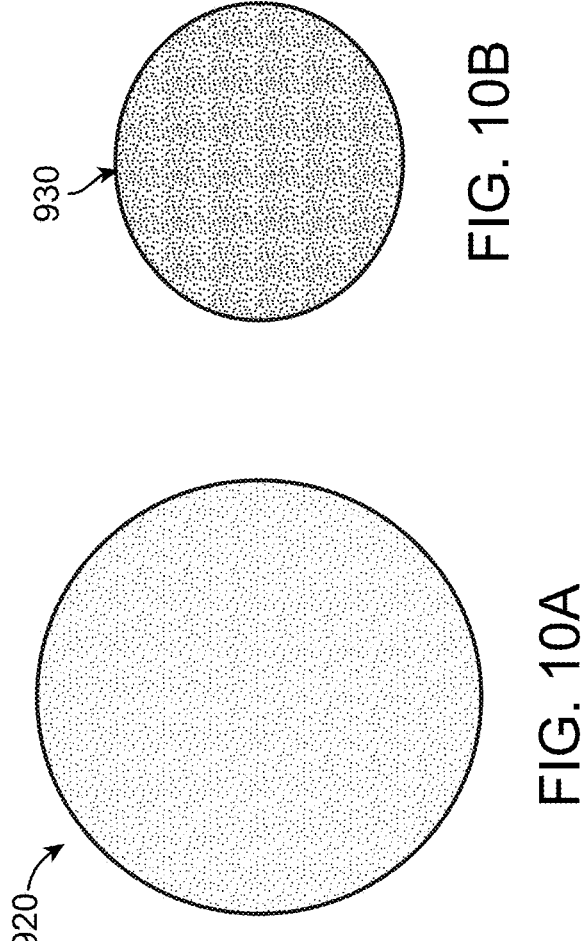
FIG. 10B
FIG. 10A

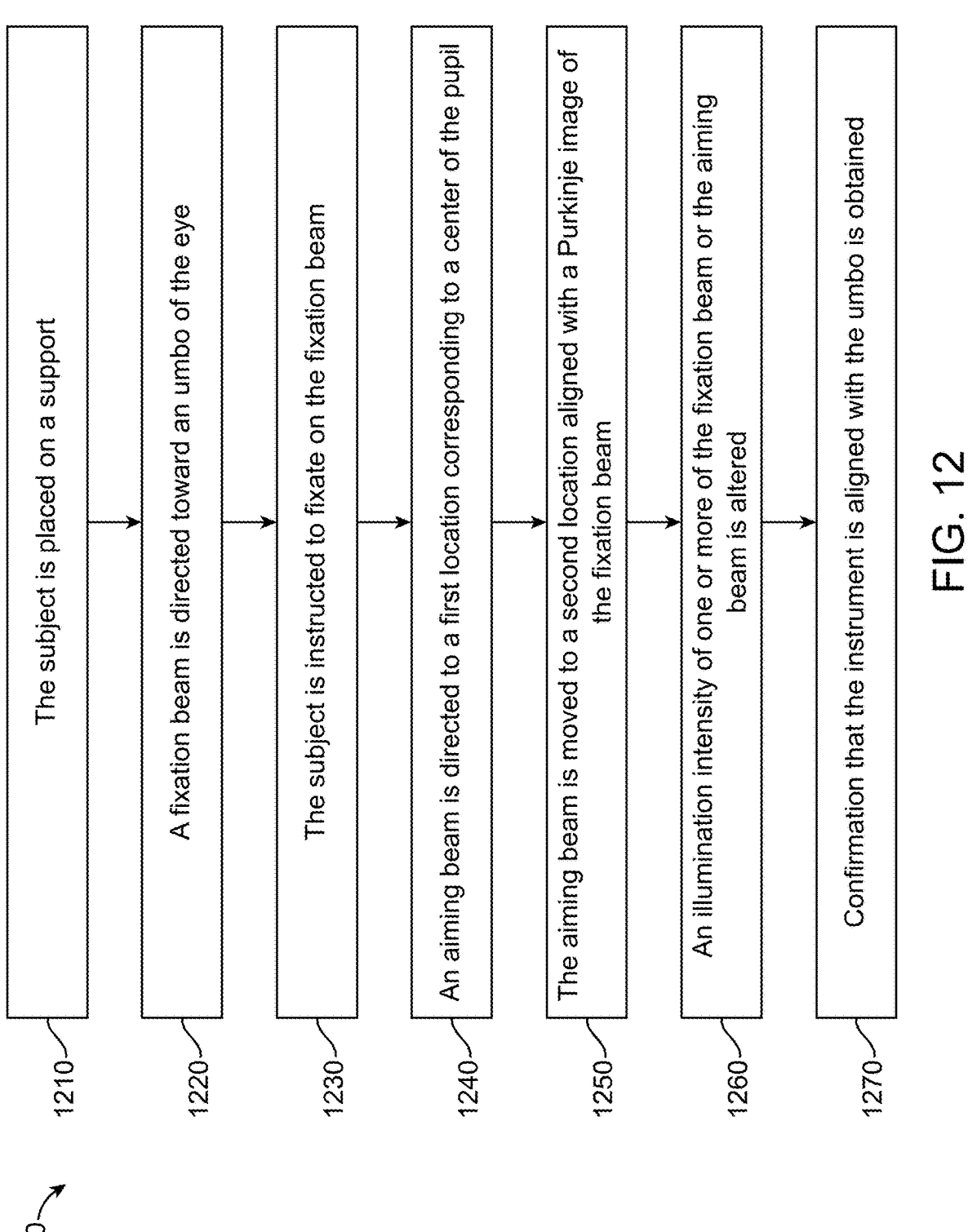

1210 — The subject is placed on a support

1220 — A fixation beam is directed toward an umbo of the eye

1230 — The subject is instructed to fixate on the fixation beam

1240 — An aiming beam is directed to a first location corresponding to a center of the pupil 1250 — The aiming beam is moved to a second location aligned with a Purkinje image of the fixation beam 1260 — An illumination intensity of one or more of the fixation beam or the aiming beam is altered 1270 — Confirmation that the instrument is aligned with the umbo is obtained

1300

1310 — Optical switch selectively blocks transmission of one of the parallax images 1320 — A fixation beam is directed toward an umbo of the eye 1330 — A processor selectively provides first parallax image or the second parallax image 1340 — A combined image is generated from the first parallax image and the second parallax image

1400

1410 — A fixation light source is cycled to emit a fixation light

1420 — Images of the eye are captured at each of a plurality of cycles of the fixation light source 1430 — A location of a Purkinje image of the fixation light source is determined 1440 — Fixation stability is confirmed 1450 — Neuro-visual lock-in of the subject is verified

1500

1510 A processor is coupled to system components

1520 An intensity of the fixation beam or the aiming beam is adjusted

1530 Toggling between the first parallax image and the second parallax image

1540 A combined image is generated

1550 Alignment data is output

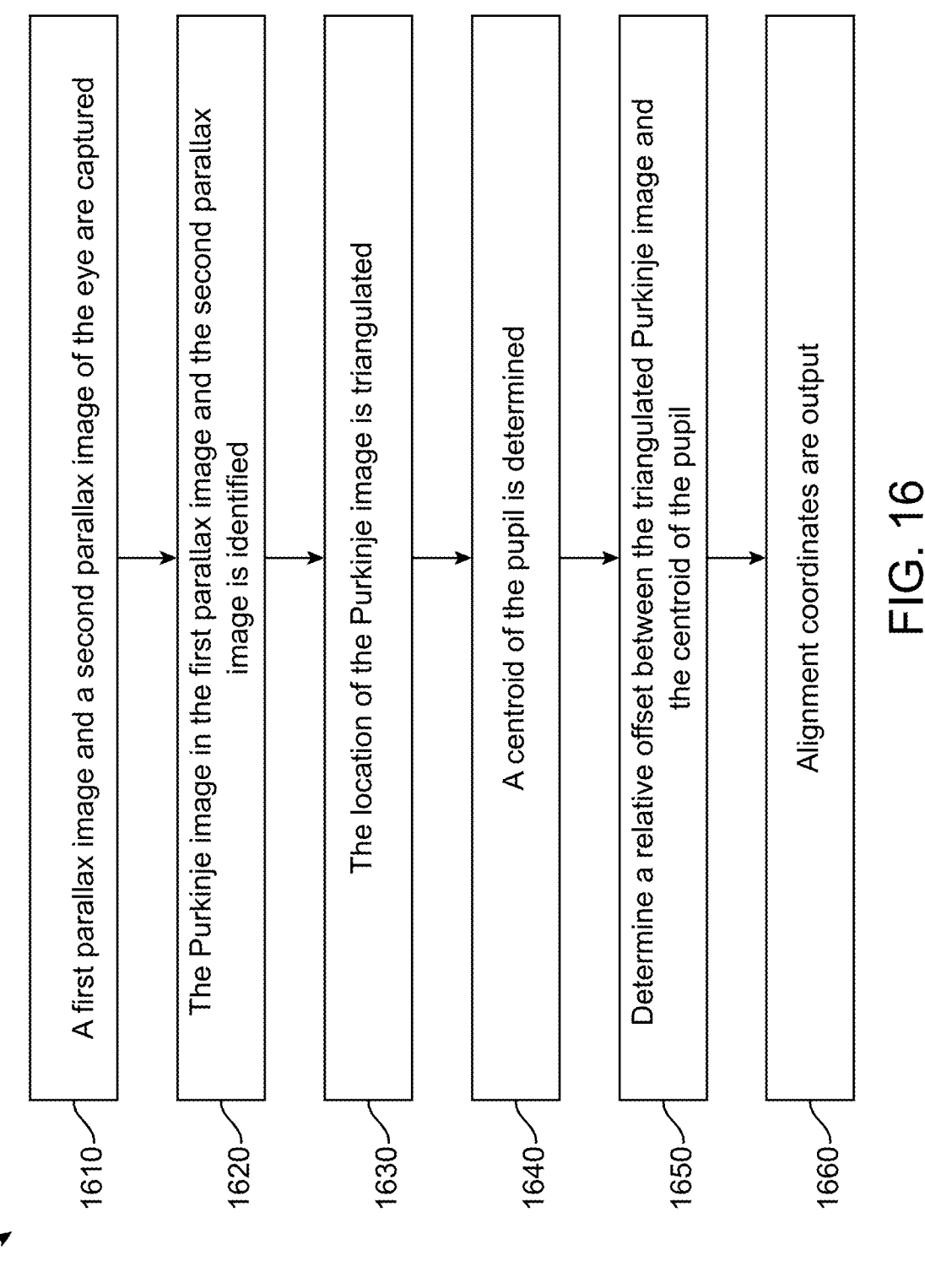

1610 — A first parallax image and a second parallax image of the eye are captured 1620 — The Purkinje image in the first parallax image and the second parallax image is identified 1630 — The location of the Purkinje image is triangulated 1640 — A centroid of the pupil is determined 1650 — Determine a relative offset between the triangulated Purkinje image and the centroid of the pupil 1660 — Alignment coordinates are output

Parameters of each camera are calibrated

A fixation target is detected at sub-pixel resolution

A three-dimensional point corresponding to the fixation target is triangulated

A symmetry constraint of the binocular system is enforced

Temporal fusion of the fixation point is performed

1800

1810 — A binocular microscope is provided

1820 — Fixation stability is verified

1830 — A left parallax view is presented

1840 — A right parallax view is presented

1850 — A paired mean offset is computed

1860 — Additional paired offset measurements are acquired by repeating steps 1830 through 1850

1870 — A lock is achieved

2000

| Provide fixation stimulus | — 2010 |

| Evaluate fixation | — 2020 |

| Align eye with laser | — 2030 |

| Initiate laser treatment | — 2050 |

| Evaluate firing gate | — 2060 |

| Utilize predictor | — 2070 |

| Adjust beam | — 2075 |

| Relock on umbo surrogate | — 2080 |

| Resume treatment | — 2090 |

| Complete treatment | — 2095 |

SYSTEMS AND METHODS FOR STABILIZATION AND ALIGNMENT OF VISION CORRECTION

RELATED APPLICATIONS

The present application claims priority to U.S. application Ser. No. 19/336,123, filed Sep. 22, 2025, U.S. Provisional Application No. 63/788,499, filed Apr. 14, 2025, entitled "NOVEL DEVICES, SYSTEMS AND METHODS: UMBO VISION", the entire disclosures of which are incorporated herein by reference.

BACKGROUND

The retina of the human eye is critical for vision. The umbo of the fovea has the highest density of cones of the retina and has a potential for visual acuity greater than other parts of the retina. For example, the fovea of a human subject may have a cone density of approximately 150,000 to 300,000 cones per square millimeter (mm²), whereas the umbo may have a greater density of cones, approximately 325,000 to 350,000 cones per mm². Although humans have the potential to see with 20/08 vision with the umbo, this high level of visual acuity can be difficult to achieve in at least some instances. Work in relation to the present disclosure suggests that the prior approaches to treating vision have less than ideally addressed the potential vision of the umbo.

Work in relation to the present disclosure suggests that slight decentrations of optical treatments can result in an amplified effect of the decentration at the umbo in at least some instances. The distance from the cornea to the front nodal point of the eye is approximately one third of the distance from the back nodal point to the retina of the eye, which can result in small decentrations of a surgical procedure near the cornea having approximately a threefold increase at the umbo, in at least some instances.

Prior approaches to aligning instruments to eyes of subjects such as patients can be less than ideal in at least some instances. The eye is prone to movement and may undergo saccades. Also, continuous fixation on a target can be somewhat tiring for the subject and the gaze may tend to wander in at least some instances. With some surgical procedures, such as Laser Assisted in situ Keratomileusis (LASIK), the patient may be nervous and have difficulty relaxing, which can make fixation difficult in at least some instances. Although patients may be asked to fixate on a blinking fixation light, the resulting fixation can be less than ideal, and the patient's eye fixation may deviate from the fixation light in at least some instances. The prior approaches with a monochromatic blinking fixation light may only illuminate the patient's retina for a portion of the time that the patient is trying to fixate, e.g. half of the time, which may result in eye movement when the light blinks off and is not present, in at least some instances. Although the fixation light may blink on and off at a frequency of 3 to 6 Hertz (Hz), this is much slower than eye movements such as saccades.

Work in relation to the present disclosure also suggests that the prior approach to fixation may less than ideally engage fixation of the foveola and the umbo of the subject. Although humans have the ability to perceive changes in alignment of objects with vernier acuity much more accurately than with normal vision, the prior approaches may have less than ideally presented a fixation stimulus to a subject in a manner that takes advantage of vernier acuity, in at least some instances. For example, a blinking monochromatic fixation light may lack visual information that could help the patient fixate on the fixation target.

Although many surgical microscopes such as operating microscopes are stereoscopic to allow the surgeon to view tissue with depth perception, work in relation to the present disclosure suggests that prior approaches to fixation with stereoscopic microscopes can be less than ideal in at least some instances. For example, when a surgery is centered on the first Purkinje image of the eye, stereo microscopes may not provide appropriate markers. The location of the first Purkinje image may be offset depending upon which eye of the surgeon is used to align the Purkinje image with the treatment system, which may result in less than ideal centration of the procedure in at least some instances. Also, the dominant eye of the surgeon may determine which eye is used to align the Purkinje image with ablation pattern, for example.

Prior approaches to aligning surgical procedures with an eye may be prone to errors related to alignment of a target with the surgical system. For example some surgical procedures rely on a reticle to align the ablation pattern with an ocular target such as a pupil or a Purkinje image, in some instances. Although somewhat effective, this approach can be somewhat limited in terms of how accurately a reticle can be aligned with an ocular structure in at least some instances. Work in relation to the present disclosure suggests that at least some of the prior approaches to aligning systems with eyes may less than ideally utilize the human neural visual cortical processing capabilities of a human operator such as a surgeon.

Work in relation to the present disclosure suggests that the prior approaches may be less than ideally suited for aligning lasers with tissue structures located at different depths of the eye. The eye has tissue structures that are located at different depths from the operating microscope, such as the cornea, the Purkinje image and the pupil, and at least one of these images may be out of focus. With microscopes such as surgical microscopes, the focus of the microscope can be set on the cornea, resulting in other tissue structure such as the Purkinje image and the iris being out of focus. With stereo microscopes, these tissue structures may shift depending on whether the left ocular or the right ocular is used by the surgeon.

In humans, the visual axis is typically offset from the optical axis of the eye. This offset may be referred to as angle Kappa. The offset of the human visual axis from the optical axis can present situations with refractive surgeries, such as LASIK, that the prior art has less than ideally addressed in at least some instances. This offset can result in a reflex of a fixation beam (first Purkinje image) being offset from the entrance pupil of the eye, and the surgeon is faced with a decision as to whether to center the refractive treatment on the entrance pupil or the reflex.

In light of the foregoing, it would be desirable to have improved methods and apparatus to align an eye with an instrument that overcome at least some of the aforementioned limitations of the prior approaches.

SUMMARY

Embodiments of the present disclosure provide improved methods and apparatus to align an instrument with an eye. In some embodiments, the patient is provided with a fixation stimulus comprising a plurality of colors, which may help to entrain the fixation of the subject on the target, calm the subject, and provide verification that the patient is appropriately aligned. In some embodiments, a parallax imaging system such as a stereoscopic microscope is used to generate images that combine the left and right views, which can improve alignment and centration. In some embodiments, alignment targets are provided that allow the use of vernier acuity to determine alignment with the subject, which may have much higher resolution than normal vision.

While the fixation stimulus can be provided in many ways, in some embodiments, the fixation stimulus comprises a plurality of colors, each of which is presented sequentially at repeated time intervals, which may help the subject entrain fixation on the stimulus such as a fixation target. The colors can be presented sequentially so as to appear at the same location to the subject. This approach can provide a fixation stimulus in which the retina is illuminated for a longer time with each cycle than a blinking monochromatic fixation stimulus. In some embodiments, the fixation stimulus comprises a first color for a first duration and a second color for a second duration of a cycle, which allows the retina to be illuminated with nearly continuous illumination to improve fixation and decrease eye movements. In some embodiments, the first color and the second color are presented to the subject with a combined duty cycle of over 80% or more. When the color changes, the subject can be prompted to verify that the perceived light beam does not change location, which can be helpful to confirm proper alignment. In some embodiments, a processor is configured to change an intensity of the first light beam and the second light beam, so as to cycle through a combination of colors at regular predefined intervals, which can help to calm the subject and entrain the subject's fixation on the fixation target.

In some embodiments the fixation stimulus provided to the subject comprises a first light beam such as an aiming beam aligned with a second light beam such as a fixation light beam. In some embodiments, the first light beam such as the alignment light beam and the second light beam such as the fixation light beam comprise different colors, so that the subject perceives a change in color when one of the beams changes intensity. In some embodiments, the first light beam such as the aiming beam and the second light beam such as the fixation beam are aligned with each other so as to overlap on the cornea and the retina of the subject at substantially the same location.

In some embodiments a parallax imaging system is used to generate a combined image of the eye. The parallax imaging system can be configured to generate a left eye view and a right eye view, which can be combined to generate a combined image. Alternatively or in combination, optical switches can be used to alternate the left eye view and the right eye view, to encourage a user such as a surgeon to rely on both eyes when aligning the eye, and decrease the effect of ocular dominance of the user on alignment with the eye. In some embodiments, the combined image is generated from a first image from a first optical path such as a right optical path and a second image from a second optical path such as a left optical path. The combined image can be generated in many ways and may comprise a first Purkinje image of the fixation beam captured from the first optical path and a second Purkinje image from the fixation beam captured from a second optical path, in which the first Purkinje image is separated from the second Purkinje image in the combined image. Alternatively or in combination, the combined image may comprise a combined Purkinje image placed at a location corresponding to an average location of the Purkinje image from a first captured image from the first optical path and a second image captured from the second optical path. In some embodiments, light from a beam such as an aiming beam is focused to a spot on the cornea is present in the first image and the second image, which are used to generate the combined image. In some embodiments, a stereo microscope such as an operating microscope is set to focus on the cornea, such that the focused spot is located at substantially the same location in the first parallax image and the second parallax image. While the parallax image data can be used in many ways, in some embodiments, the first image from the first optical path and the second image from the second optical path are used to triangulate the location of one or more of a location of a spot focused on the cornea, a location of a Purkinje image, or a location of a center of a pupil.

In some embodiments, the left and right views of the Purkinje image and a focused spot such as a focused spot of an aiming beam are arranged to allow the user to use vernier acuity to align the system with the eye. In some embodiments, the Purkinje image from the first optical path and the Purkinje image from the second optical path appear offset from each other. In some embodiments the aiming beam is moved into alignment by the user so as to place the aiming beam between the right view of the Purkinje image and the left view of the Purkinje image with vernier acuity, which can improve alignment. In some embodiments, in an aligned configuration the aiming beam is placed substantially equidistant and colinear between the left and right Purkinje image, which can provide substantially improved alignment.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 10A shows a first light pulse, in accordance with some embodiments;

FIG. 10B shows a second light pulse, in accordance with some embodiments;

FIG. 10C shows a perceived combined light pulse, in accordance with some embodiments;

FIG. 12 shows a method of aligning an eye of a subject with an instrument, in accordance with some embodiments;

FIG. 16 shows a triangulation method, in accordance with some embodiments;

DETAILED DESCRIPTION

Figure 1A:
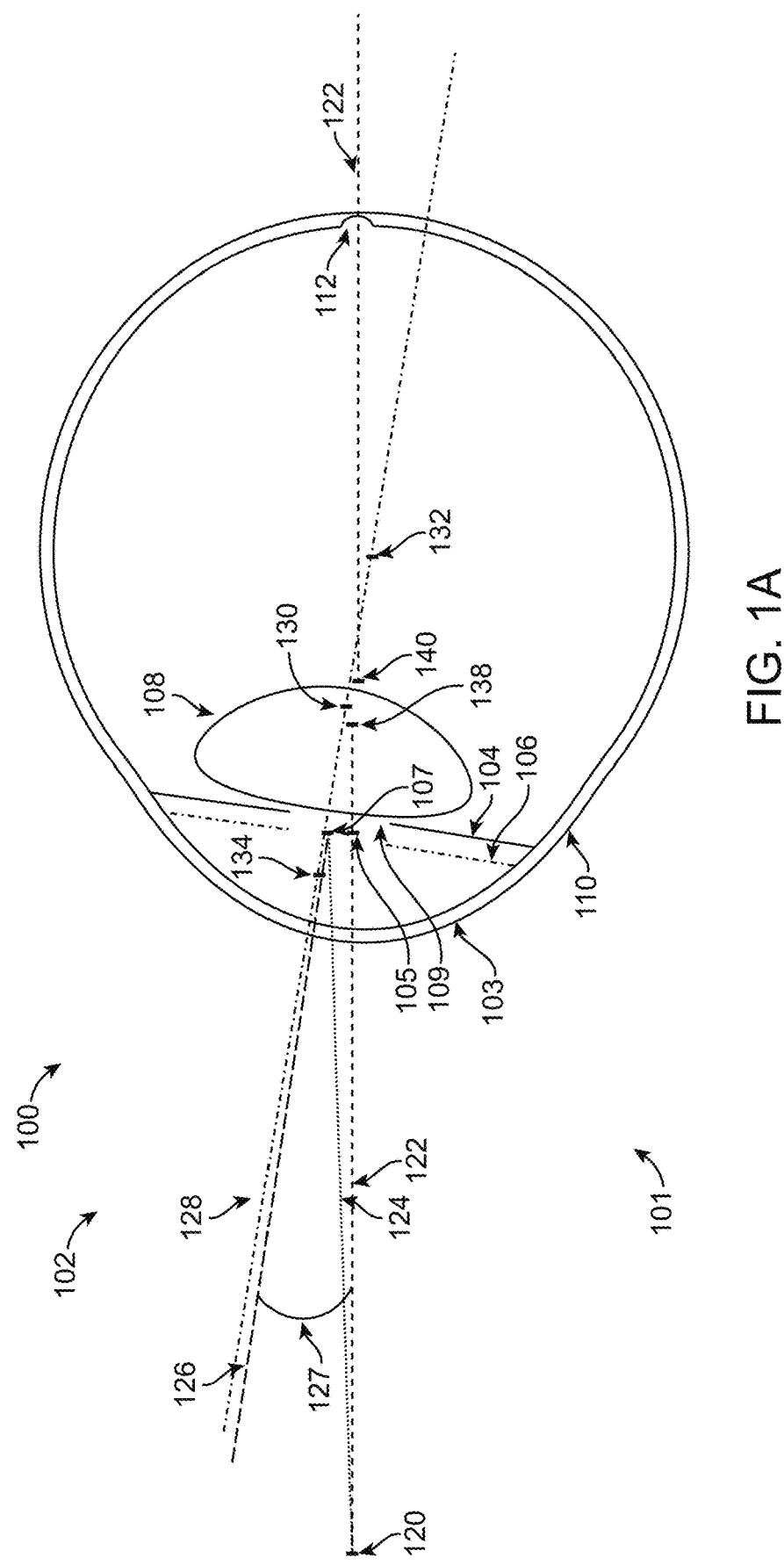
FIG. 1A shows an eye, suitable for incorporation in accordance with some embodiments of the present disclosure.

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

In some embodiments, the system is configured to align an optical treatment or therapy with one or more of a foveola or an umbo of the eye. In some embodiments, an alignment precision is confirmed to be within one or more of ±100 microns, +50 microns, +20 microns or ±10 microns and optionally confirmed with an input from a user.

While the presently disclosed systems and methods can be configured to align with any ocular structure, in some embodiments the system is configured to align with a first Purkinje image of the eye, as a surrogate for alignment with an umbo of the eye. In some embodiments, the visual axis extends to from a nodal point of the eye to the umbo, for example.

Embodiments of the present disclosure provide improved visual performance, which may be related at least in part to improved centration tolerancing that takes into account the cone photo receptor density and the increased effect of decentration at the umbo of the eye as compared with the cornea of the eye. In some embodiments, the error at the umbo can be approximately 3.1 times the error at the cornea. In accordance with some embodiments, from the center of the fovea to the edge of the foveal avascular zone (FAZ), there is roughly a twofold to fourfold drop in cone photoreceptor density over a region with an approximate radius of three hundred micrometers at the retina. This corresponds to only about one hundred micrometers at the corneal plane due to post-nodal point expansion, which is approximately seventeen millimeters in a model eye having an axial length of twenty-four millimeters, based on standard optical calculations, in accordance with some embodiments. Under scotopic conditions, corresponding to night-time pupil sizes, these deviations may in some cases affect not only factors that sharpen maximum visual acuity potential, but may also substantially reduce low-contrast visual acuity and overall scotopic vision quality. The improved alignment directed to the umbo of the eye as described herein may substantially increase low-contrast visual acuity and overall scotopic vision quality as well vision at other amounts of illumination such as mesopic and photopic.

The alignment coordinates can be configured to be transmitted to a treatment device or optical platform. In some embodiments, the output umbo location data is configured to be provided to one or more of an optical system, a targeting system, a ranging system, a scopes, a weapon sighting system, a magnified sighting system, binoculars, binocular sighting systems, a binocular targeting system, a lens, a microscope, a stereo microscope, a radiation therapy device, a robotic surgery system, a laser vision correction (LVC) system, a femtosecond laser system, an excimer laser system, a lens manufacturing system, a lens, an intraocular lens (IOL) manufacturing system, an intraocular lens, an intraocular lens planning system, a contact lens manufacturing system, a contact lens planning system, a contact lens (CL), a scleral contact lens, a rigid gas permeable (RGP) lens, a soft contact CL, a hybrid RGP/soft CL, a hydrogel CL, a stabilized CL, an intraocular lenses (IOL), an intracorneal lens (ICL), a spectacle manufacturing system, a spectacle, a visual aid, or a visual appliance, in order to provide an umbo-centered optical treatment, for example.

In some embodiments, a posture-dependent compensation module configured to measure and correct for translational shift in alignment center and pupil centroid between diagnostic (upright) and treatment (supine) positions. In some embodiments, the alignment data is stored in association with the subject's pupil diameter and lighting condition during each of a plurality of recording cycles. In some embodiments, the processor is configured to output data comprising a plurality of pupil diameters at a plurality of illumination intensities, and a plurality of alignment marker locations referenced to a pupil center at each of the plurality of illumination intensities.

In some embodiments, a display comprises one or more of a computer display, a heads up display, an augmented reality display, virtual reality display, a stand-alone display, or a touch screen display configured to receive a user input, for example. The data can be presented on the display of a user interface, for example.

The presently disclosed systems and methods can be particularly well suited for determining the axes of any eccentric imaging system, in which the line of site is displaced from optical axis. The human eye is a non-limiting example of such an imaging system.

Although reference is made to the eye, the presently disclosed systems and methods are well suited for use with many optical applications, targeting systems such as ranging systems and scopes, weapon sighting, magnified sighting, binoculars, binocular sighting systems, binocular targeting systems, lenses, microscopes, stereo microscopes, radiation therapy, or robotic surgery. The presently disclosed systems and methods are also suitable for use with spectacle manufacturing, visual aids, ophthalmic instruments, microscopes, slit lamps, operating microscopes, stereoscopic microscopes, contact lenses (CLs), scleral contact lenses, rigid gas permeable (RGP) lenses, hybrid RGP lenses with a soft skirt, hydrogel contact lenses, stabilized contact lenses, intraocular lenses (IOLs), intracorneal lenses (ICLs), optical treatments, alignment of surgical procedures, laser surgical procedures, laser vision correction (LVC), a femtosecond laser system, an excimer laser system, Small Incision Lenticule Extraction (SMILE), Femtosecond Lenticule Extraction (FLEx), Smooth Incision Lenticule Keratomileusis (SILK), penetrating keratoplasty (PKP), and Laser Assisted in situ Keratomileusis (LASIK), for example.

The presently disclosed methods and apparatus are well suited for combination with commercially available systems and methods, such as commercially available topography systems, auto refractors, fundus imaging systems, systems for Wavefront-guided LASIK and Topography-guided LASIK. For example, the presently disclosed systems and methods are well suited for commercially available diagnostic and LASIK systems, such as the Visumax and MEL systems available for Zeiss, the Zyoptix system available from Bausch and Lomb, the Star S-series excimer lasers available from Johnson and Jonshon, the Wavelight 500 EX excimer laser system, the Vario Diagnostic Device, the Alcon Wavelight Vario Topolyzer, and the Alcon Wavelight Refractive Suite, commercially available from Alcon.

The presently disclosed systems and methods can be combined features of any of the aforementioned systems, such as a pair of diode aiming beams used to set the distance of the eye from the system.

The presently disclosed systems and methods can be configured in many ways. In some embodiments, the alignment system comprises a standalone system.

Alternatively, the alignment system may be incorporated into a treatment system, for example.

In some embodiments, the presently disclosed systems and methods may rely on the neural visual cortex of the patient or the system operator to provide improved alignment. Work in relation to the present disclosure suggests that the human eye can detect small errors in the symmetry structure of an object or an image, and that small defects in the symmetry of targets such as vernier acuity targets can be detected by humans, for example defects in symmetry on the order of seconds of arc into the human eye. The symmetry structure can be provided in many ways and may comprise one or more of a chrominance structure or a luminance structure. For example, the symmetry structure may comprise a monochromatic pattern with symmetry structure, such as 3 dots in a row. Alternatively, the symmetry structure may comprises different colors, such as different colors arranged in a spatial pattern or different colors provided at different times and combinations thereof, in order to stimulate the visual neural cortex pathways. For example an inner dot may comprise a first color such as red and a pair of outer dots may comprise a second color such as green, for example. In some embodiments, a target alternates in color at different times, so that subtle differences in symmetry structure such as overlap can be detected. Also, because light scatter can be different for different wavelengths and some surgical procedures may result in one or more roughened surfaces of the eye, e.g. the cornea, work in relation to the present disclosure suggests that providing different stimulus colors may be helpful in providing a time varying fixation stimulus with symmetry structure for the patient to fixate on.

The symmetrical images that are used for alignment with the neural visual cortical pathway may comprise any suitable images as disclosed herein, a row of three dots, symmetry of a first dot overlaid over a second dot, or edge kissing of dots, for example aligned with a reference as described herein. In some embodiments, the symmetrical targets provided to the patient may comprise a visual stimulus with at least two colors, in which the subject is asked to confirm alignment of the stimulus, for example when the stimulus changes colors. Also, work in relation to the present disclosure suggests that a stimulus that changes colors may be helpful in stimulating the neural visual pathways of the subject, which can allow the subject to provide feedback in assisting the physician to align the subject with an instrument in order to define a treatment axis. Also, the stimulus changing color may reduce eye movement such as saccadic eye movement.

In some embodiments, the image with symmetry structure may be provided to the user of a system such as a surgeon or technician. In some embodiments, the system is configured to provide visual alignment targets to the user, such as a row of three dots, symmetry of a first dot overlaid over a second dot, or edge kissing of dots, for example aligned with a reference as described herein. In some embodiments, these targets are configured to move in response to user inputs, such as images within a microscope or on a combined image of a display, and a user interface is configured to allow a user to adjust alignment to improve the symmetry structure of the images. In some embodiments, the user interface is configured for the user to center a first target on a second target, for example so that a first target of smaller diameter is centered on a second target of larger diameter. Alternatively or in combination, the system may be configured for a user to adjust the symmetry of three dots along a line, so that the dots are evenly spaced, for example. In some embodiments, the user interface is configured to allow the user to align the system in response to two outer dots overlapping with an inner dot, such that the overlap of the outer dots with the inner dot is substantially the same, for example with an edge kiss configuration as described herein.

In some embodiments, the presently disclosed systems and methods are configured for a human to align an object such as the eye to the instrument with hyperacuity such as vernier acuity. In some embodiments, the aiming beam can be aligned with the Purkinje image with a repeatability substantially less than one minute of arc, and in some embodiments to within about 10 seconds of arc. Vernier acuity can detect differences in the alignment of targets with a resolution on the order of a seconds of arc, e.g. approximately 2 to 5 seconds of arc, whereas normal vision is limited to approximately one minute of arc. Work in relation to the present disclosure suggest that embodiments of the presently disclosed systems and methods can provide repeatable alignment to the eye with a repeatability on the order of 100 micrometers (microns) or better, e.g. within a range from 10 to 50 micron repeatability or better.

The cone density of the human foveola may be within a range from 150,00 to 300,000 cones per mm$^2$, and the human umbo may with within a range from about 325,000 to 350,000 cones/mm$^2$. The presently disclosed systems and methods can provide alignment of an eye to an instrument with vernier acuity which substantially exceeds the limits of normal vision based on a Nyquist sampling frequency of approximately 20/08, in accordance with some embodiments. In some embodiments, the alignment targets such as the aiming beam and views of the Purkinje image are spaced apart to be imaged by the user's eye onto the foveola and correspond to an angular subtense of approximately 1.2 degrees (72 minutes of arc). Alternatively or in combination, the alignment targets such as the aiming beam and Purkinje images are spaced apart spatially to be imaged by the user's eye onto the umbo and correspond to an angular subtense of approximately 30 minutes of arc.

In some embodiments, the alternating color of the plurality of pulses presented to the eye of the subject can generate different patterns on the retina of the subject and provide retinal cues to engage visual neural system associated with vernier acuity to allow the subject to more accurately perceive the target, e.g. to entrain fixation on the target. In some embodiments a first pulse of a first color is overlapped with a second pulse with a second color to provide chrominance and luminance cues to the subject, for example similarly to alignment tasks associated with vernier acuity.

The angular subtense of the alignment targets can be configured in many ways by one of ordinary skill in the art, in accordance with embodiments of the present disclosure. In some embodiments, the angular subtense of the arrangement of targets corresponds to a distance from the targets to an entrance pupil of an imaging lens, as will be understood by one of ordinary skill in the art of optics. Alternatively or in combination, the angular subtense may correspond to size of the targets when imaged and provided to a user, for example imaged in an ocular of a microscope or provided on a computer display. In some embodiments, the targets can be provided on a display, and the size of the targets on the display can be related to a normal distance from a display, such as approximately one to three feet from a computer display.

FIG. 1A shows an eye 100 such as a human eye, suitable for incorporation in accordance with embodiments of the present disclosure. The eye 100 has a nasal side 101 and a temporal side 102. The eye has a cornea 103, an iris 104, a pupil 109, a lens 108, a sclera 110 and a fovea 112. The iris 104 has an inner edge that extends around and defines the pupil 109. When viewed externally, the iris 104 appears as a virtual image 106 of the iris 104. At the center of the virtual image 106 of the pupil 109 lies the entrance pupil 107, which can be viewed externally, for example with a camera or a microscope such as an operating microscope or a slit lamp.

In some embodiments, the eye 100 fixates on a fixation point 120. Light from the fixation point 120 reflects off the anterior surface of the cornea and generates a first Purkinje image 105. The first Purkinje image 105 is a virtual image of the light source, the location of which is related to the radius of curvature R of the cornea. In general, the Purkinje image is located at a distance of approximately R/2 below the surface of the cornea, although the exact location may vary depending on the distance of the fixation point 120 from the eye.

In some embodiments, additional axes of the eye may include the visual axis 122, the line of sight 124, the pupillary axis 126, an angle Kappa 127, and the optical axis 128, for example. The eye has a visual axis 122, which connects the fixation point 120 with the front nodal point 138, and also extends from a back nodal point 140 to the umbo located within the foveola of the eye. The line of sight 124 extends from the fixation point 120 to the center of the entrance pupil. The eye also has a pupillary axis 126 an optical axis 128. An angle Kappa 127 subtends between the visual axis 122 and the pupillary axis 126. The pupillary axis 126 corresponds to a line perpendicular to the anterior corneal surface that passes through the center of the entrance pupil.

The optical axis 128 of the eye can be defined with respect to the centers of curvature of the eye. In some embodiments, the cornea comprises a front surface center of curvature 130. The lens has a front surface center of curvature 132, and a back surface center of curvature 134. The optical axis may extend through each of these axes, for example.

The presently disclosed systems and methods are well suited for determining a location on a refractive surface of an eye, such as a cornea or a lens, which corresponds to a location of an umbo of the eye. For example, the location on the cornea or the lens may correspond to an axis extending from the surface of the cornea or the lens to the umbo. In some embodiments, the location of the cornea or the lens of the eye corresponding to the location of an umbo of the eye is determined, and the optical therapy is placed at the location of the cornea or the lens of the eye that corresponds to centration of the therapy on the umbo. In some embodiments, a location of a center of treatment on the cornea has been chosen to place a central effect of the treatment on the umbo of the eye, for example.

The location on the cornea or lens that corresponds to a centered treatment on the umbo can be determined in many ways, for example with one or more of ray tracing of the axes and nodes of the eye, optical coherence tomography images of the eye, topography of the eye, wavefront measurements of the eye, Scheimpflug images of the eye, Purkinje images of the eye, retinal images, the achromatic axis of the eye, or subjective feedback from the subject, for example.

In some embodiments, the optical therapy comprises an optical surface profile configured to correct an optical error or aberration of the eye, such as a refractive error or a wavefront error of the eye. The optical surface profile may comprise an optical surface of a therapy as described herein, such an optical surface profile of an ablated cornea, an optical surface profile of a lenticle, an optical surface profile of an anterior surface of a contact lens, or an optical surface profile of an intraocular lens. In some embodiments, the optical surface profile of the therapy comprises a central location that does not deviate a ray of light, and the central location of the optical surface profile is aligned with the corresponding location of the cornea or lens, such that the therapy is centered on the cornea or the lens with respect to the umbo.

Figures 1B, 1C:
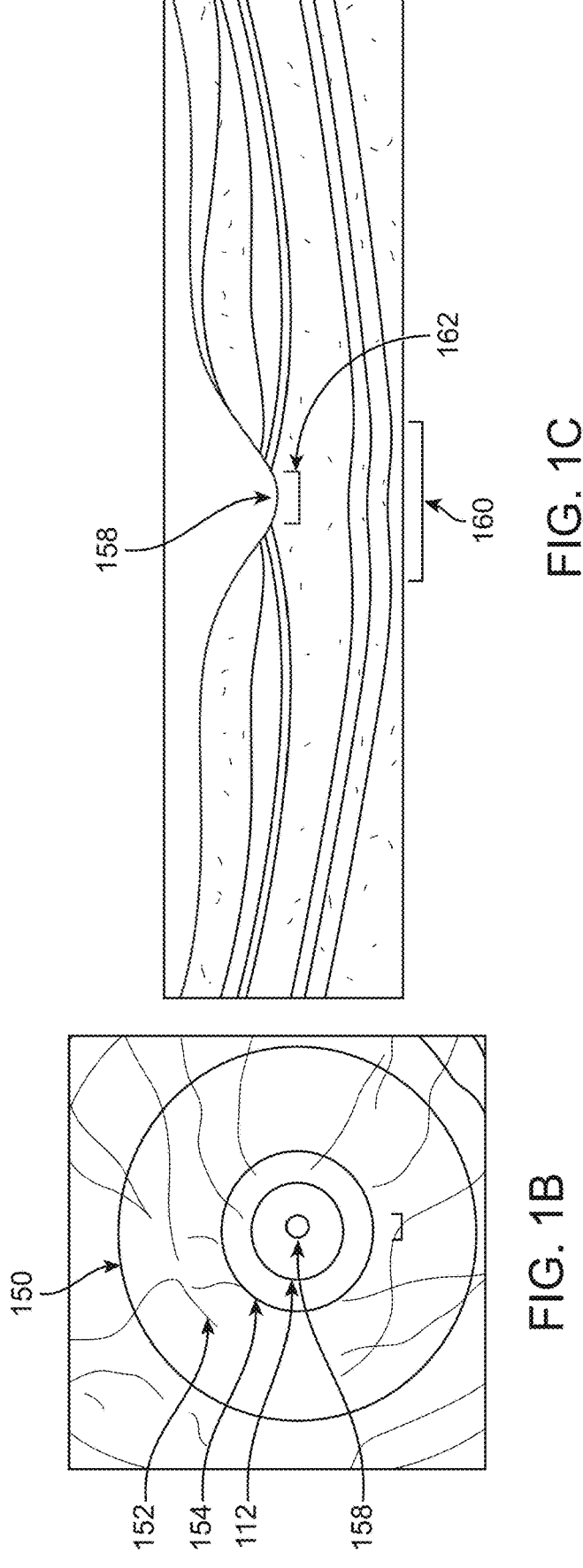
FIG. 1B shows structures of a retina of an eye suitable for incorporation in accordance with some embodiments.
FIG. 1C shows an umbo within an avascular zone of a retina, in accordance with some embodiments.

FIG. 1B shows structures of the retina of the eye and FIG. 1C shows an umbo within an avascular zone of a retina. The retinal structures include a macula 150, a perifovea 152, a parafovea 154, the fovea 112, the foveola 158, an avascular zone 160 and an umbo 162. The relative dimensions for the fovea 112, the foveola 158, and the umbo 162 can be approximately 1.5 mm, 0.35 mm and 0.2 mm, respectively. The foveal umbo 162 comprises a minute central depression at the center of the foveola, which has a diameter of approximately 0.15 to 0.2 mm across.

Although the umbo can be much smaller than other structures of the retina and only corresponds to 0.1 to 1 degree of the human visual field, the umbo has the highest cone density, peak sampling density, and cortical magnification, as compared with other areas of the fovea. Although the umbo is a minuscule part of the fovea by area, during fixation-limited, high-acuity tasks the umbo may contribute disproportionately to perception and visual acuity.

Figure 2:
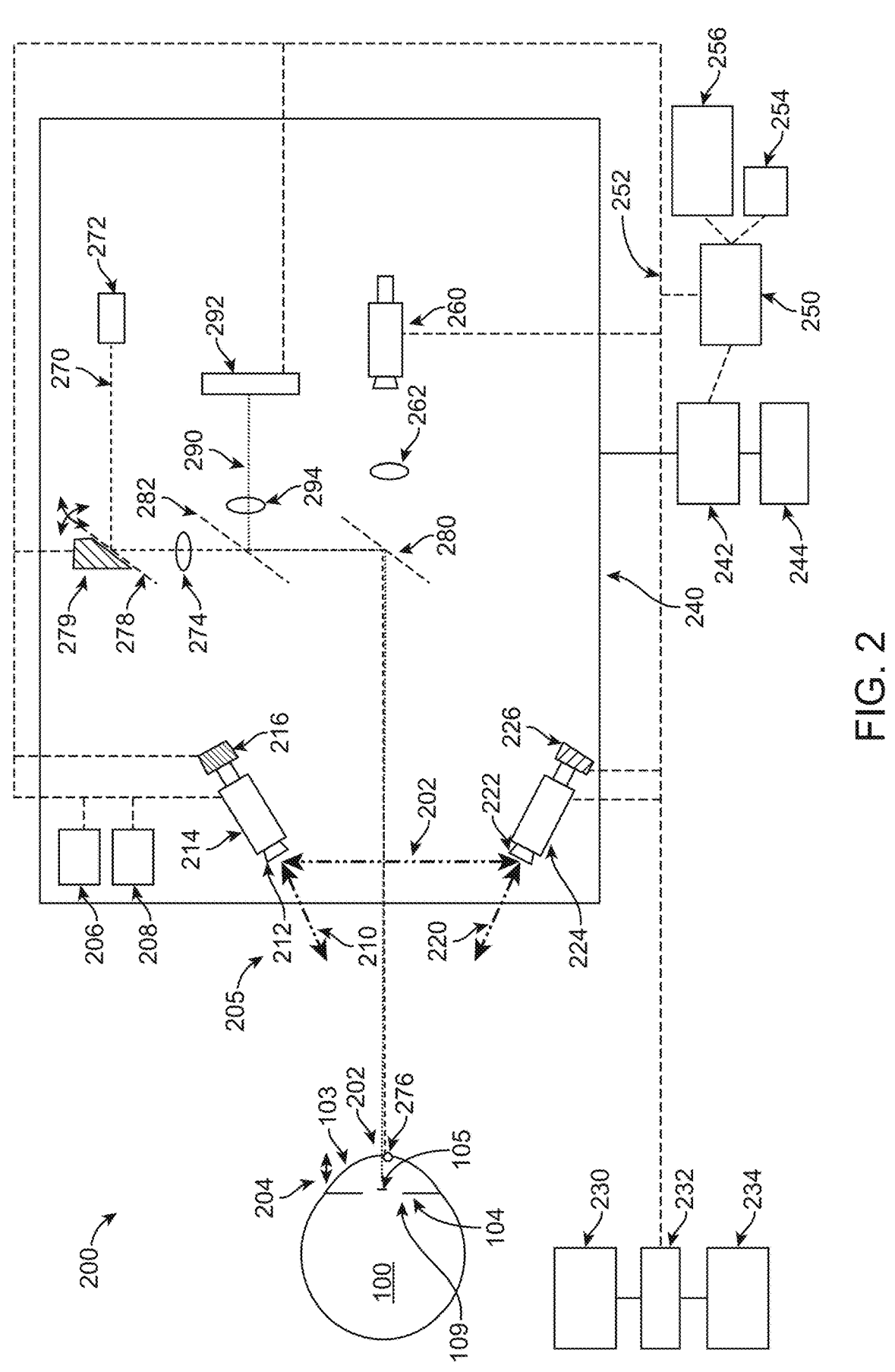
FIG. 2 shows an optical alignment system, in accordance with some embodiments.

FIG. 2 shows an optical alignment system 200. In some embodiments, the system 200 comprises a processor 252 is coupled to one or more components of the system with communication lines 252. In some embodiments, the system 200 comprises a stereoscopic imaging system 205 to generate parallax images of an optical surface such as an eye. The stereoscopic imaging system 205 comprises a first optical path 210, e.g. a right optical path, and a second optical path 220, e.g. a left optical path, configured to generate first and second parallax images, respectively. The first optical path 210 comprises a first optics 212 such as a first lens and the second optical path 220 comprises a second optics 222 such as a second lens. The first lens is separated from the second lens by a distance 202. In some embodiments, the first lens comprises a first portion of an objective lens and the second lens comprises a second portion of an objective lens, as described herein. In some embodiments, the first optical path 210 comprises a first camera 214, and the second optical path comprises a second camera 224. In some embodiments, the processor 250 is coupled to first camera 214 and the second camera 224 to capture and record first and second parallax images.

In some embodiments, the first optical path 210 is located on a first side of the fixation beam 290 and the second optical path 220 is located on a second side of the fixation beam 290. In some embodiments, the first optical path is located on a right side of the fixation beam and the second optical path is located on a left side of the fixation beam, from the perspective of a person or imaging system looking at the eye, for example.

In some embodiments, the optical path 210 is coupled to a first optical switch 216, and the second optical path 220 is coupled to a second optical switch 226. In some embodiments the first optical switch and the second optical switch are configured to alternate views between the first optical path and the second optical path. In some embodiments, the processor is configured to open and close the optical switch 226.

In some embodiments, a fixation beam 290 is directed to eye 100 to entrain fixation of the subject. The fixation beam 290 can be generated with a fixation beam source 292. The fixation beam source may comprise any suitable source of visible light, such as one or more of a laser, a Helium Neon (HeNe) laser, a laser diode, a diode, a display, a micro display, an LCD display or an OLED display, for example. In some embodiments, a lens 294 is located along the path of fixation beam 290. The lens can be provided to provide appropriate vergence of the fixation beam on the eye, and may comprise a variable focus lens, for example. In some embodiments, the fixation beam is substantially collimated at the eye, and the eye focuses the lens onto the foveola and umbo of the eye, for example. Alternatively or in combination, the vergence of the beam can be adjusted in accordance with a refraction of the eye 100.

In some embodiments, the processor 250 is coupled to the fixation beam to provide illumination to the subject to entrain fixation of the subject. In some embodiments, the processor 250 is configured to change a color of the illumination beam 290 from a first color to a second color, for example.

In some embodiments, the fixation beam 290 is directed toward the eye 100 and reflected off cornea 103 to generate a first Purkinje image 105. In some embodiments, the Purkinje image is located at a distance 204 from a vertex of the cornea. In some embodiments, the location of the Purkinje image 105 shifts with respect to one or more of a surface of the cornea or the pupil, when viewed from either side the first optical path or the second optical path. This shift in the location of the Purkinje image between optical paths can be used to determine the location of the one or more of the Purkinje image or the pupil, for example. In some embodiments, the shift of the Purkinje image is relative to the location of the cornea, for example in relation to the aiming beam focused on the vertex of the cornea.

In some embodiments, the first optical path 210 is separated from the second optical path 220 by a distance 202. In some embodiments, distance 202 corresponds to distance between lenses, such as a distance between entrance pupils of lenses or of an entrance pupil of an objective lens for example. In some embodiments, the distance 212 is related to a separation of the Purkinje image and another structure of the eye when viewed along the first optical path and the second optical path. In some embodiments, the separation of the Purkinje image 105 viewed along the optical paths is related to an angle between the first optical path and the second optical path referenced from the Purkinje image. In some embodiments the angle is related to a distance of the Purkinje image from the first entrance pupil of the first lens along the first optical path and a second distance from a second entrance pupil of the second lens along the second optical path, for example. In some embodiments, the shift in locations of ocular structures between the first image from the first optical path and the second image from the second are used to triangulate locations of the ocular structures, such as one or more of the iris, the virtual image of the iris, the pupil, the virtual image of the pupil, or the Purkinje image, for example.

In some embodiments, the system 200 comprises an aiming beam 270, which is directed toward an optical surface such as an eye. The aiming beam can be generated with a light source 272. The light source 272 may comprise any suitable light source such as a laser or a diode, for example. In some embodiments, a lens 274 is located along a path of aiming beam 270. The lens 274 can be configured to focus the aiming beam to a small spot on the cornea, such as one or more of a waist, point, or dot, for example. In some embodiments, the aiming beam is configured to image a small aperture onto the cornea, such as an aperture of a diode or external aperture located outside the diode, for example adjacent the diode. In some embodiments, the lens 274 focuses the aiming beam onto the cornea with a small cone angle (large F number), such that the patient can see the aiming beam when focused to a spot on the cornea, for example when the aiming beam has been aligned with the fixation beam.

In some embodiments, the aiming beam is optically coupled to a scanner 279 configured to scan the fixation beam laterally across an optical surface of the eye, such as a cornea of the eye. The scanner 279 may comprise one or more mirrors 278, for example. In some embodiments, the scanner comprises one or more of a gimballed mirror, a pair or mirrors, an electro-actuated scanner, a galvanometer, a pair of galvanometers, or a MEMS actuator, for example. In some embodiments, the lens 274 is located at a distanced from scanner 278 to provide telecentric scanning, such that the aiming beam 270 remains substantially parallel to the fixation beam, e.g. substantially parallel to within about 0.5 degrees and optionally 0.1 degrees. In some embodiments, the lens 274 is located along an optical path of the fixation beam at a distance corresponding to a focal length of lens 274, so as to provide telecentric scanning of beam 270.

In some embodiments, the aiming beam is scanned from the first location to the second location with a lens and one or more mirrors in a telecentric configuration while the fixation beam remains fixed, for example.

In some embodiments, the aiming beam is substantially parallel to the fixation beam, which can help to establish that the aiming beam is appropriately aligned with the fixation beam. With myopic patients, if the substantially parallel aiming beam is not appropriately aligned with the fixation beam, the subject may observe a shift in the location of the aiming beam relative to the fixation beam, which corresponds to the refractive error of the subject and the error of the aiming beam.

In some embodiments, the fixation stimulus comprises a plurality of colors, and the fixation stimulus is aligned with an achromatic axis of the umbo of the eye of the patient. Work in relation to the present disclosure suggests that fixation stimulus comprising a plurality of colors can be helpful to align with the achromatic axis of the eye, for example with the umbo of the eye. In some embodiments, if the fixation stimulus comprising a first color and a second color, for example a first beam and a second beam, is not sufficiently aligned with the achromatic axis of the eye, the fixation stimulus may appear asymmetrical to the subject due to dispersion of the light of the first color and the second color along the optical path to the umbo of the eye. In some embodiments, if the fixation stimulus comprising a first color and a second color, for example a first beam and a second beam, is sufficiently aligned with the achromatic axis of the eye, the fixation stimulus may appear symmetrical to the subject due to a lack of dispersion of the light of the first color and the second color along the optical path to the umbo of the eye because the light path is aligned with the achromatic axis of the umbo of the eye.

In some embodiments, the processor is coupled to the scanner 279 to allow the processor to control movements of the aiming beam, for example in response to user input as described herein.

In some embodiments, the processor 250 is coupled to the aiming beam 270 to control illumination of the aiming beam, for example. In some embodiments, the processor is configured to control illumination of the fixation beam and the aiming beam for example. In some embodiments, the fixation beam comprises a first color and the aiming beam comprises a second color different from the first color. In some embodiments, the processor is configured to mix the first color of the fixation with the second color of the fixation beam. Alternatively or in combination the processor can be configured to alternate illumination of the fixation beam and the aiming beam, which can provide different colors and cues to the subject. In some embodiments, the aiming beam appears at the same location as the fixation beam from the subject's perspective, for example when the aiming beam is aligned with the Purkinje image as described herein. In some embodiments, the processor is configured to illuminate the fixation beam and the aiming beam at the same time, so that the patient perceives intermittent, superimposed colors, such as a color intermediate to the first color and the second color.

In some embodiments, the system 200 comprises an iris camera 270 configured to image the iris, for example the virtual image of the iris. In some embodiments, the iris camera 260 comprises a lens 262 to image the iris. In some embodiments, the iris camera 270 is coupled to the processor to capture and record images of the iris, for example.

In some embodiments, the iris camera 260 is configured to image the iris in focus and out of focus at the cornea when the aiming beam 270 is focused to a small spot on the cornea and blurred at the iris, for example.

In some embodiments, one or more of camera 214, camera 224 or camera 260 is configured to measure structure of the iris. In some embodiments, the processor is configured to measure cyclotorsion of the iris in response to images from the one or more cameras. In some embodiments, a cyclotorsion angle of the eye comprises a rotation of the eye about an axis of the eye, such as one or more of the optical axis, the visual axis, or the line of sight, for example.

The system 200 may comprise one or more beam splitters configured to combine the beams and optical paths. In some embodiments, a beam splitter 282 is configured to combine the aiming beam 270 with the fixation beam 290. In some embodiments, a beam splitter 280 is couple the iris camera 260 to the optical paths of the aiming beam 270 and the fixation beam 290, for example. Additional beam splitters can be used, for example to couple a treatment laser beam such as an excimer laser beam to the optical path of one or more of the aiming beam 270, fixation beam 290, or the iris camera 290, for example.

In some embodiments, the system 200 comprises a subject support 230. The subject support may comprise any suitable support such as a chair, reclining chair, bed, chinrest, forehead engagement structure, or bite bar, for example. In some embodiments, the system comprises a linkage such as an XYZ movement stage configured to move the patient support and the patient supported thereon with 3 degrees of freedom. In some embodiments, the XYZ stage comprises a linkage of a commercially available laser treatment system such as a LASIK system configured to move a bed of a patient, for example. In some embodiments, the linkage is coupled to a base 234, such as a slit lamp table, for example. In some embodiments, the linkage 234 is supported with a base 234 configured to remain stationary while the linkage 232 moves the support 240.

In some embodiments, the system 200 comprises a system support 240. The system support may comprise any suitable support such as an arm, chassis, frame, housing, or other structure to support the stereoscopic imaging system, for example. In some embodiments, the system comprises a linkage such as an XYZ movement stage configured to move the support with 3 degrees of freedom. In some embodiments, the XYZ stage comprises a slit lamp base, for example. In some embodiments, the linkage 242 is supported with a base 244 configured to remain stationary while the linkage 242 moves the support 240.

In some embodiments, the processor 250 is coupled to a user interface 254 and a display 256, for example. In some embodiments, the user interface 254 comprises a user interface of a touch screen display, for example. Alternatively or in combination the user interface may comprise a joy stick, buttons or touch pad, for example. In some embodiments, the touch screen display comprises virtual buttons or touch pads, for example. In some embodiments, the user interface is configured to move the aiming beam 270 in two dimensions across the surface of the cornea, for example. Alternatively or in combination, the user interface can be configured to move one or more of the support 230 or the support 240 in response to user inputs, for example.

In some embodiments, the system 200 comprises an illumination source 206 configured to illuminate the eye 100. In some embodiments, the user interface is configured to control illumination, for example. In some embodiments, the user interface is configured to adjust the illumination of the eye to one or more of scotopic, photopic or mesopic illumination, for example. In some embodiments, the processor 250 is coupled to the illumination source 208 to control illumination of the eye.

In some embodiments, the system 200 comprises a photo detector 208 to measure illumination of the eye, for example. In some embodiments, the photo detector 208 is coupled to the processor to record the illumination of the eye, for example.

In some embodiments, the processor is coupled to the illumination source and configured to measure pupil size with one or more of camera 214, camera 224, or camera 260 and measure a size of the pupil, such as a diameter of the pupil, in response to different illumination conditions. In some embodiments, the processor is configured to measure a change in a location of the Purkinje image under different illumination conditions and to record the change in the location of the Purkinje image in relation to a center of the pupil such as a centroid of the pupil.

While the system 200 can be configured in many ways, in come embodiments, the first optical path 210 and the second optical path 220 are configured to focus at a common plane of the eye. In some embodiments, the common plane focal is located away from a first Purkinje image 105. In some embodiments, the common focal plane is located on a cornea 103 of the eye. Alternatively, the common plane can be located on a virtual image of the iris corresponding to an entrance pupil 107 of the eye, or on the Purkinje image 105, for example. When the common focal plane is located away from the cornea, for example on the Purkinje image, a location of cornea 103 can shift between the first parallax image and the second parallax image, instead of the Purkinje image, for example.

In some embodiments, the alignment beam 270 is substantially parallel with the fixation beam 290 when aligned between the first reflection of the Purkinje image from the first optical and the second reflection of the Purkinje image from the second optical path. In some embodiments, the alignment beam 270 appears the subject to be at a location matching a perceived location of the fixation beam 290, for example.

While the system can be configured in many ways, in some embodiments a first color of the fixation beam corresponds to a fixation phase and a second color of the alignment beam corresponds to an alignment assessment phase.

In some embodiments, the user interface 254 comprises one or more comprises one or more components of the display 256. In some embodiments, the processor is configured to provide one or more icons of user interface 254 on display 256.

In some embodiments, the processor is configured to receive an input configured to move an alignment beam in four directions in relation to the display to perform alignment. In some embodiments, the processor is configured to provide a user interface that includes a visual symmetry indicator displaying the first reflection of the fixation light beam and the second reflection of the fixation light beam in relation to an aiming beam focused on a cornea of the eye.

In some embodiments, the user input 254 is configured to allow the user to adjust a location of the aiming beam in relation to the first reflection and the second reflection in the combined image.

In some embodiments, the processor 250 is configured to determine a centroid of the pupil and position the aiming beam at a first location corresponding to the centroid of the pupil and receive the user input to place the aiming beam at a second location corresponding to alignment with the first reflection and the second reflection.

In some embodiments, a pair of "lock" events is recorded by the processor 250 upon edge-kiss confirmation in two distinct cycles of the blinking fixation beam and an aiming beam, and wherein the system computes a mean of those coordinates as a final alignment location of the aiming beam.

In some embodiments, the processor is configured to provide a marker corresponding to a central location between the first reflection and the second reflection in response to the first parallax image and the second parallax image, wherein the marker indicates an inferred visual axis target corresponding to the umbo.

In some embodiments, the processor is configured to provide a white dashed ring indicating an inferred visual axis, in which a centration of the white dashed ring is based on a mean location of each of the first reflection and the second reflection and optionally wherein the mean location comprises one or more of an XY coordinate system or a radial coordinate system.

In some embodiments, locations of the first reflection and the second reflection correspond to coaxially sighted corneal light reflex (CSCLR), for example.

The processor 250 can be configured to provide alignment data in any suitable computer readable format, either to another device or internally, for example. In some embodiments, the output data comprises a location one or more of an XY coordinate system or a radial coordinate system.

In some embodiments, the processor 250 is configured to generate combined image data from the first parallax image and the second parallax image. In some embodiments, the processor is configured to determine a center of the pupil and display a marker corresponding to the center of the pupil in the combined image and optionally wherein the center of the pupil comprises a centroid of the pupil. In some embodiments, the processor 250 is configured to determine an offset between a center of the pupil and a reflection of the fixation target in each of the first parallax image and the second parallax image and optionally wherein the center of the pupil comprises a centroid of the pupil, for example.

In some embodiments, the user input of the user interface 254 is configured to allow the user to adjust a location of the aiming beam in relation to the first reflection and the second reflection in the combined image. In some embodiments, the processor 250 is configured to determine a centroid of the pupil and position the aiming beam at a first location corresponding to the centroid of the pupil and receive the user input to place the aiming beam at a second location corresponding to alignment with the first reflection and the second reflection. In some embodiments, the user interface 254 is configured to allow the user to move the aiming beam into an aligned configuration in the combined image, the aligned configuration comprising the aiming beam being located along a line extending between the first reflection and the second reflection and substantially equidistant from the first reflection and the second reflection and optionally such that the first reflection and the second reflection are symmetrically disposed on either side of the aiming beam, as described herein, for example with reference to FIGS. 5B to 8A.

In some embodiments, the user interface 254 comprises an input configured to allow the user to adjust one or more of the color, the timing, the duration of a cycle, or a gap of illumination of one or more light sources of the stimulus presented to the subject over a plurality of illumination cycles. In some embodiments, the interval between cycles of illumination is varied by the user in response to a user input, for example. In some embodiments, this change in the cycling may provide improved attention and overall fixation stabilization in accordance with an individual subject, for example. The user interface can be configured for the user to adjust one or more of a first duration of a first light beam, a second duration of a second light beam, an overlap of the first light beam with the second light beam, a gap between illumination with the first light beam and the second light beam, or a timing of cycling between the first light beam and the second light beam. The user interface can be configured to provide the adjusted one or more of the color, the timing, the duration of a cycle, or gaps of illumination of one or more light sources of the stimulus presented to the subject, until a neurovisual lock in has been detected, as described herein.

Figure 3:
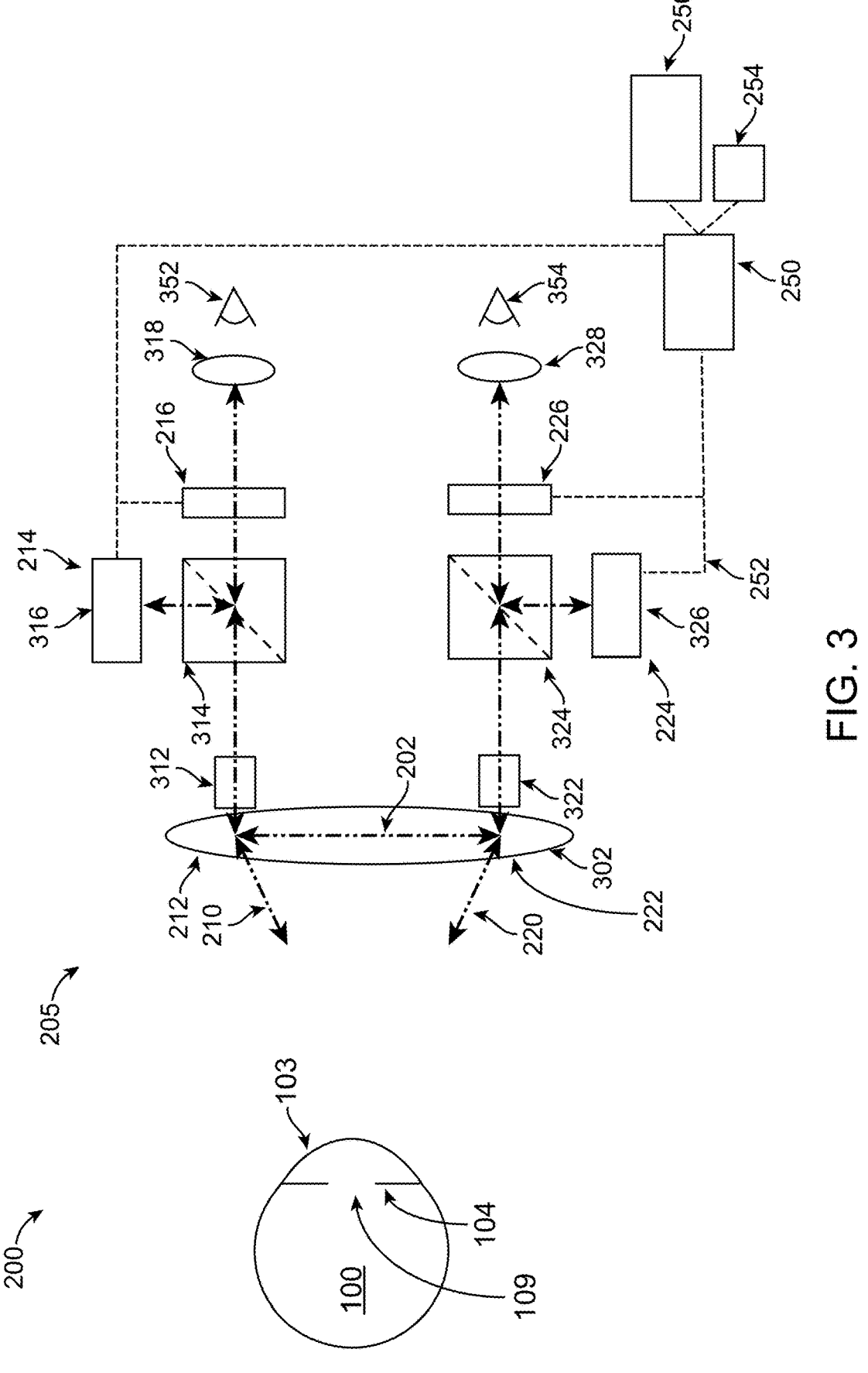
FIG. 3 shows a stereoscopic imaging system, in accordance with some embodiments.

FIG. 3 shows a stereoscopic imaging system 205, in which the stereoscopic imaging system comprises an objective lens 302 of a stereoscopic microscope, for example. The stereoscopic imaging system shown on FIG. 3 can be combined with any of the components of the system 200 as described herein. The first optic 212 comprises a first portion of the objective lens 302 and the second optic 222 comprises a second portion of the objective lens 302. In some embodiments, a first aperture 312 is located on a first side of the objective lens 302 and a second aperture 322 is located on a second side of the objective lens 302, so as to define first and second entrance pupils respectively. The distance 202 extends between the first entrance pupil and the second entrance pupil, for example. As one or ordinary skill in the art will appreciate, the first entrance pupil comprises a virtual image of the first aperture 312 as seen from the location of the eye, and the second entrance pupil comprises a virtual image of the second aperture 322 as seen from the location of the eye 100.

The imaging system comprises a first beam splitter 314 coupled to the first optical path 210 and a second beam splitter 324 coupled to the second optical path 220. The first beam splitter 314 transmits a portion of the light from the first optical path 210 to the first camera 214. The second beam splitter 324 transmits a portion of the light from the second optical path 220 to the second camera 224. In some embodiments the first and second cameras 214, 224, comprise first and second sensor arrays 316, 326, respectively. The sensor arrays may comprise any suitable sensor array for use with a camera, such as a 2D sensor array, for example. The first and second sensor arrays may comprise color sensor arrays. The sensor arrays 316, 326, can be coupled to processor 250 to capture and record images from the first and second optical paths, respectively.

In some embodiments, the first beam splitter is coupled to the first optical path between the objective lens and the optical switch to capture the first parallax image when the optical switch is closed along the first optical path, and wherein the second beam splitter is coupled to the second optical path between the objective lens and the optical switch to capture the second parallax image when the optical switch is closed along the second optical path. In some embodiments, the processor coupled to the sensor arrays is capable of acquiring image data while one of the optical switches is closed, which allows the processor to acquire image data at a duty cycle of 100% during switching, for example.

In some embodiments, the stereoscopic image system comprises first optical switch 216 and second optical switch 226 located along first and second optical paths 210, 220, respectively. The optical switches can be coupled to processor 250 to control opening and closing of the switches. The first and second optical switches may each comprise any suitable optical switch such as one or more of a shutter, a rotating aperture wheel, an electronic shutter, an optoelectronic shutter, a liquid crystal shutter or an optoelectronic shutter, for example.

In some embodiments, the first beam splitter 314 is coupled to the first optical path 210 between the objective lens 222 and the optical switch to capture the first parallax image when the optical switch is closed along the first optical path, and the second beam splitter 324 is coupled to the second optical path 220 between the objective lens and the optical switch to capture the second parallax image when the optical switch is closed along the second optical path. In some embodiments, this approach allows first image data to be captured from the first optical path with the first sensor array 316 when the first optical switch 216 is closed and second image data to be captured from the second optical path with the second sensor array 326 when the second optical switch 226 is closed, which can improve data acquisition.

In some embodiments, the stereoscopic imaging system comprises a first ocular (eye piece) and a second ocular (eye piece) coupled to the first and second optical paths 210, 220 respectively, to allow a user such as a surgeon to view the first and second images a first eye 352 and a second eye 354 with stereoscopic viewing, for example with a right eye and a left eye. In some embodiments, the second eye comprises a contralateral eye of the user.

In some embodiments, the processor is configured to close one optical path and open the other optical path to encourage the user to view the images with alternating left and right eye views. Work in relation to the present disclosure suggests that ocular dominance can result in the user seeing only one Purkinje image with the dominant eye, and the optical switching promotes the user seeing the Purkinje image with both eyes, in which the Purkinje image will appear offset with respect to other eye structures, in accordance with the angular separation of the first optical path 210 and the second optical path 220.

Figure 4:
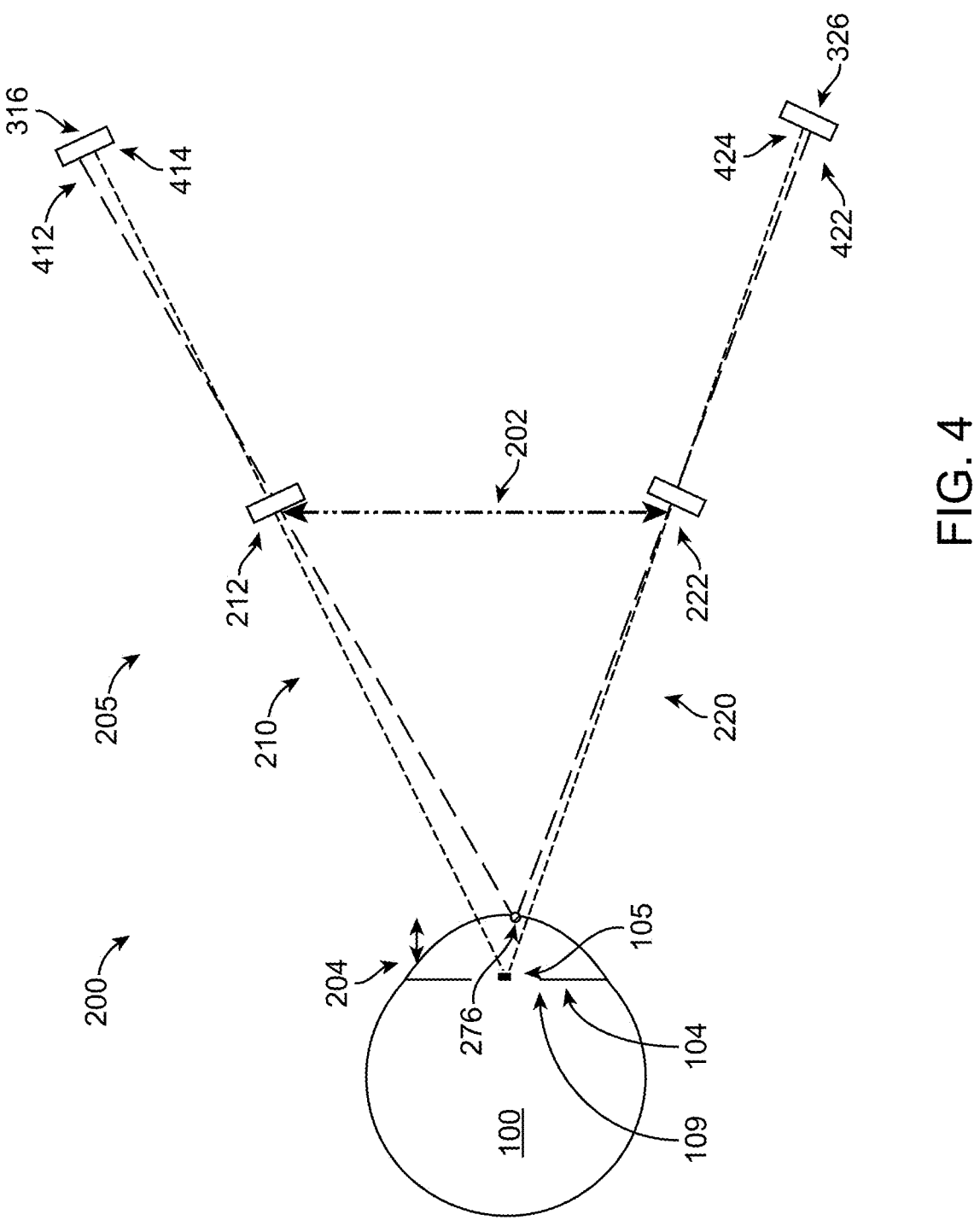
FIG. 4 shows triangulation with a stereoscopic imaging system, in accordance with some embodiments.

FIG. 4 shows triangulation of ocular structures with a stereoscopic imaging system. In some embodiments, triangulation is used to determine the location of one or more structures of the eye as described herein. The first Purkinje image 105 of the fixation beam is located behind the cornea of the eye at a distance 204. The first optic 212 is separated from the second optic 222 by a distance 202. The aiming beam 276 is focused to a spot on the cornea. The first parallax optical path 210 forms an image of the first Purkinje image 105 and the focused spot 276 on the first sensor array 316 at locations 414 and 412, respectively. The second parallax optical path 220 forms an image of the first Purkinje image 105 and the focused spot 276 on the second sensor array 326 at locations 424, 422, respectively.

While triangulation can be performed in many ways, in some embodiments, the locations 424, 422, of the aiming beam on sensor arrays 316, 326, respectively, can be used to determine the location of the aiming beam 276 on the surface of the cornea. In some embodiments, the locations on the sensor arrays are related to the separation distance 202, and magnification of the imaging system, and these can be used to triangulate the system. In some embodiments, the imaging system is calibrated with a test fixture placing targets at different locations corresponding to locations of the Purkinje image, the surface of the cornea, the iris and the pupil for example. In some embodiments, the locations of the Purkinje image and the aiming beam and iris and pupil can be performed without performing triangulation calculations, for example based on look up tables or based on calibration with a test fixture.

Figures 5A, 5B, 5C, 5D, 5E:
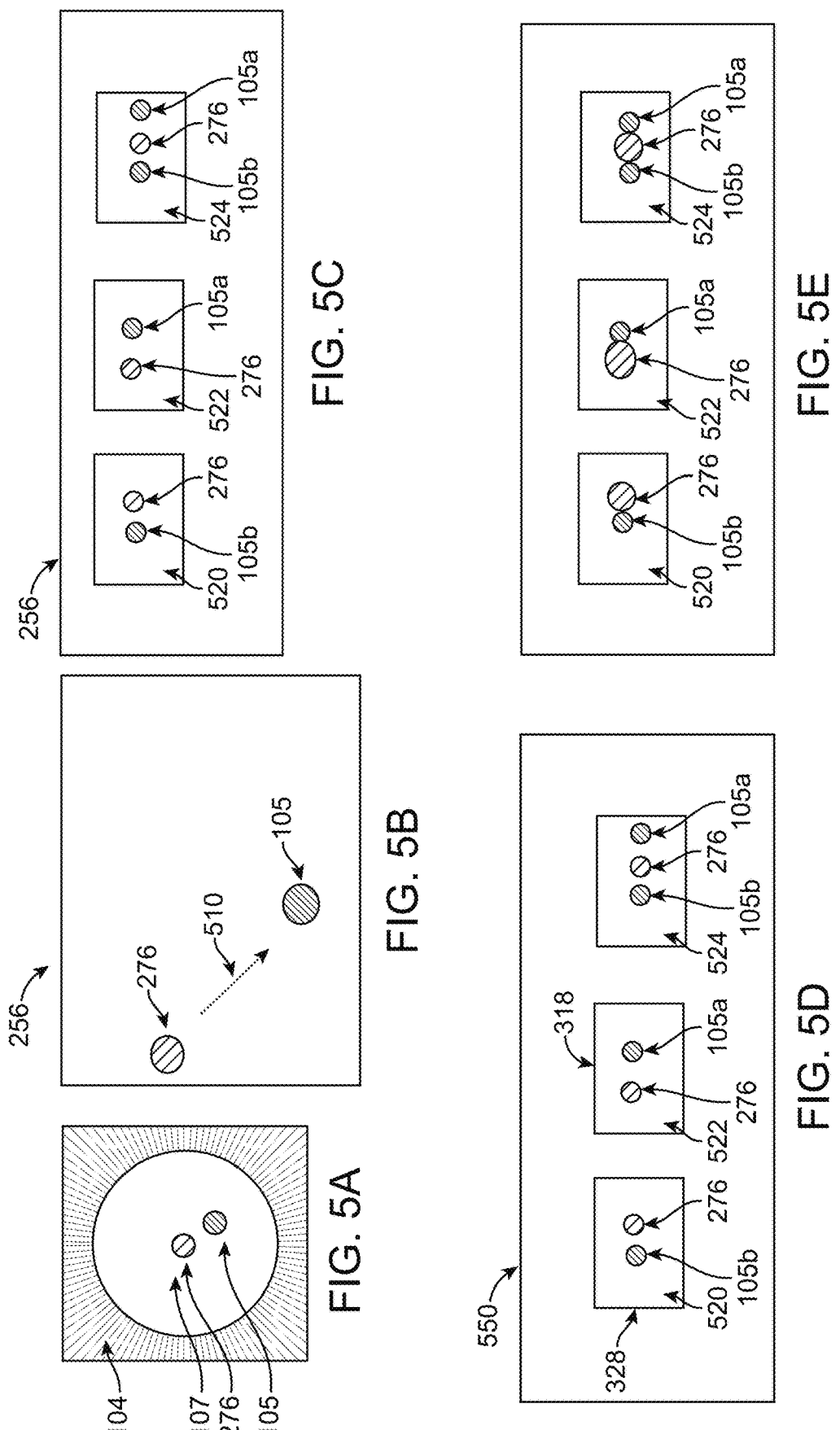
FIG. 5A shows a view of an eye with a stereoscopic microscope, in accordance with some embodiments.
FIG. 5B shows an initial configuration in which an aiming beam is aligned with a pupil and separated from the first Purkinje image, in accordance with some embodiments.
FIG. 5C shows images left view and right views and a combined view on a display, in accordance with some embodiments.
FIG. 5D show views through oculars of a microscope, in accordance with some embodiments.
FIG. 5E shows alignment of the aiming beam and fixation beam in an edge kiss configuration, in accordance with some embodiments.

FIG. 5A shows a view of an eye with a stereoscopic microscope. The microscope image shows the iris 104 and the focused spot 276 of the aiming beam is aligned with the entrance pupil of the eye viewing the fixation target. In some embodiments, the stereoscopic microscope comprises an operating microscope of a commercially available laser system such as a system to perform LASIK. In some embodiments, the system 200 is configured to automatically place the focused aiming beam spot at the center of the entrance pupil 107, e.g. at the centroid of the entrance pupil. As illustrated, the center of the entrance pupil 107 is not aligned with the Purkinje image 105, consistent with a subject having an angle Kappa greater than zero.

FIG. 5B shows an image of an eye as in FIG. 5A shown on a display 256. In the initial configuration the focused spot 276 of the aiming beam is aligned with a pupil and separated from the first Purkinje image, similar to the microscope view FIG. 5A. in some embodiments, the aiming beam spot 276 is moved toward the Purkinje image 105 as shown with arrow 510. In some embodiments, the movable mirror is moved in response to user input to place the spot 276 into alignment with the Purkinje image 105. Alternatively or in combination, one or more of the patient support or the system support can be moved to align the focused spot 276 with the Purkinje image 105.

In some embodiments, the system user interface is configured to provide a coarse alignment mode for movement shown with arrow 510 and a fine alignment mode for alignment with vernier acuity as described herein. In embodiments, when the aiming beam is far away from the Purkinje image, the two views of Purkinje image may appear on the same side of the aiming beam, and there might be confusion if a user were to attempt to place the focused spot adjacent to the wrong view of the Purkinje image. The fine and course alignment modes can be helpful to reduce such possible confusion, in accordance with some embodiments.

Once the aiming beam and fixation target are close to each other, the parallax views show the aiming beam at different locations with respect to the aiming beam, depending upon whether the eye is viewed from the first optical path or the second optical path.

FIG. 5C shows a left image view 520, a right image view 522, and a combined view 524 on a display 256. In the left image view 520, the Purkinje image comprises a left view Purkinje image 105b in relation to the focused spot 276 as seen along the left optical path (e.g. the second optical path). In the right image view 522 the Purkinje image comprises a right Purkinje image 105a in relation to the focused spot 276 as seen along the right optical path (e.g. the first optical path). The Purkinje images are on opposite sides in the left view and the right view. In the combined image view 524, image data from the first image on the first side (e.g. right side) and the second image from the second side (e.g. left side) are combined. In some embodiments, the aiming beam is used as a reference location to combine the right (first) image data and the left (second) image data. The combined image data can be provided on a display. Although the combined image may comprise images from the left view and the right view overlaid on each other, in some embodiments, computer generated markers are shown at the location of the focused spot 276, the location of the left (second) Purkinje image 105b and the right Purkinje image 105a, for example without overlaying the images from the left (second) and right (first) views. In some embodiments, these markers are provided on the display with a marker corresponding to a center of the pupil such as a marker corresponding to a centroid of the pupil.

In some embodiments, the focused spot and the Purkinje images are sized to allow a user to align the aiming beam and the two Purkinje images with vernier acuity. In some embodiments, in the aligned configuration, the aiming beam spot 276 (or aiming beam marker) is located between the two Purkinje images (or markers), for example located on a line extending between the two Purkinje images. In some embodiments, in the aligned configuration, the aiming beam spot 276 (or aiming beam marker) is located between the two Purkinje images (or markers), substantially equidistant to the left (second) and right (first) Purkinje images, 105b, 105a, respectively. For example, the aiming beam may appear to be placed on a line between the firsts and second Purkinje images with the Purkinje images evenly spaced from the aiming beam.

FIG. 5D shows a left image view 520, a right image view 522, and a combined view 524 as seen through left ocular 328 and right ocular 318 of the microscope such as an operating microscope or a slit lamp. With the combined view 552 as seen from the operating microscope, the optical switches open and close the left and right optical paths to generate the combined view, so that the user such as a surgeon sequentially sees the left eye image view 520 and the right eye image view 522. By alternating the view between the left (second) optical path and right (first) optical path, the user such as a surgeon is forced to view with the left eye and the right eye, in accordance with some embodiments. By alternating the viewing of the Purkinje image, the effects of ocular dominance may be reduced, and allow the user to align the left and right Purkinje images, for example with vernier acuity as described herein.

With reference to FIGS. 5C and 5D, in some embodiments a first gap extends between the first reflection and the aiming beam on a first side of the aiming beam and a second gap extends between the second reflection and the aiming beam on a second side of the aiming beam.

In some embodiments, the user interface is configured move the aiming beam along a line extending between the first reflection and the second reflection toward an aligned configuration.

FIG. 5E shows alignment of the focused spot 276 of aiming beam and first and second Purkinje images, 105a, 105b, and a fixation beam in an edge kiss configuration, in accordance with some embodiments. In some embodiments, the edge kiss configuration comprises a configuration in which the aiming beam spot 276 is located between the first and second Purkinje images 105a, 105b, respectively, and the aiming beam spot is located adjacent to the first and second Purkinje images. Alternatively or in combination, the aiming beam spot may overlap with the first and second Purkinje images, for example with an overlap of no more than about 10%, for example.

In some embodiments, overlap of the aiming beam and the fixation beam provides a color change at the area of overlap. For example, the aiming beam may comprise a first color and the fixation beam comprises a second color different from the first color. In some embodiments, the color of the aiming beam mixes with the color of the fixation beam to provide intermittent, superimposed colors, such as a color intermediate to the first color and the second color. For example, if the aiming beam has a red color and the fixation beam has a red color, the region of overlap may comprise an orange color and increase luminance, for example.

Figures 6A, 6B, 7, 8A, 8B:
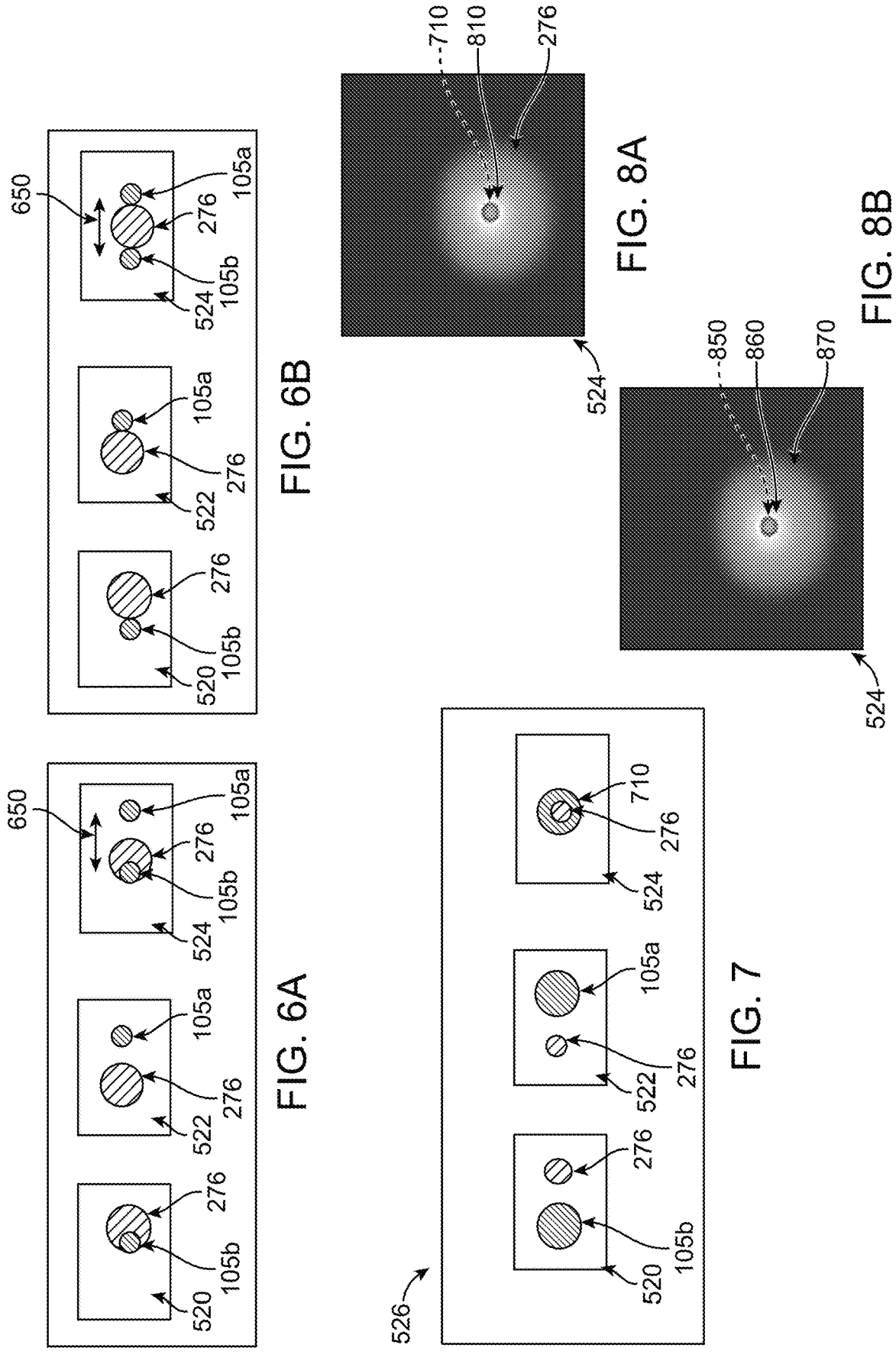
FIG. 6A shows a left image view, a right image view, and a combined view on a display, in which the Purkinje images are not aligned with the aiming beam, in accordance with some embodiments.
FIG. 6B shows alignment of the focused spot of aiming beam and first and second Purkinje images, and a fixation beam, in which the aiming beam has been moved from an unaligned configuration and in FIG. 6A to an aligned configuration, in accordance with some embodiments.
FIG. 7 shows a combined image on a display, in which the locations of the Purkinje images are averaged to generate the combined image, in accordance with some embodiments.
FIG. 8A shows a combined image in which the chrominance and luminance of the aiming beam spot has been combined with the chrominance and luminance of the combined Purkinje image, in accordance with some embodiments.
FIG. 8B shows chrominance and luminance of a first series of light pulses and a second series of light pulses provided to the eye of subject.

FIG. 6A shows a left image view 520, a right image view 522, and a combined view 524 on a display 256, in which the Purkinje images are not aligned with the aiming beam. The Purkinje images are on opposite sides in the left view and the right view as described herein. In the combined image view 524, image data from the first image on the first side (e.g. right side) and the second image from the second side (e.g. left side) are combined as described herein. In the combined view, the Purkinje images are shown separated by a distance 650. In some embodiments, the separation distance 650 is related to one or more of a curvature of the cornea, the angle of the first (right) and second (left) optical paths, or the separation distance between the first entrance pupil and the second entrance pupil, and the distance from the entrance pupils to the cornea. In some embodiments, the first and second Purkinje images appear to be tethered to each other during alignment with the aiming beam, because the separation distance does not change substantially.

FIG. 6B shows alignment of the focused spot 276 of aiming beam and first and second Purkinje images, 105a, 105b, and a fixation beam, in which the aiming beam has been moved from an unaligned configuration and in FIG. 6A to an aligned configuration. In the aligned configuration, the separation distance 650 is substantially the same (e.g. to within 1%) as the separation distance in the unaligned configuration of FIG. 6A. In the aligned configuration, the aiming beam spot 276 is located between the first and second Purkinje images 105a, 105b, respectively, and the aiming beam spot is located adjacent to the first and second Purkinje images. In some embodiments, in the aligned configuration the Purkinje images 105a, 105b and the aiming beam are colinear with each other and the Purkinje images are on opposite sides of and equidistant from the aiming beam spot 276, for example.

With reference to FIGS. 5B to 6B, in some embodiments in an aligned configuration, the aiming beam is located along a line extending between the first reflection and the second reflection. In some embodiments, in an aligned configuration, the aiming beam is located substantially equidistant between the first reflection and the second reflection and optionally equidistant to about 10 percent (%). In some embodiments, in an aligned configuration, the first reflection and the second reflection are located adjacent to the aiming beam in the combined image. In some embodiments, the aiming beam overlaps with the first reflection and the second reflection in the combined image.

FIG. 7 shows a combined image on a display, in which the locations of the Purkinje images are averaged to generate the combined image 524 to generate a combined Purkinje image 710. In the left image view 520, the left (second) Purkinje image 105b does not appear to be aligned with the aiming beam spot 276, for example related to parallax. In the right (first) image view, the Purkinje image 105a does not appear to be aligned with the aiming beam spot 276. In the combined image view 524 shown on a display 256, in which the Purkinje images appear aligned with the aiming beam. The aiming beam 276 is shown within the combined Purkinje image 710. Alternatively, the combined Purkinje image 710 may appear within the spot 276 of the alignment beam.

In some embodiments, the combined Purkinje image 710 comprises one or more of chrominance (color) or luminance of the combined Purkinje image with the aiming beam spot. In some embodiments, the processor is configured to combine the chrominance of the first and second Purkinje images with the chrominance of the spot 276 of the aiming beam. In some embodiments, the processor is configured to mix the colors, to provide intermittent, superimposed colors, such as a color intermediate to the first color and the second color, where the combined Purkinje image 710 and the aiming beam spot 276 overlap, for example. Alternatively or in combination, the processor can be configured to combine the luminance of the combined Purkinje image 710 and the aiming beam spot 276 where the two overlap. For example, a red aiming beam can be combined with a green fixation beam to generate a combined image 524 in which the areas of overlap comprise an orange color, which is brighter than both the combined Purkinje image 710 and the aiming beam, for example.

FIG. 8A shows a combined image 524 in which the chrominance and luminance of the aiming beam spot 276 has been combined with the chrominance and luminance of the combined Purkinje image 710. The combined Purkinje image 710 can be generated as described herein. The aiming beam 276 comprises a first color and associated chrominance, such as one or more of red, orange, yellow, blue, green, indigo or violet, and the combined Purkinje image comprises a different one of the one or more of red, orange, yellow, blue, green, indigo or violet. At an overlapping region 810, the processor is configured to generate a combined chrominance and luminance of the Purkinje image 105 and the aiming beam spot 276, such that the color comprises intermittent, superimposed colors, such as a color intermediate to the first color and the second color. The superimposed colors, such as the intermediate color at overlapping region 810 can be determined in many ways, for example by combining color palettes. For example, the aiming beam may comprise a red color and the fixation beam a green color and the overlapping region comprises an orange color. Alternatively or in combination, the luminance of the aiming beam spot 276 and the combined Purkinje image 710 can be combined to generate a combined luminance, for example by combining a luminance of the aiming beam spot with a luminance of the combined Purkinje image 810.

In some embodiments, the central location of the combined Purkinje image is identified with a marker 820, such as a circle for example.

In some embodiments, the processor 250 is configured to generate a combined image, in which chrominance and luminance can be combined. In some embodiments, an overlapping region 810 of the aiming beam and one or more of the first reflection or the second reflection, the processor is configured to combine a luminance and a chrominance of the aiming beam and the one or more of the first reflection or the second reflection at the overlapping region. In some embodiments, first color comprises one or more of red, orange, yellow, green, blue, indigo, or violet, and the second color comprises a different one of the one or more of red, orange, yellow, green, blue, indigo, or violet. In some embodiments, first color comprises red, blue or green and the second color comprises a different one of the red, blue or green. In some embodiments, the first color is configured to stimulate a first chromatic neural pathway of the user corresponding to the first color and the second color is configured to stimulate a second chromatic neural pathway of the user corresponding to the second color.

In some embodiments, the processor is configured to combine a chromatic luminance intensity of the first reflection marker or the second reflection marker with a chromatic luminance intensity of the aiming marker in response to an overlap, for example with reference to FIGS. 5B to 8B. In some embodiments, an overlapping region of the first reflection or the second reflection with the aiming beam comprises a composite color comprising the first color and the second color. In some embodiments, the overlapping region comprises a combined luminance. In some embodiments, the combined luminance at the overlapping region 810 is greater than a luminance the aiming beam at the overlapping region, or a luminance of the first reflection or a luminance of the second reflection at the overlapping region, for example. In some embodiments, wherein the processor is configured to generate a combined image comprising first and second overlapping regions, respectively, of the first reflection and the second reflection with the aiming beam. In some embodiments, the first and second overlapping regions each comprises a composite color. In some embodiments, the first and second overlapping regions each comprises a combined luminance.

In some embodiments, the processor is configured to display the reflection marker at a first location and a second reflection marker at a second location of the computer generated image with a variable offset from the one or more of the pupil or the aiming beam, and wherein the user input is configured to allow the user to place the aiming beam toward a line extending between the first location and the second location.

In some embodiments, the user interface is configured to allow the user to move the aiming beam into an aligned configuration in the combined image, the aligned configuration comprising the aiming beam being located along a line extending between the first reflection and the second reflection and substantially equidistant from the first reflection and the second reflection and optionally such that the first reflection and the second reflection are symmetrically disposed on either side of the aiming beam.

In some embodiments a separation distance 650 between the first reflection and the second reflection remains substantially fixed in the combined image in response to the user adjusting the location of the aiming beam. In some embodiments, the first reflection and the second reflection appear tethered to each other with the substantially fixed separation distance 650 in response to the aiming beam moving in the combined image. In some embodiments, the separation distance remains substantially fixed to within about 10%.

In some embodiments, the user input is configured to allow a user to align the first reflection, the second reflection and the aiming beam with vernier acuity, for example. In some embodiments, the vernier acuity corresponds to an arrangement of three targets, such as markers, reflections or Purkinje images arranged substantially colinearly and equidistant. Alternatively, or in combination, vernier acuity can correspond to alignment of two similarly shaped objects, such as a first circular pattern within a second circular pattern, for example as shown and described with reference to FIG. 8A or 8B.

In some embodiments, the separation distance 650 corresponds to a distance between a first entrance pupil along the first optical path and a second entrance pupil along the second optical path. In some embodiments, the first entrance pupil comprises one or more of a first entrance pupil of a first camera lens, a first entrance pupil of an objective lens, or a first entrance pupil of a first eye of a user and the second entrance pupil comprises one or more of a second entrance pupil of a second camera lens, a second entrance pupil of the objective lens, or a second entrance pupil of a second eye of the user as described herein.

Although FIGS. 5C to 8A refer to Purkinje images and aiming beams, in some embodiments, wherein the combined image data comprises data of the aiming beam, the first reflection, the second reflection and the pupil, for example.

The combined image data may comprise any suitable data. The combined image data may comprise one or more markers corresponding to one or more of a pupil, an aiming beam or a reflection of a Purkinje image, In some embodiments, the processor is configured to generate a combined image from first parallax image data and second parallax image data. In some embodiments, the combined image comprises a first Purkinje marker corresponding to a first location of the Purkinje image in the first parallax image and a second Purkinje marker corresponding to a second location of the Purkinje image in the second parallax image. In some embodiments, combined image comprises a marker corresponding to a central location of the pupil and optionally wherein the central location comprises a centroid of the pupil.

In some embodiments, combined image comprises a marker corresponding to a central location of the pupil and optionally wherein the central location comprises a centroid of the pupil. In some embodiments, the combined image comprises the iris and the Purkinje image.

In some embodiments, the processor is configured to generate a real time video stream of combined images from the first parallax image data and the second parallax image data. In some embodiments, the processor is coupled to a display to provide real time video stream on a display as described herein, for example.

In some embodiments, the microscope is configured to image the cornea of the eye in focus, and the iris and the Purkinje image out of focus. In some embodiments, the locations of the iris and the Purkinje image shift between the first parallax image and the second parallax image and a location of the cornea remains substantially fixed in the first parallax image and the second parallax image.

In some embodiments, the aiming beam is focused to a spot on a cornea of the eye, and the locations of the iris and the Purkinje image shift between the first parallax image and the second parallax image and locations of the spot in the first parallax image and the second parallax image remain substantially fixed.

FIG. 8B shows chrominance and luminance of a first series of light pulses and a second series of light pulses provided to the eye of subject. In some embodiments, the first and second series are configured to generate different patterns on one or more of the umbo or the foveola of the subject and provide one or more of spatial, temporal, or luminance cues so as to engage visual neural system to entrain fixation of the subject. In some embodiments, the one or more of spatial, temporal, or luminance cues so as to engage visual neural system are associated with vernier acuity. In some embodiments a first pulse of a first color is overlapped with a second pulse with a second color to provide chrominance and luminance cues to the subject as described herein. In some embodiments, a first series of light pulses of a first color such as light from a fixation beam appears as a first stimulus 850 on the retina, and a second series of light pulses of a second color such as light from an aiming beam appears as a second stimulus 870 on the retina. In some embodiments, an intermediate zone 860 provides one or more of spatial or temporal overlap of the stimulus, so as to provide color mixing. In some embodiments, temporal overlap provides one or more of intermittent or superimposed colors, such as a color intermediate to the first color and the second color. In some embodiments, the first series of light pulses is associated with a different sized spot than the second series of light pulses on the retina, which may help to provide spatial differences so as to engage neural pathways associated with vernier acuity, which can be associated with the foveola and umbo. Alternatively or in combination, the change in wavelength between the first light pulses and the second light pulses may present different patterns on the retina to provide the spatial differences, for example from image structure associated with different wavelengths of light.

The first series of pulses may comprise a first color and associated chrominance, such as one or more of red, orange, yellow, blue, green, indigo or violet, and the second color may comprise a different one of the one or more of red, orange, yellow, blue, green, indigo or violet. At an overlapping region 860, a combined chrominance and luminance of the first series of pulses and the second series of pulses provides a perceived intermittent or superimposed colors, such as a color intermediate to the first color and the second color. In some embodiments, the different colors stimulate different channels of the neural pathways of the subject, such as one or more of red, blue or green neural pathways associated with one or more of red, blue, or green, cones, respectively. For example, the first color may comprise a red color and the second color may comprise a green color, and the overlapping region 860 comprises an orange color. Although reference is made to red and green, other colors may be used, such as colors of a color palette, for example yellow.

Figure 9:
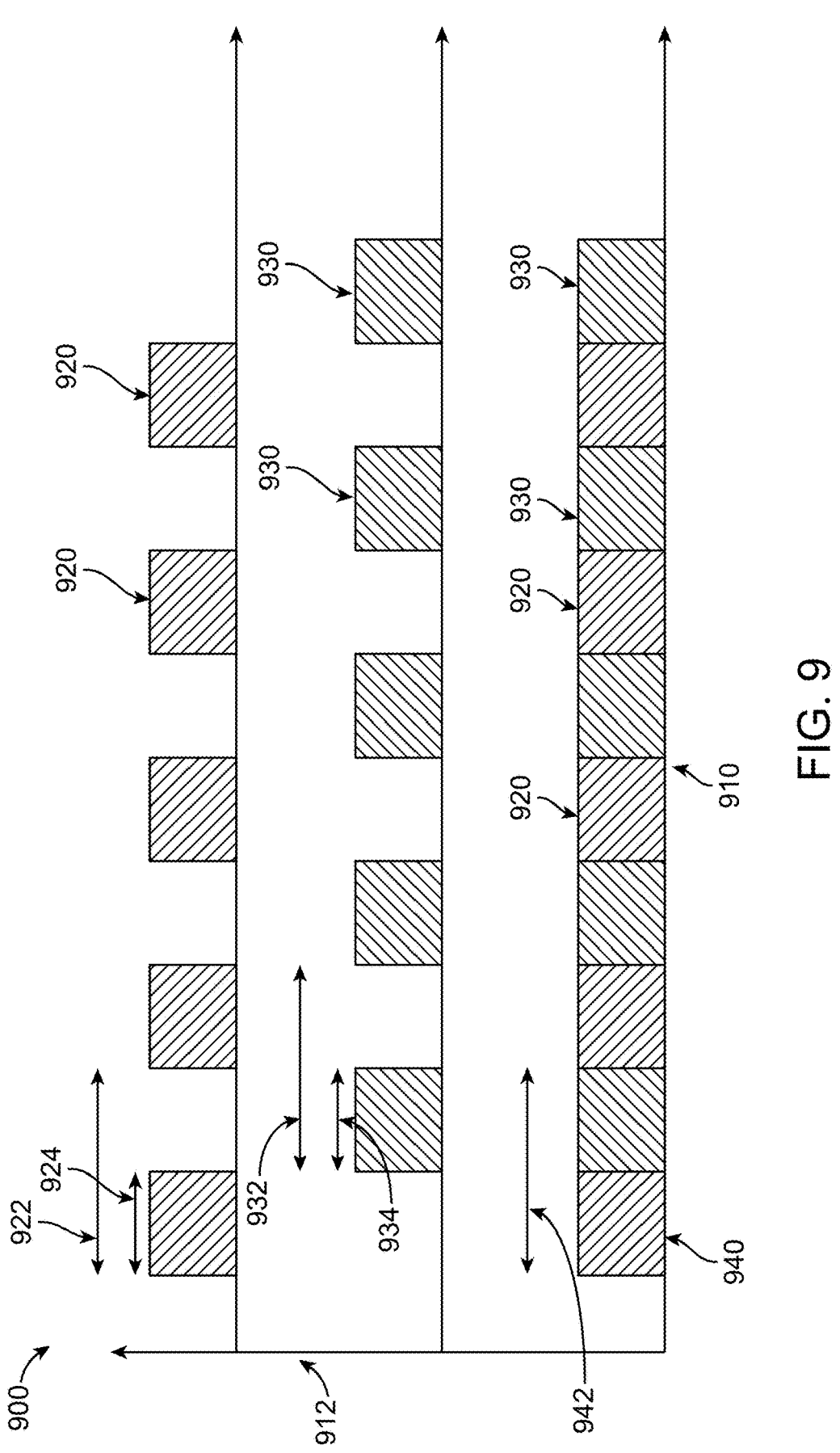
FIG. 9 shows chromatic cycling of a combined series of light pulses of different colors, in accordance with some embodiments.

FIG. 9 shows chromatic cycling 900 of a combined series of light pulses 940 of different colors. The combined series of light pulses 940 may comprise a combined series of light pulses of one or more of the fixation beam or the aiming beam, for example. In some embodiments, the combined series of light pulses comprises light from the fixation beam combined with light from the aiming beam. Alternatively, the combined series of light pulses may comprise a series of light pulses from fixation light beam source comprising a display.

In some embodiments, the combined series of light pulses is configured to provide illumination of the retina with a duty cycle within a range from 75 percent to 100%, for example.

While the combined series of light pulses can be generated in many ways, the combined series of light pulses may comprise light from a first source such as the aiming beam and light from a second source such as fixation beam. Alternatively or in combination, the poly chromatic series of light pulses may comprise light pulses may comprise light pulses from a display, in which the display changes a color of light emitted from the display with a first color at a location on the display to a second color at the location of the display, and the location on the display remains substantially fixed for the first color and the second color, for each illumination cycle. In some embodiments, the series of light pulses is provided by a first beam with a first color and a second beam with a second color, in which the beam paths are combined with a beam splitter, for example. The beams may emit light in an interleaved manner along the beam paths, for example. In some embodiments, the series of pulses do not overlap temporally, such that only a single color is emitted at any time during the first and second series of pulses.

The series of light pulses may provide any suitable duty cycle of illumination for each of the light beams and the combined beam. In some embodiments, the combined duty cycle is within a range from 70% to 100%, for example within a range from 80% to 100%. In some embodiments, for each of the plurality of cycles the fixation target is dark after the second duration and prior to a first duration of a next cycle, for example.

In some embodiments, the first light pulses and the second light pulses, each comprise a duty cycle of 50% and are provided in an interleaved manner, for example without temporal overlap, so as to continuously illuminate the eye of subject with a 100% duty cycle. Alternatively, the first series of light pulses and the second series of light pulses may comprise a 40% duty cycle, such that the duty cycle of the combined pulses is approximately 80%. In some embodiments, the first light pulses and the second light pulses are configured to overlap temporally, so as to provide color mixing of the color of the first light pulses and the color of the second light pulses. In some embodiments, the first series of pulses with a first color comprises a 100% duty cycle, and the second series of pulses with a second duty cycle comprises a 50% duty cycle, so that the subject sees the first color with a 50% duty cycle and a combined color from the first light pulses and the second light pulses with a 50% duty cycle.

In some embodiments, the user of one or of the microscope or the display sees similar colors and changes in colors. This changing of colors may also assist the user in aligning the targets, for example.

In some embodiments, the first color of the first series of pulses comprises red, blue or green and the second color comprises a different one of the red, blue or green. In some embodiments, the first color of the first series of pulses comprises red, blue, green, or yellow and the second color comprises a different one of the red, blue, green or yellow. In some embodiments, the first color comprises one or more colors of a first color palette and the second color comprises one or more colors of a second color palette, the first color palette different from the second color palette In some embodiments, a first series light pulses 920 comprise light from a first source such as light from the aiming beam and a second series of light pulses 930 comprise light from the fixation beam. In some embodiments, the processor is configured to turn the first light source and the second light source on and off at fixed intervals. In some embodiments, the fixation beam and the aiming beam on and off at fixed intervals.

As shown in FIG. 9, the intensity 912 of pulses 920 of light from the first light source such as the aiming beam can be turned on and off with period 922 with a duty cycle 924 over time 910. The intensity 922 of pulses 930 of light from the second light source such as the fixation beam can be turned on and off with period 932 with a duty cycle 934 over time 910. The combined cycle comprises a period 942 for each cycle. The duty cycle 924 and the duty cycle 934 can be varied to provide overlap in the illumination of the first light source and the second light source, such as the fixation beam and the aiming beam by increasing the duty cycle 924 or the duty cycle 934. The duty cycle 924 and the duty cycle 934 can be varied to provide gaps in the illumination of the fixation beam and the aiming beam by decreasing the duty cycle 924 or the duty cycle 934. In some embodiments, first light source and the second light source such as the fixation beam and the aiming beam are configured to overlap temporally, to provide spatial overlap of the Purkinje images and fixation beam in the images from the first optical path and the second optical path as described herein.

In some embodiments, the processor alternates between a first color of the fixation beam and a second color of the alignment beam to reduce fixation fatigue of the subject Although reference is made to the first light source and the second light source comprising the aiming beam and the fixation beam, in some embodiments, the first light source may comprise a first light color emitted from a display and the second light source may comprise a second color emitted, from a display, for example with both emitted from substantially the same location of the display.

Although reference is made to a series of light pulses provided to a subject, the stimulus provided to the subject can be provided in many ways and may comprise a continuously varying stimulus. For example, the first series of light pulses may comprise a portion of a sinusoidally varying signal and the second series of light pulses may comprise a second portion of a sinusoidally varying signal. The presently disclosed light pulses may comprise light pulses of a pulse width modulated signal or a pulse density modulated signal, in which the series of light pulses correspond to a time varying stimulus which is smoothed out to lower frequencies to appear continuously varying, for example.

Also, while reference is made to discrete light pulses, in some embodiments, the light pulses referred to in FIG. 9 may comprise a change in intensity of each light pulse, for example. For example, light pulses 920 may comprise an increase in intensity as at the locations shown in FIG. 9, although the pulses may remain on but with lesser intensity. Similarly, light pulses 920 may comprise an increase in intensity as at the locations shown in FIG. 9, although the pulses may remain on but with lesser intensity.

In some embodiments, a fixation beam comprises a target on a display at a substantially fixed location on the display In some embodiments, the target comprises a dot, for example.

In some embodiments, the fixation beam alternates between the first color and the second color at a substantially fixed location.

In some embodiments, the first pulses 920 and the second pulses 930 are interleaved.

In some embodiments, the second light pulses 930 appear inside the first light pulses as seen by the patient.

In some embodiments, the first light source such as the aiming beam generates a low contrast or slightly blurred image on retina.

In some embodiments, the second light source such as the fixation beam comprises a sharply defined, high-contrast fixation target.

In some embodiments, the switching between the first light pulse and the second light pulse over a switching cycle trains the one or more of the subject or the user's foveal fixation to converge precisely on the target by maximizing neural fixation engagement, improving repeatability, and increasing alignment sensitivity. In some embodiments, this alternating optical load amplifies the subjective distinction between correct and incorrect fixation, exploiting neural tuning for ultra-fine correction.

In some embodiments, abrupt transition from one color to another color creates the appearance of overlapping spots.

In some embodiments, the aiming beam overlaps spatially the fixation beam on one or more of the umbo of the subject or the cornea, and the region of overlap comprises intermittent or superimposed colors, such as a color intermediate to the first color and the second color. In some embodiments, the region of overlap is located on the umbo and the subject perceives the intermittent or superimposed colors, such as a color intermediate to the first color and the second color, at the same location for the fixation beam and the aiming beam. In some embodiments, the user perceives at the region of overlap from a microscope image, intermittent or superimposed colors, such as a color intermediate to the first color and the second color.

In some embodiments, the aiming beam is turned off while the fixation beam remains on to alter the illumination intensity of the one or more of the first beam or the second beam.

In some embodiments, the processor is configured to turn the aiming beam on and the fixation beam off during each of a plurality of cycles so as to provide an abrupt change in a color of the beam.

In some embodiments, the processor is configured to cycle one or more of the fixation beam or the alignment beam substantially on and substantially off at regular intervals to provide a perceived change in color of one or more of the fixation beam or the aiming beam to the subject.

In some embodiments, the processor is configured to provide an audio cue to the subject, the audio cue corresponding to a change in perceived color of one or more of the fixation beam.

FIGS. 10A, 10B and 10C show overlapping light pulses as seen by one or more of the user of the system or the subject under evaluation by the system such as a patient.

FIG. 10A shows a first light pulse of the first plurality of pulses 920.

FIG. 10B shows a second light pulse of the second plurality of pulses 930.

FIG. 10C shows a perceived combined light pulse at a spatially overlapping region 1010. The perceived combined light pulse comprise the first light pulse 920 and the second light pulse 930 overlapping spatially at a region 1010.

In some embodiments, the first light series of light pulses 920 do not overlap temporally with the second series of light pulses 930, although the pulses are perceived to overlap. The abrupt change in color pay provide a chrominance and a luminance cue to one or more of the user or the subject, for example.

In some embodiments, the plurality of pulses overlap spatially and temporally. The overlap can be provided based on the duty cycles of the first light source and the second light source. In some embodiments, the first light source comprises a continuous illumination with a 100% duty cycle, and the second light source comprises a duty cycle less than 100%.

Figure 11:
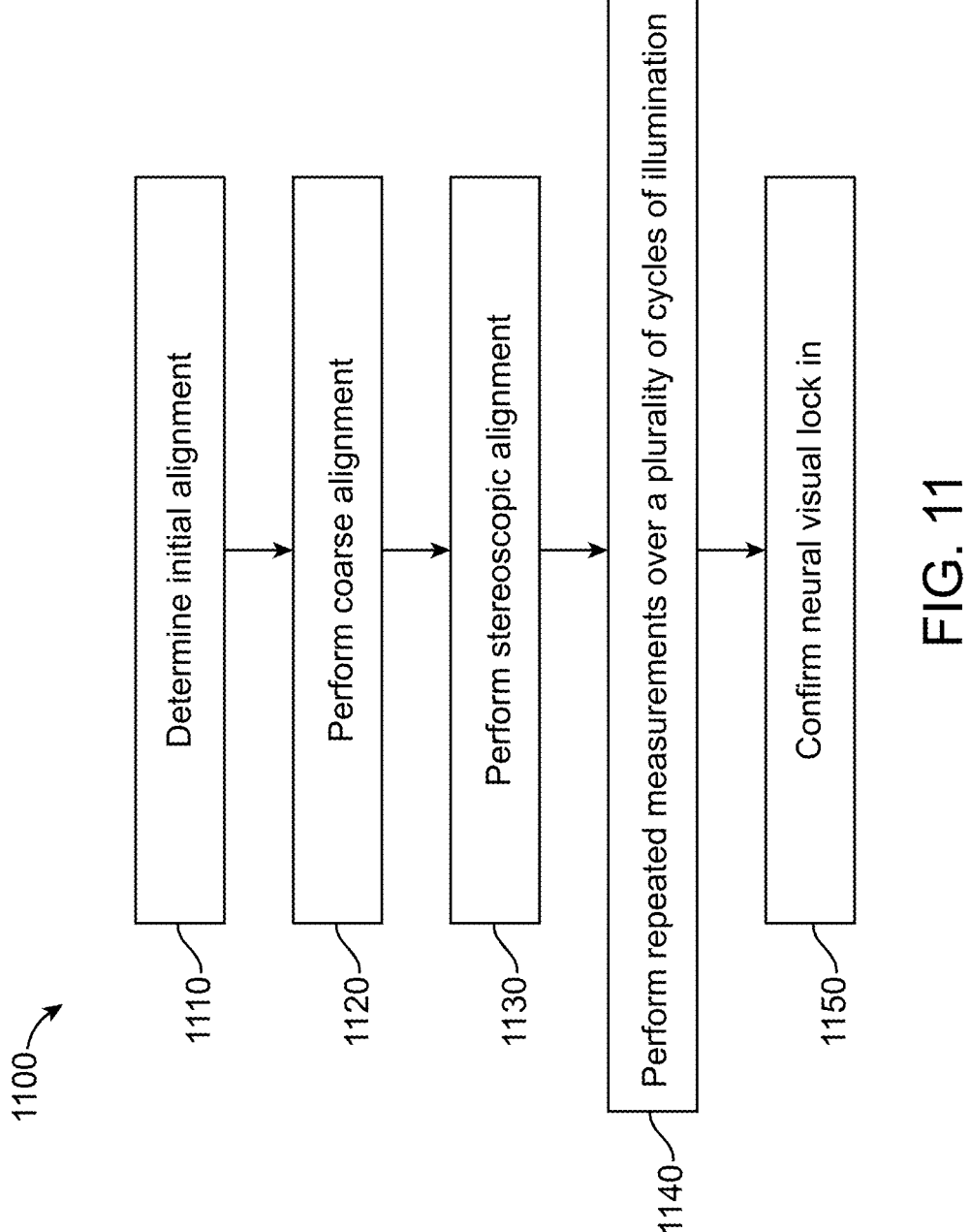
FIG. 11 shows a method of aligning an eye, in accordance with some embodiments.

FIG. 11 shows a method 1100 of aligning an eye with an instrument.

At a step 1110, an initial alignment is determined. The initial alignment can be determined from an image such as the image shown in FIG. 5A At a step 1120, coarse alignment is performed. The coarse alignment can be performed in accordance with FIG. 5B.

At a step 1130, stereoscopic alignment is performed. The stereoscopic alignment can be performed in accordance with any of FIGS. 5C to 7, for example.

At a step 1140, repeated measurements are performed over a plurality of cycles of illumination.

At a step 1150, neural visual lock in of the subject is confirmed. The neuro visual lock in of the subject can be confirmed in many ways. In some embodiments, fixation is measured at a plurality of illumination cycles and lock in is determined when the eye has moved no more than a threshold amount over each of the plurality of illumination cycles. Alternatively or in combination, the fixation of the eye can be measured at each of a plurality of cycles until neurovisual the movement of the eye converges toward stable fixation for a plurality of cycles, such as 10 cycles. In some embodiments, the stability of fixation is evaluated with one or more of a Root Mean Square (RMS) measurement of fixation, a power spectrum of eye movement, or a peak movement of the eye. In some embodiments, a neuro-visual lock-in is triggered in response to the stability of fixation.

In some embodiments, the processor is configured to determine the location of one or more of the location of the Purkinje image or the pupil, or the relative location of these ocular structures in response to the neurovisual lock in having been determined. The processor may store these values in a format for exporting to another instrument or for treatment of the subject. The above steps can be repeated with different illumination levels to provide determine the location of one or more of the location of the Purkinje image or the pupil, or the relative location of these ocular structures in response to the neurovisual lock in having been determined for each of a plurality of illumination levels, e.g. two or more of mesopic, photopic or scotopic illumination.

While the neurovisual lock of step 1150 can be confirmed in many ways, in some embodiments, the neurovisual lock in is determined with a plurality of measurements of the position of the eye. The positions of the eye can be measured in any way as described herein, for example with reference to one or more of vernier acuity from the parallax cameras, a location of the Purkinje image, first and second locations of the Purkinje image, a location of the pupil, or first and second locations of the pupil.

In some embodiments, the neurovisual lock in is determined with movement of the eye such as RMS movement of the eye lower than a threshold amount. In some embodiments, the processor is configured to cycle the fixation beam until a lock in has been achieved. In some embodiments, lock is achieved when the eye remains stable within a threshold amount over a plurality of cycles, for example stable over from 5 to 10 cycles of the fixation beam. Alternatively or in combination, statistical testing of a plurality of eye locations can be used to determine with statistical significance that the location of the eye has been locked in. In some embodiments, the lock in below a threshold amount is determined with a statistical significance of a p-value, such as a p-value of 0.05 or less, for example one or more of 0.01, 0.001, 0.0001, or 0.00001, for example. The threshold of eye movement associated with the lock in may comprise any suitable value such as 0.2 mm, 0.1 mm, 0.05 mm, 0.025 mm, or 0.010 mm, for example.

While statistical significance can be determined in many ways, in some embodiments statistical significance is determined with a geometric/binomial probability flow configured to determine a p-value from scatter of the distribution of eye locations. In some embodiments, a baseline scatter radius is determined, e.g. 1.0 mm (1000 micrometers), although other baseline radii may be used as described herein. Although reference is made to a geometric/binomial probability flow, one of ordinary skill in the art of statistics can develop other tests to determine when eye movement is below a threshold amount, in accordance with the present disclosure.

In some embodiments, a baseline scatter distribution is established with reference to a predetermined scatter radius. In some embodiments, the scatter radius may be set to approximately 1000 micrometers, although other values may be used depending on system calibration or application-specific parameters as described herein, such as 0.2 mm, 0.1 mm, 0.05 mm, 0.025 mm, or 0.010 mm. In some embodiments, the baseline scatter provides a reference spatial distribution against which subsequent probability calculations may be determined. In some embodiments, an area ratio is computed by comparing a zone of interest to the baseline scatter region. In some implementations, the probability p1 of an event occurring within the zone of interest may be expressed as a function of the ratio between the radius of the zone of interest and the radius of the baseline scatter, raised to an appropriate power corresponding to dimensionality. In some embodiments, this area ratio provides a normalized per-frame probability of occurrence within the zone of interest. In some embodiments, multiple frames are considered, and each frame provides an independent trial. In some embodiments, if k consecutive or otherwise relevant frames are observed within the zone of interest, the compounded probability of such an occurrence may be expressed as $p=(p1)^k$. In some embodiments, this compounded probability represents the likelihood of observing a clustered pattern within the zone under the null hypothesis of random scatter. In some embodiments, the compounded probability is interpreted as a p-value. In certain embodiments, the p-value represents the probability, under the null hypothesis, of obtaining a result at least as extreme as the observed clustering of frames. In some embodiments, the final p-value may be no more than $10^{-10}$, thereby providing statistical evidence that the observed clustering is highly unlikely to result from random chance alone. In some embodiments, the probability of random occurrence may be bounded by an upper limit, such as less than 0.0001, for example. In some embodiments, such bounds and estimates provide formal quantification of statistical significance, thereby supporting conclusions regarding non-random associations or clustering phenomena.

In some embodiments, the processor is configured to determine that fixation on the target has been entrained with the umbo, for example in response to movement of no more than approximately 0.05 mm, which corresponds approximately to 1/3 of the 0.150 mm size of the umbo. Referring back to FIG. 1, because the distance from the cornea to the first nodal point of the eye is approximately 1/3 of the distance from the second nodal point of the eye to the umbo, a 0.05 mm centration on the cornea corresponds to centration on the umbo of the eye, in accordance with some embodiments.

In some embodiments, the processor is configured to preform repeated measurements to determine the p value, for example 10, 20, 50 or 100 measurements of the eye, which can be performed in real time with the first parallax image and the second parallax image.

FIG. 12 shows a method 1200 of aligning an eye of a subject with an instrument. At a step 1210, the subject is placed on a support. At a step 1220, a fixation beam is directed toward an umbo of the eye, the fixation beam comprising a first color. At a step 1230, the subject is instructed to fixate on the fixation beam. At a step 1240, an aiming beam is directed to a cornea of the eye to a first location corresponding to a center of the pupil while the subject fixates on the fixation beam, the aiming beam comprising a second color different from the first color. At a step 1250, the aiming beam is moved to a second location aligned with a Purkinje image of the fixation beam, the second location being different from the first location. At a step 1260, an illumination intensity of one or more of the fixation beam or the aiming beam is altered to change a color perceived by the subject while the fixation beam is aligned with the aiming beam. At a step 1270, confirmation that the instrument is aligned with the umbo is obtained by asking the subject to confirm that the fixation beam and the aiming beam appear at a same location when the illumination intensity changes.

Figure 13:
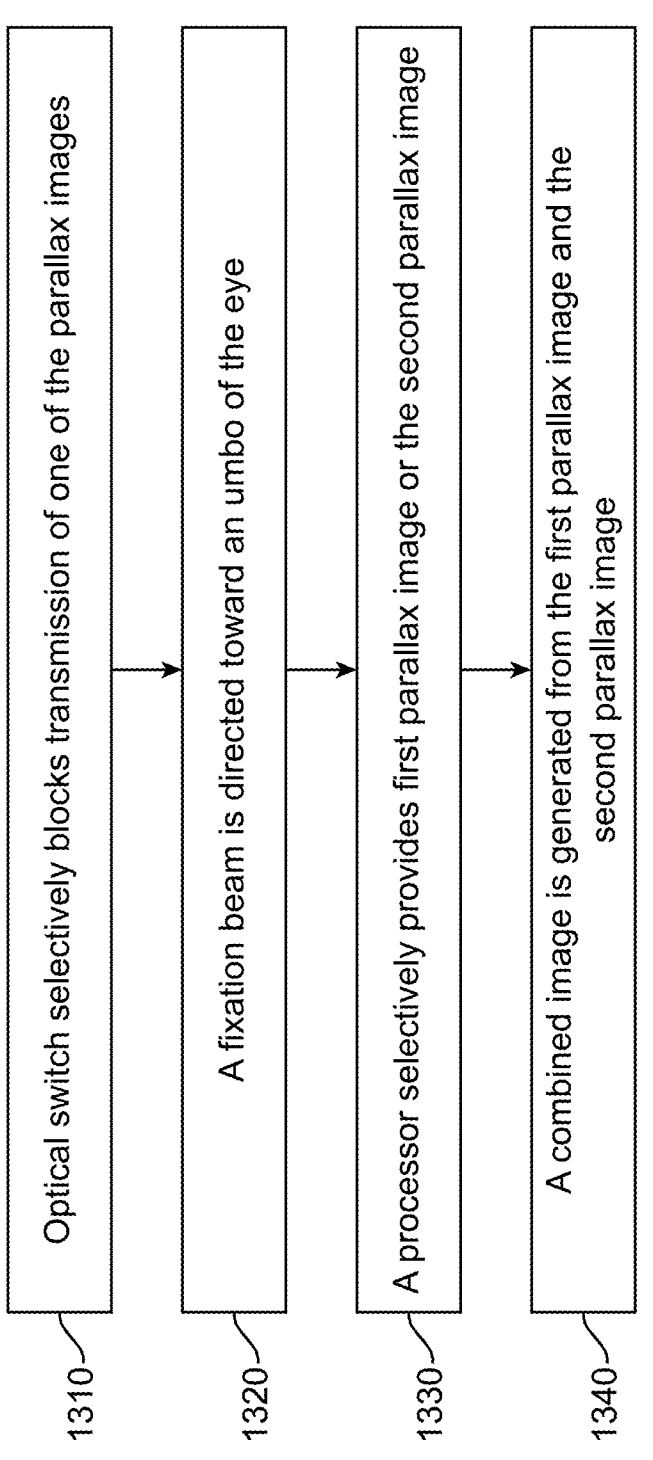
FIG. 13 shows a stereoscopic alignment method, in accordance with some embodiments.

FIG. 13 shows a stereoscopic alignment method 1300, in accordance with some embodiments. At a step 1310, an optical switch selectively blocks transmission of one of the parallax images. At a step 1320, a fixation beam is directed toward the umbo of the eye. At a step 1330, a processor is coupled to the optical switch to selectively provide the first parallax image to a first eye of a user or the second parallax image to a second eye of the user. At a step 1340, a combined image is generated from the first parallax image and the second parallax image, the combined image comprising one or more of a first Purkinje marker corresponding to a location of a Purkinje image in the first parallax image, a second Purkinje marker corresponding to a location of a Purkinje image in the second parallax image, and a marker corresponding to a centroid of the pupil.

Figure 14:
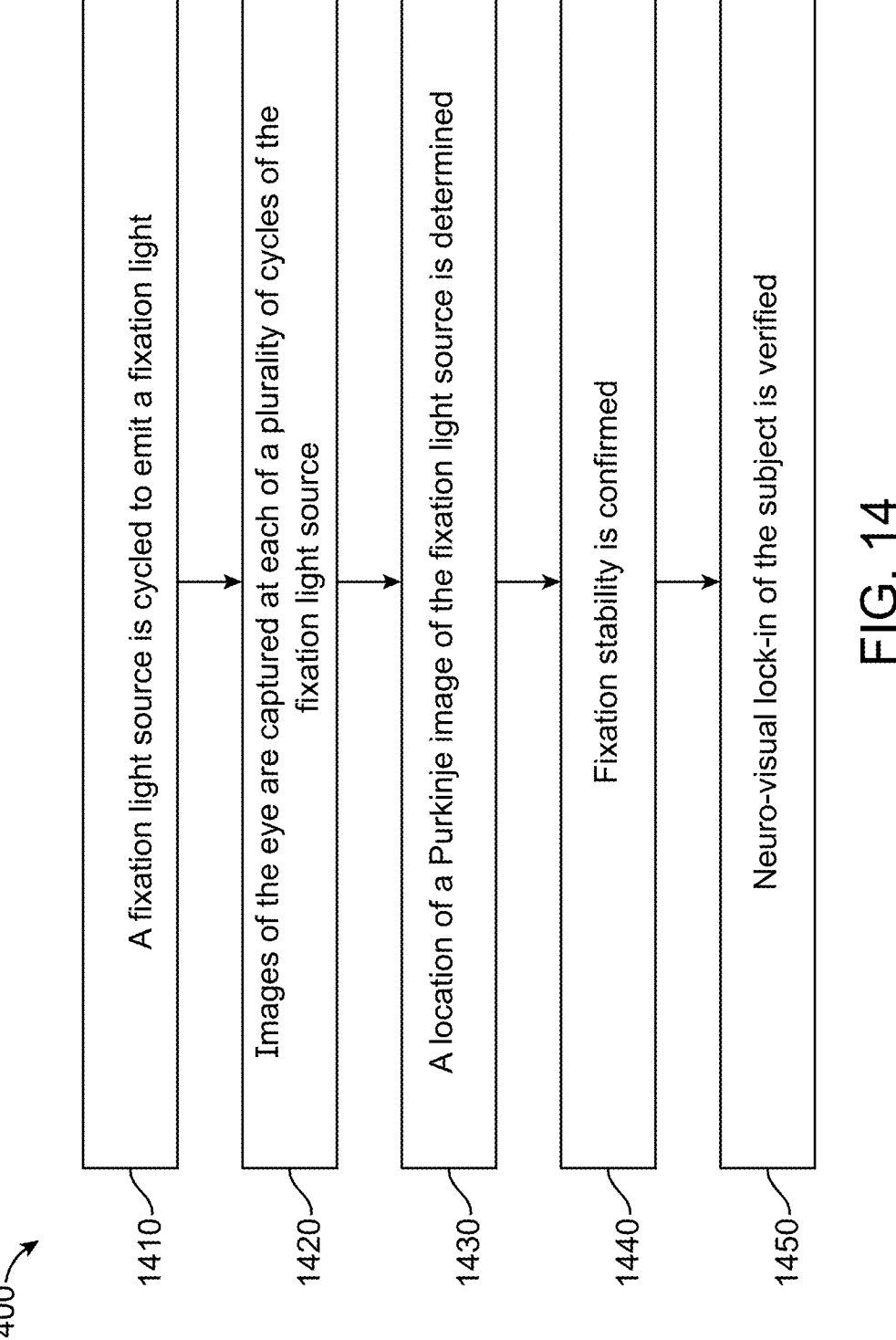
FIG. 14 shows a fixation verification method under cycling illumination, in accordance with some embodiments.

FIG. 14 shows fixation verification method 1400 under cycling illumination, in accordance with some embodiments. At a step 1410, a fixation light source is cycled to emit a fixation light beam along a fixation optical path toward the umbo of the eye, the fixation beam cycling between a first color and a second color at fixed intervals. At a step 1420, images of the eye are captured at each of a plurality of cycles of the fixation light source. At a step 1430, a location of a Purkinje image of the fixation light source is determined at each of the plurality of cycles to determine a stability of fixation of the eye. At a step 1440, fixation stability is confirmed by determining that the Purkinje image remains coincident with the aiming beam during color cycling. At a step 1450, neuro-visual lock-in of the subject is verified when movement of the eye converges toward stable fixation for a plurality of cycles.

In some embodiments, the processor is configured to cycle the color of the fixation beam in coordination with other processes. In some embodiments, the processor is configured to cycle the fixation beam between a first color and a second color different from the first color at fixed intervals. In some embodiments, the processor is configured to record the subject's fixation behavior during illumination with the first color and to move the aiming beam in response to a user input during illumination with the second color.

In some embodiments, is system is configured to track the eye in response to the location of the first view of the Purkinje image and the second location of the Purkinje image, in accordance with method 1400, for example. The fixation light source is configured to emit a fixation light beam along a fixation optical path toward an umbo of the eye. A parallax imaging system comprises a first camera coupled to a first parallax optical path and a second camera coupled to a second parallax optical path, in which the first parallax optical path is located on a first side of the fixation optical path to capture a first parallax image of the eye comprising a pupil of the eye, and a first reflection of the fixation light beam at a first location. The second parallax optical path is located on a second side of the fixation optical path to capture a second parallax image comprising the pupil, and a second reflection of the light beam at a second location. A processor is coupled to the parallax imaging system, the processor configured to track movement of a location of the eye in response to the first parallax image and the second parallax image.

The processor can be configured to determine and track the location of the eye with any suitable approach as described herein. In some embodiments, the processor is configured to track a location of the pupil to determine movement of the location, for example in response to the first image from the first parallax optical path and the second image from the second parallax optical path. In some embodiments, the processor is configured to track a location of the Purkinje image of determine the location of the eye, for example in response to the first image from the first parallax optical path and the second image from the second parallax optical path. In some embodiments, the processor is configured to track the location of the eye in response to the first image and the second image with triangulation as described herein, for example.

In some embodiments, wherein processor is configured to cycle the fixation beam between a first color and a second color different from the first color.

In some embodiments, the processor is configured to record a series of eye positions during one or more of a first duration of illumination with the first color or a second duration of illumination with the second color over a plurality of illumination cycles.

In some embodiments, the processor is configured to determine that the eye of the subject has locked onto the fixation beam with neurovisual fixation in response to the series of eye positions recorded over the plurality of illumination cycles.

In some embodiments, the processor is configured to offset a treatment beam in real time in response tracked positions of the eye.

In some embodiments a laser treatment system is configured to perform configured to treat the eye at only one of a plurality of colors of a fixation beam, for example.

In some embodiments, one or more steps of method 1400 is performed under varying illumination conditions, such as one or more of mesopic, photopic or scotopic illumination. In some embodiments, the processor is configured to determine an offset of the one or more of the Purkinje image or the aiming beam with mesopic illumination and photopic illumination, for example.

In some embodiments, the processor is configured to output a data file corresponding to a difference between a mesopic location of the one or more of Purkinje image or the aiming beam under mesopic illumination and a photopic location of the one or more of the Purkinje image or the aiming beam under photopic illumination, in order to center an optical therapy on the mesopic location of the one or more of the Purkinje image or the aiming beam under mesopic illumination when the eye is aligned to the photopic location under photopic illumination, for example. In some embodiments, the data file is output by a first system in a format configured to be read by a second system, for example. The location of the one or more of the Purkinje image, center of the pupil, or the aiming beam can be output in an XY coordinate system or a radial coordinate system, for example.

In some embodiments, the processor is configured to determine an offset of the one or more of the Purkinje image or the aiming beam with mesopic illumination and photopic illumination. The offsets of the output data can correspond XY coordinate system or a radial coordinate system, for example.

One or more steps of method 1400 can performed to determine changes in posture associated with changes in alignment. In some embodiments, the processor is configured to determine the change in cyclotorsion rotation in response to a rotational alignment between iris structure in a first image and the iris structure in a second image, for example.

In some embodiments, the processor is configured to determine a torsional angle of the eye with respect to an optical axis of the eye in response to an image of the iris, the image of the iris comprising one or more of the first parallax image, the second parallax image, the combined image, or an image from a coaxially aligned camera. In some embodiments, the processor is configured to measure the torsional angle and record whether the patient is seated or supine when the torsional angle has been measured. In some embodiments, the processor is configured to determine an offset of the torsional angle between seated and supine positions of the subject. In some embodiments, a change in cyclotorsion rotation of the eye is determined in response to alignment of a first image of an iris structure and a second image of the iris structure, in which the first image acquired before postural adjustment, and the second image acquired after postural adjustment.

In some embodiments, the processor is configured to output an offset of the torsional angle between seated and supine positions of the subject to a data file. The data file can be read with a second system, such as an optical therapy system, for example.

Figure 15:
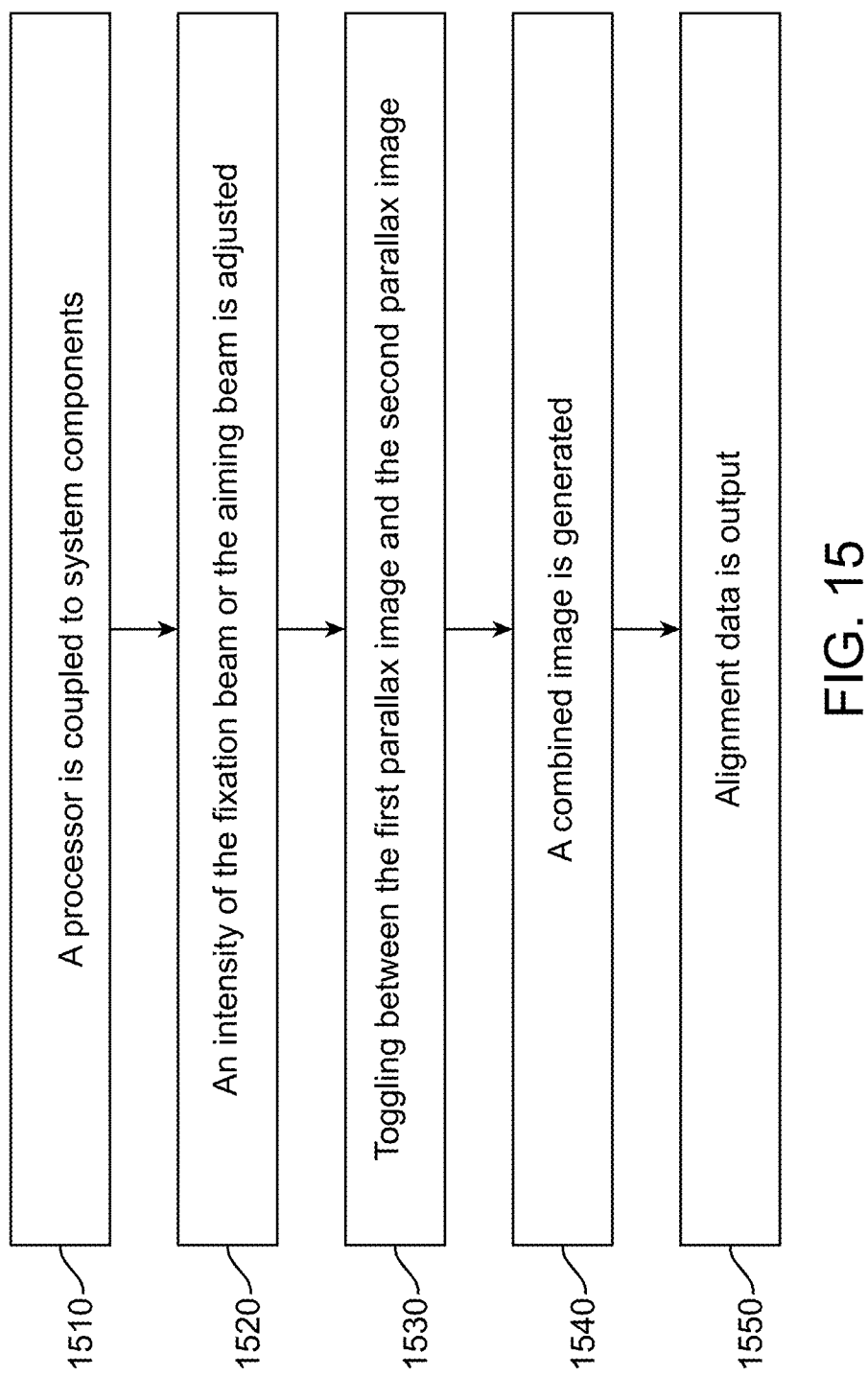
FIG. 15 shows a system-level control method, in accordance with some embodiments.

FIG. 15 shows a system-level control method 1500, in accordance with some embodiments. At a step 1510, a processor is coupled to a stereo microscope, a fixation beam source, an aiming beam source, and an optical switch. At a step 1520, an intensity of the fixation beam and the aiming beam is controlled to adjust a color perceived by the subject. At a step 1530, toggling between the first parallax image and the second parallax image is performed with the optical switch at a frequency within a range from about 0.25 Hz to about 5 Hz and optionally within a range from about 0.5 Hz to about 2 Hz. At a step 1540, a combined image is generated comprising the aiming beam, a first reflection of the fixation beam, a second reflection of the fixation beam, and a centroid of the pupil. At a step 1550, alignment data comprising a relative offset between the aiming beam and the Purkinje reflections is output.

FIG. 16 shows a triangulation method 1600, in accordance with some embodiments. At a step 1610, a first parallax image and a second parallax image of the eye are captured, the first parallax image and the second parallax image each comprising the pupil and a Purkinje image of the fixation beam. At a step 1620, the Purkinje image in the first parallax image and the second parallax image is identified. At a step 1630, the location of the Purkinje image is triangulated in response to the separation distance between a first entrance pupil of the first parallax optical path and a second entrance pupil of the second parallax optical path. At a step 1640, a centroid of the pupil is determined in each of the first parallax image and the second parallax image. At a step 1650, a relative offset between the triangulated Purkinje image and the centroid of the pupil is determined. At a step 1660, alignment coordinates comprising the relative offset for surgical alignment or planning are output.

Figure 17:
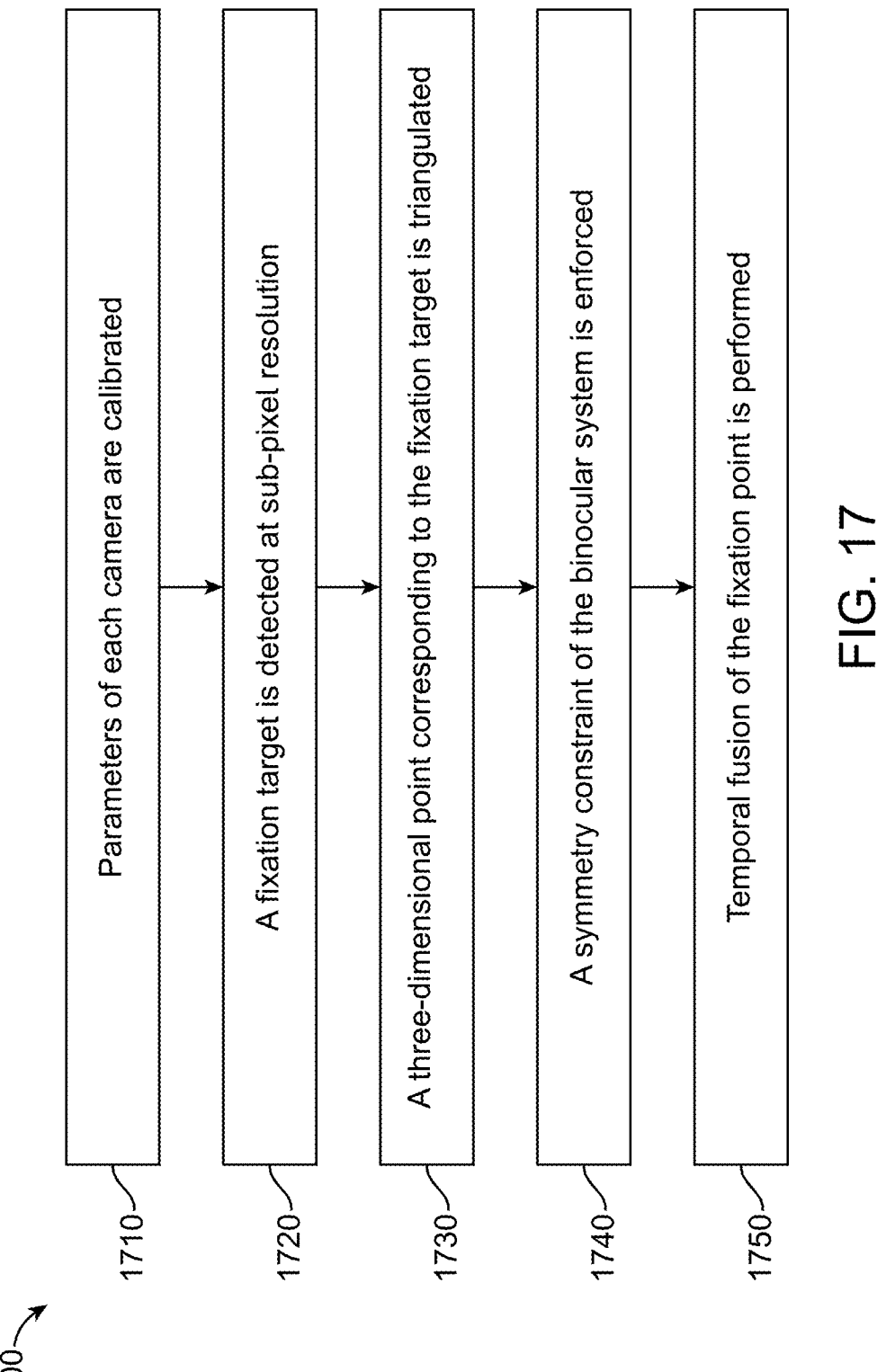
FIG. 17 shows a method of determining a fixation point with a binocular imaging system, in accordance with some embodiments.

FIG. 17 shows a method 1700 of determining a fixation point with a parallax imaging system, such as a binocular imaging system, in accordance with some embodiments.

At a step 1710, intrinsic parameters of each camera are calibrated, extrinsic parameters of the stereo rig geometry are determined, and a time synchronization between the cameras is established with a hardware trigger and a shared clock, wherein rolling-shutter effects are corrected if needed.

At a step 1720, a fixation target is detected at sub-pixel resolution, wherein the fixation target comprises a bright pulsing dot, the dot is detected with a blob detector, a cropped region is fit with a two-dimensional Gaussian function, and the localization is refined to within a fraction of a pixel. In some embodiments, a convolutional neural network detector is applied as an additional measure, and tracking between frames is performed with an optical flow algorithm with periodic re-locking via the Gaussian fit.

At a step 1730, a three-dimensional point corresponding to the fixation target is triangulated, wherein projection matrices are built from the intrinsic and extrinsic parameters, an initial triangulation is performed with a direct linear transform algorithm, and the triangulation is refined by minimizing a reprojection error with an iterative solver.

At a step 1740, a symmetry constraint of the binocular system is enforced, wherein cameras oriented at equal and opposite angles about a midline are constrained with a cost function that penalizes deviations from angular symmetry, thereby stabilizing the solution and providing a lock metric.

At a step 1750, temporal fusion of the fixation point is performed, wherein a Kalman filter is applied to the triangulated three-dimensional point, updates are accepted during designated intervals, prior state is maintained during other intervals, and an output is generated comprising the fixation point, a per-frame reprojection error, a symmetry residual, and a confidence metric.

In some embodiments, a system can be configured to implement a triangulation method such as method 1700. A light source is configured to emit a fixation light beam toward an umbo of the eye along a fixation optical path. A parallax imaging system comprises a first parallax optical path and a second parallax optical path, the first parallax optical path on a first side of the fixation optical path to capture a first parallax image of the eye, the first parallax image comprising a pupil of the eye and a Purkinje image of the fixation light beam, the second parallax optical path located on a second side of the fixation optical path to capture a second parallax image of the eye, the second parallax image comprising the pupil and the Purkinje image. A processor is coupled to the parallax imaging system, the processor configured to determine a location of the Purkinje image in response to the first parallax image and the second parallax image.

In some embodiments, the processor is configured to output a point corresponding to a location of the Purkinje image and a second point corresponding to a location of a center of the pupil in response to the first parallax image and the second parallax image.

In some embodiments, the processor is configured to output a map comprising a first marker corresponding to the location of the Purkinje image and second marker corresponding to the location of a center of the pupil and optionally wherein map comprises a circular marker corresponding to a boundary between an iris and the pupil.

In some embodiments, the processor is configured to triangulate the location of the Purkinje image in response to a first location of the Purkinje image in the first parallax image and a second location of the Purkinje image in the second parallax image in order to determine the location of the Purkinje image.

In some embodiments, the processor is configured to triangulate the location of the pupil in response to a first location of the pupil in the first parallax image and a second location of the pupil in the second parallax image in order to determine the location of the pupil.

In some embodiments, the processor is configured to triangulate the Purkinje image in accordance with a triangle extending between a first entrance pupil of the first parallax optical path and a second entrance pupil of the second parallax imaging path, in which a vertex of the triangle corresponds to the location of the Purkinje image.

In some embodiments, the processor is configured to triangulate the pupil in accordance with a triangle extending between a first entrance pupil of the first parallax optical path and a second entrance pupil of the second parallax imaging path, in which a vertex of the triangle corresponds to the location of the pupil.

In some embodiments, the processor is configured to determine a location of the Purkinje image relative to a location of the pupil in response to the first parallax image and the second parallax image.

In some embodiments, the processor is configured to determine a first location of the Purkinje image relative to the pupil in the first parallax image and a second location of the Purkinje image relative to the pupil in the second parallax image and determine the location of the Purkinje image relative to the pupil in response to the first relative position and the second relative position.

In some embodiments, the processor is configured to determine a centroid of the Purkinje image and a centroid of the pupil in the first parallax image to determine the first location of the Purkinje image relative to the pupil and to determine a centroid of the Purkinje image and a centroid of the pupil in the second parallax image to determine the second location of the Purkinje image relative to the pupil.

In some embodiments, the processor is configured to determine the location of the Purkinje image in response to a first location of the Purkinje image in the first parallax image and a second location of the Purkinje image in the second parallax image. In some embodiments, the first location corresponds to a first centroid of the Purkinje image in the first parallax image and the second location corresponds to a second centroid of the Purkinje image in the second parallax image.

In some embodiments, the processor is configured to determine the location of the pupil in response to a first location of the pupil in the first parallax image and a second location of the pupil in the second parallax image.

In some embodiments, the first location corresponds to a first centroid of the pupil in the first parallax image and the second location corresponds to a second centroid of the pupil in the second parallax image.

In some embodiments, the processor is configured to determine the location of the pupil and the Purkinje image in each of the first parallax image and the second parallax image with a trained Artificial Intelligence (AI) algorithm as described herein.

Figure 18:
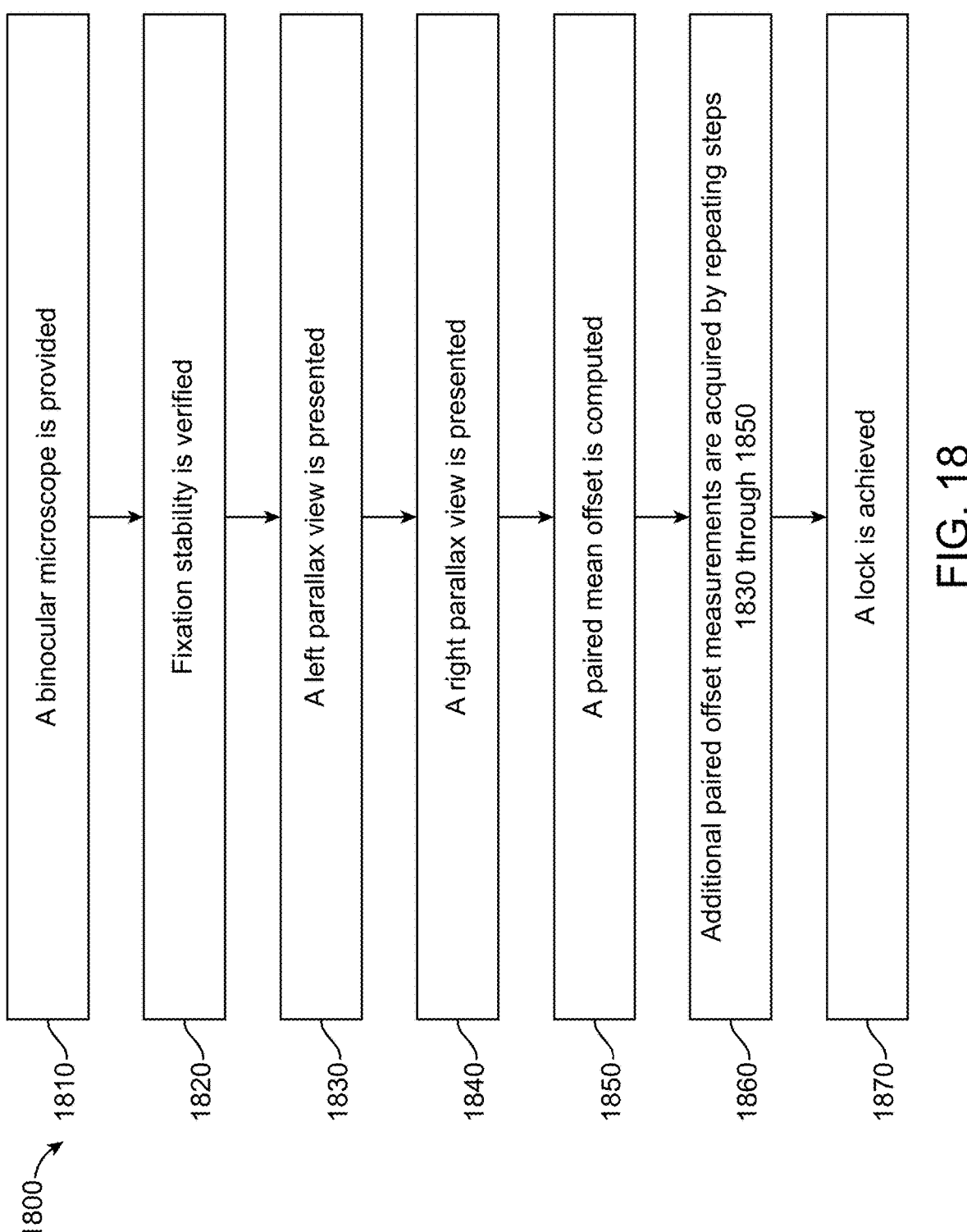
FIG. 18 shows a method of semi-automatic umbo alignment with alternating monocular parallax views, in accordance with some embodiments.

FIG. 18 shows a method 1800 of semi-automatic umbo alignment with alternating monocular parallax views.

At a step 1810, a binocular microscope is provided comprising a beam splitter and a fixation target displayed as a central pulsing dot with a surrounding ring, the fixation target being configured to alternate in a cadence of green illumination and red illumination. In some embodiments, a default cadence of three green intervals and one red interval at a frequency of about 0.5 Hz is applied, wherein the fixation target is displayed at a photopic luminance and a pupil centroid overlay is provided as a surrogate reference marker.

At a step 1820, fixation stability is verified during a green illumination interval, wherein a subject is instructed to maintain fixation on the green dot and a stability gate is applied to confirm a positional jitter of less than about 15 microns root-mean-square over a duration of about 300 milliseconds.

At a step 1830, a left parallax view is presented by closing the right ocular and activating the left optical path, wherein during a red illumination interval a centroid marker is nudged to contact an outer edge of the fixation ring at a rightmost location without overlap, thereby producing a right offset measurement that is stored as $R_1$.

At a step 1840, a right parallax view is presented by closing the left ocular and activating the right optical path, wherein during a red illumination interval the centroid marker is nudged to contact an outer edge of the fixation ring at a leftmost location without overlap, thereby producing a left offset measurement that is stored as $L_1$.

At a step 1850, a paired mean offset is computed, wherein the right offset and the left offset are averaged to form a vector mean $M_1$, the vector mean being displayed as a recentered reference marker while the fixation ring remains fixed.

At a step 1860, additional paired offset measurements are acquired by repeating steps 1830 through 1850, thereby forming successive means $M_2$, $M_3$, and so forth. Convergence is determined by applying a stop rule when a difference between successive means is less than about 15 microns across two consecutive pairs and a left-right residual asymmetry is less than about 10 microns.

At a step 1870, a lock is achieved by freezing a grand mean of the most recent paired offsets that satisfy the stop rule, wherein an umbo offset vector is output in device coordinates together with a confidence interval. In some embodiments such as laser eye surgery, a downstream treatment is gated to occur only during green intervals in which fixation stability criteria are satisfied.

Although FIGS. 11-18 show methods in accordance with some embodiments of the present disclosure, one of ordinary skill in the art will recognize adaptations and variations. The steps can be performed in any order. Some of the steps can be repeated and some of the steps removed. Some of the steps may comprise sub-steps of other steps. Any step of one of the methods can be combined with one or more steps of any other method.

A processor can be configured to perform any of the steps of methods 1100 to method 1800. In some embodiments, the processor is configured to automate one or more steps of method 1100 to method 1800.

In some embodiments, the processor is configured to determine a first distance between the first reflection and an aiming beam and a second distance between the second reflection and the aiming beam. In some embodiments, the processor is configured to adjust a position of the aiming beam in response to the first distance and the second distance. In some embodiments, the processor is configured to place the alignment beam between the first reflection and the second reflection in the combined image. In some embodiments, the processor is configured to direct an aiming beam toward a center of the pupil in response to the first parallax image and the second parallax image.

The processor can be configured with any suitable algorithm such as an artificial intelligence algorithm to perform one or more of the method steps as described herein. In some embodiments, the AI algorithm comprises one or more of a neural network, a convolutional neural network, for example. In some embodiments, the AI algorithm is configured to perform object detection, point localization, and image segmentation. In some embodiments, the AI algorithm is configured to perform detailed pixel-level segmentation, Mask R-CNN and the Segment Anything Model (SAM) are used to generate precise masks for objects. Clustering algorithms like K-means may also be used for image segmentation, grouping similar pixels into segments.

One of ordinary skill in the art in AI algorithms such as machine vision and object recognition can configure an AI algorithm to determine the location of objects as described herein, and can be used alternatively or in combination with a human user. In some embodiments a user interface is configured to provide an AI generated output, such as the location of one or more tissue structures, and to receive a user input confirming the location.

In some embodiments, the AI algorithm is configured to automatically align the aiming beam with the Purkinje image. In some embodiments, the user looks though the operating microscope to confirm that location of the aiming beam, for example with optical switching as described herein. Once the user is satisfied, the user can provide an input to the user interface, for example.

In some embodiments, a location of the umbo surrogate in relation to the pupil is determined with a first system, for example as shown with reference to FIGS. 2-4, and the location of the pupil with respect to the umbo surrogate is provided to a second system such as therapy device as described herein, for example as a laser vision correction system.

In some embodiments, the first system comprises a wavefront system which is used to determine a treatment profile, for example. In some embodiments, the wavefront is measured with reference to a center of a pupil. A center of a treatment profile of the laser can be aligned with a location of an umbo surrogate in response to the location of a center of a pupil.

In some embodiments, a location of an umbo surrogate is determined in relation to a center of a pupil and a center of a treatment profile of the laser is aligned with the location of the umbo surrogate in response to the location of the center of the pupil.

In some embodiments, the location of the umbo surrogate in relation to the center of the pupil has been provided by a separate diagnostic instrument, such as a wavefront system configured to align with an umbo surrogate as described herein.

In some embodiments, a location of an umbo surrogate under mesopic illumination is determined in relation to a center of a pupil under photopic illumination and a center of a treatment profile of the laser is aligned with the location of the umbo surrogate under scotopic or mesopic illumination in response to a center of a pupil under photopic illumination.

In some embodiments, the location of the umbo surrogate is determined in relation to a scotopic or mesopic pupil or a location of the limbus, for example with scotopic or mesopic illumination, and the location of the umbo surrogate under scotopic or mesopic illumination is determined with respect to a photopic pupil. The location of the umbo surrogate under scotopic illumination in relation to the photopic pupil may then be used to identify the location of the umbo surrogate under scotopic or mesopic illumination while the pupil is illuminated under photopic conditions, consistent with surgical treatment such as laser vision correction.

One of ordinary skill in the art will understand the amounts of illumination required for photopic, mesopic and scotopic illumination. For example, photopic vision corresponds to daylight vision, e.g. 10-100,000 lux and above. Mesopic vision may correspond to night viewing with illumination, such as street lights, parking lots, and can be within a range from 0.01 to 10 lux. Scotopic illumination is dominated by viewing with rods and may correspond to illumination within a range from 10-6 to 0.01 lux, for example.

Figure 19:
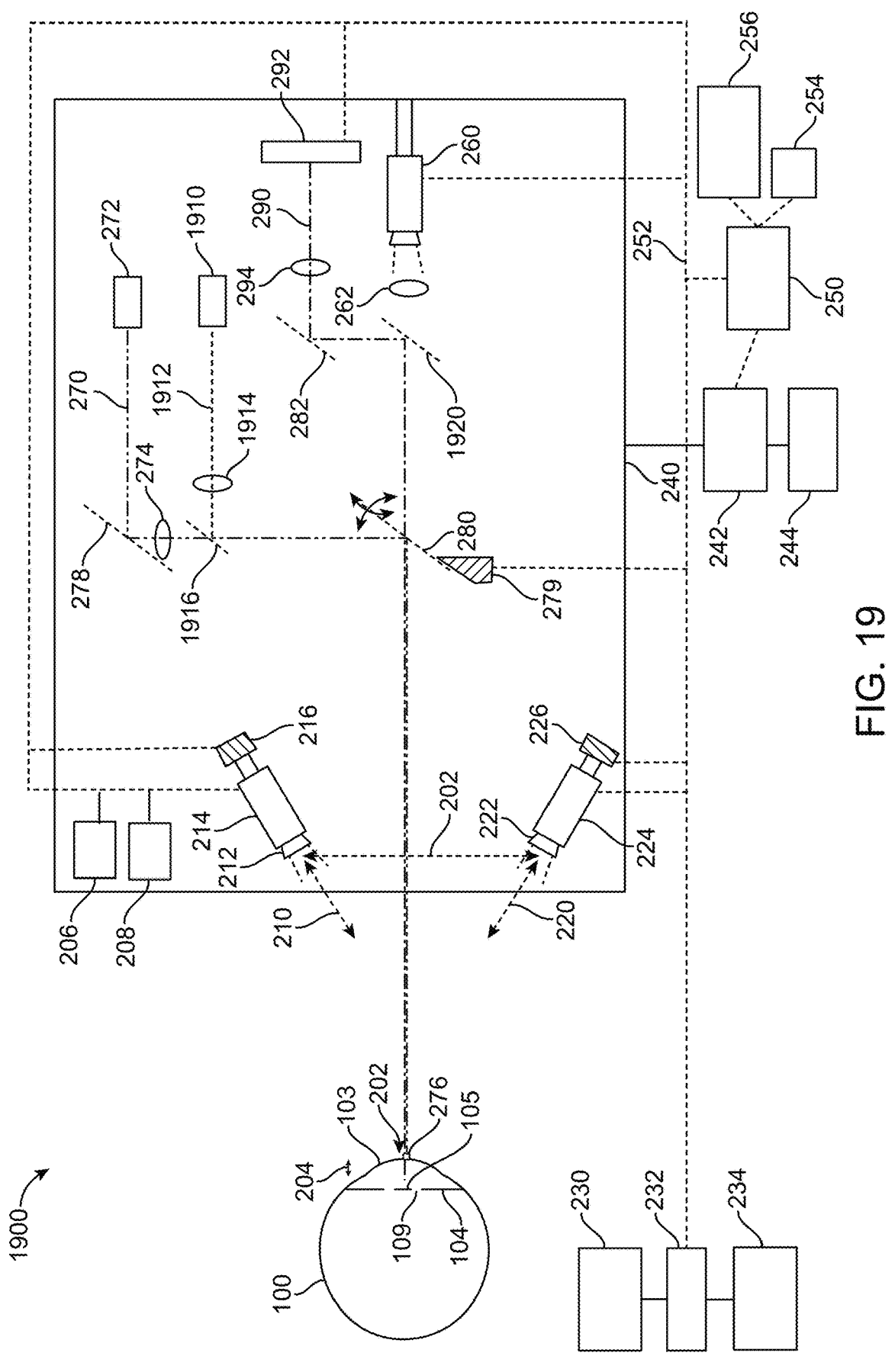
FIG. 19 shows a laser vision correction system, in accordance with some embodiments.

FIG. 19 shows a laser vision correction system 1900. The system 1900 may incorporate any of the features of the system 200 as described herein with reference to FIGS. 2 to 4, for example. Similar elements, structures, and features are shown with similar reference numbers and shall have a similar meaning as described herein with reference to FIGS. 2 and 3. Further, the system 1900 may incorporate any of the fixation, illumination, visual entrainment, alignment and methods as described herein, for example with reference to FIGS. 5A to 18.

A treatment laser 1910 is configured to generate a treatment beam 1912. The treatment beam may comprise any suitable treatment beam for any laser treatment as described herein, such as one or more of an excimer laser, a femtosecond laser, a picosecond laser, Yttrium Aluminum Garnet (YAG) laser, a Holmium: YAG laser, a frequency doubled laser, a diode laser, a solid state laser, or an infrared laser, for example. In some embodiments, the treatment beam 1912 is directed to a lens 1914 or other optical element such as a beam shaping optic or aperture, for example, so as to provide a suitable energy profile distribution at a target location on the eye 100, such as the cornea of the eye.

In some embodiments, a beam splitter 1916 is configured to combine the aiming beam and the treatment beam, for example. The combined aiming beam 270 and treatment beam 1912 are directed toward a movable beam splitter 280. The movable beamsplitter 280 is coupled to a scanner 279 under computer control as described herein. In some embodiments, the surface of the beam splitter is configured to reflect the aiming beam 270 and the treatment beam 1912 together, which can provide improved alignment in accordance with some embodiments. In some embodiments, the beam splitter 280 is configured to transmit the fixation beam 290 that is transmitted to the eye and IR light transmitted from the eye to camera 260, for example. In some embodiments, scanning of beam spitter 280 provides scanning of beam 270 and beam 1912 with only nominal nearly imperceptible displacement of the fixation beam 290 directed toward the eye and IR light directed to camera 260.

Although reference is made to beam splitter may comprise a plurality of beam splitters with dielectric coatings configured to reflect light of bandwidth within a range of about 10 nm to about 40 nm, and the beam splitters may comprise a stacked configuration with a plurality of reflective and transmissive optical paths. Additional beam splitters, optics, mirrors and actuators may be employed, as will be known by one of ordinary skill in the art of optical engineering.

In some embodiments, the fixation beam 290 and the fixation beam source 292 are configured to provide a plurality of colors, such as sequential, alternating or temporally overlapping colors or spatially overlapping colors. In some embodiments, the aiming beam is turned off, for example while the beam splitter 280 scans the treatment beam on the eye, and the fixation beam source 292 provides a plurality of colors as described herein.

While lens 294, fixation beam source 292 and fixation beam 290 can be configured in many ways, in some embodiments the lens 294, the source 292 and the beam 290 are configured to focus the fixation beam to a small spot on the cornea, and to provide an image of the source 292 in focus on the retina of the eye. In accordance with some embodiments, this can be enabled by passing a substantially collimated light beam through the fixation target and placing the target at a suitable distance from the fixation target so as to form an image of the fixation target on the retina.

Decreasing the size of the fixation beam 290 on the cornea can increase the depth of field of the fixation target on the retina, which can improve fixation. Alternatively or in combination, the fixation beam may comprise a collimated laser beam 290 for example. In some embodiments, the source 292 comprises a plurality of lasers emitting at different wavelengths and one or more beam splitters to provide illumination beam 290 with a plurality of colors. Alternatively or in combination, the source 292 may comprise a display or one or more LEDS and combinations thereof as described herein. In some embodiments, the fixation beam comprises one or more components of a Potentially Acuity Meter (PAM), previously manufactured by Mentor, for example.

In some embodiments, the aiming beam is configured similarly to focus the aiming beam onto the cornea to enable fixation with the aiming beam, and the aiming beam may comprise a fixation target as described herein, for example.

The laser vision correction system 1900 may comprise many elements of commercially available laser systems as will be understood by one of ordinary skill in the art. In some embodiments, system 1900 comprises a patient interface configured to couple to the eye of the patient. In some embodiments, the patient interface comprises a transparent concave surface to receive the cornea of the eye and couple to the eye with suction near a limbus of the eye.

In some embodiments, the fixation stimulus as described herein is used to align the eye with a femto second laser, for example with visual entrainment, and the eye is coupled to the patient interface with suction in response to stability of the visually fixated eye. Once the eye has been coupled to the patient interface, the treatment center can be determined. In a SMILE or similar procedure, the center of the lenticule can be located, e.g. centered, on the umbo surrogate as described herein. In some embodiments, the issue treatment profile is centered on the umbo surrogate in response to a location of a pupil of the eye, for example based on offset data between a location of a center of the pupil and the umbo surrogate.

In some embodiments, a low-suction mode allows micro-adjustment of the ring until software confirms the ring center coincides with the UMBO surrogate coordinate. Once aligned, full suction is applied. This can produce retinal surrogate based centration rather than corneal-surrogate alignment, improving accuracy. In some embodiments, the system is platform-agnostic and requires no modification of femtosecond optics, making it compatible with SMILE, SILK, PKP, and LASIK platforms, for example.

In some embodiments, the laser system comprises a fixation ring system of a femtosecond laser patient interface. In some embodiments, the fixation ring system comprises a low-suction positioning state, and a display or feedback interface showing the difference between ring center and the umbo surrogate based $\Delta X, \Delta Y$ coordinate. In some embodiments, a micro-adjustment mechanism is operable by surgeon or automated actuators to bring the eye into alignment. In some embodiments, the fixation stimulus is provided as described herein. In some embodiments, the fixation stimulus comprises a first color and a second color as described herein. In some embodiments, the fixation stimulus is configured to decrease saccades as described herein. In some embodiments, the system is configured to lock onto the to the patient's foveolar umbo surrogate before suction is applied.

Laser Treatment Control

Work in relation to the present disclosure suggest that eye motion may comprise a first slow drift component and a second fast component. The first drift component may be related to one or more of head tilt or rotation, respiratory movement, accommodative micro-motions, or slow pursuit, for example. In some embodiments, the eye tracker comprises a latency which is sufficiently short to allow the treatment spot to be offset in accordance with the eye movement. The second component may comprises saccades, for example. Saccadic eye movement may comprise one or more of ballistic movement, high peak velocity and acceleration, duration of typically 20-60 milliseconds. In some embodiments, the tracker comprises a latency with does not allow the offset laser beam to accurately catch up with the mid-saccade path of the eye.

In some embodiments, the laser firing control uses one or more of binary gating to enforce safety, predictive estimation to compensate for latency, explicit rejection of firing during high-velocity eye motion, or real time based stability before resuming laser operation.

In some embodiments, the system uses binary gating to enforce safety predictive estimation to compensate for latency, explicitly rejects treatment during high-velocity eye motion, requires time-based stability before resuming laser emission.

Figure 20:
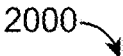
FIG. 20 shows a method of controlling laser beam firing in response to eye movement data, in accordance with some embodiments.

FIG. 20 shows a method 2000 of controlling laser beam firing of a laser vision correction procedure in response to eye movement data.

In some embodiments method 2000 comprises: determining a retinal visual-axis origin (umbo) proxy at the corneal plane; computing a real-time control signal that maintains a planned treatment origin within a predetermined threshold of said proxy (e.g. $\leq 10$ µm RMS); inhibiting laser emission outside time-gated fixation windows; and predicting residual ocular motion over a controller latency $\tau$ to pre-compensate beam position. In some embodiments, tracking error is reported in microns relative to the umbo proxy rather than pupil centroid.

In some embodiments, the eye is aligned with parallax-induced Vernier acuity using alternating monocular views as described herein.

In some embodiments, the treatment zone is offset in relation to a location of a pupil center such as a centroid as described herein.

In some embodiments, a color of a fixation target varies between a first color and a second color with a cadence. In some embodiments, the fixation target transitions between red and green with cadence, e.g. timing.

At a step 2010 a fixation stimulus is provided. The stimulus may comprise a stimulus with varying color as described herein. In some embodiments, the stimulus is configured to decrease saccadic eye movement as described herein. In some embodiments, the stimulus comprises a chromatic cadence. For example, the stimulus can be configured to alternate between green and red at ~0.5 Hz. In some embodiments, the luminance of one color fades to maintain attention. Work in relation to the present disclosure suggests that this chromatic cadence may decrease saccades, such as exploratory micro saccades to look for the stimulus.

In some embodiments, the second stimulus appears inside the first stimulus. Alternatively, the first stimulus may appear inside the second stimulus, for example.

In some embodiments, the variable color fixation stimulus is focused to a spot on the cornea to increase a depth of field of the variable color fixation stimulus.

In some embodiments, the second color is imposed on the first color with a fixed frequency and a duty cycle that varies. Alternatively, the second color is imposed on the first color with a variable frequency and a duty cycle that varies.

In some embodiments, the first color has a first frequency of illumination and the second color has a second frequency of illumination. In some embodiments the first frequency and the second frequency are substantially the same. Alternatively the first frequency and the second frequency can be different.

At a step 2020 fixation is evaluated.

In some embodiments, a stability of fixation of the eye is evaluated while the variable color fixation stimulus is provided to the eye.

In some embodiments, the fixation is evaluated while the fixation stimulus provides one or more cues to the patient, such as a variable duty cycle fixation light as described herein. Alternatively or in combination, the physician may provide cues to the subject, such as instructions to the patient on what they will see and how to fixation. In some embodiments, the fixation is evaluated in response to patient comments, such as the fixation light remaining stable and not being offset during changes in color.

In some embodiments, the stability of fixation of the is evaluated in response to the change in the color of the fixation stimulus for each of a plurality of cycles of the color of the fixation stimulus.

In some embodiments, the stability of fixation of the eye does not include eye movement data for a period of time after a change in the color of the fixation stimulus.

In some embodiments, the stability of fixation the eye is used to determine a tolerance of eye movement of a gate. In some embodiments, this tolerance comprises a customized tolerance determined based on the patients fixation in situ under the laser system prior to treating the patient. Work in relation to the present disclosure suggests that this approach can provide improved accuracy by providing a custom eye motion tolerance specific to each patient.

In some embodiments, the fixation is evaluated with a confirmation lock. In some embodiments, the confirmation lock provides a stimulus to the patient. In some embodiments, during Fixation-ON, the fixation dot briefly alters, e.g. "snaps" only when the controller detects $\|U_c-\hat{U}_c\| \le T$ for dwell D. This gives the patient a sensory confirmation they are aligned with the stimulus, which can be helpful in reducing exploratory saccades. In some embodiments, the change in the stimulus may appear as a brief change, similar to a snap, with one or more of a size variation, a halo, or a micro-change, for example.

In some embodiments, the fixation is evaluated prior to alignment with the umbo surrogate and during the laser treatment, for example.

At a step 2030 the eye is aligned with the laser system. The eye can be aligned with the laser system in any suitable way as described herein. In some embodiments, the eye is aligned with a parallax-assisted surgeon view. In some embodiments, alternating binocular views create a known stereo divergence, which can help the surgeon achieves dual-Vernier symmetry, with a human-in-the-loop confirmation that the system really is on the umbo surrogate at the cornea, $U_c$.

In some embodiments, the patient is provided with feedback during the alignment phase. In some embodiments, the patient is informed that their fixation is acceptable. Alternatively or in combination, the physician may tell the patient that they can relax because an eye tracker will track their eye movements. In some embodiments, prior or at the start of ablation, the subject is made aware the laser system identifies the exact spot where the subject's eye is located just prior to treatment, which can help to relax the subject, e.g. the patient. In some embodiments, the patient is informed that eye tracker is guiding the treatment to the correct location, which can help the subject relax.

At a step 2050, laser treatment is initiated. In some embodiments, the laser treatment is initiated in response to a user input such as a surgeon depressing a foot pedal, for example.

In some embodiments, the fixation target cycles through the substantially the same cycles of illumination as performed with step 2010. In some embodiments, throughout the ablation there is a repeated cycling of a constantly flashing fixation point with the fixation stimulus having a unique sequence of illumination cycles between colors at specific timing as described herein. In some embodiments, the fixation stimulus alternates or is continuous present with a first color, while a second color is coaxial and with the first color located at a center of the first color and has its own cycling frequency, as perceived by the eye of the subject, e.g. the patient.

At a step 2060, a firing gate is evaluated. In some embodiments, the firing gate is responsive to saccadic movement of the eye.

In some embodiments, the firing gate of the laser is evaluated in response to the position of the eye, wherein the gate is configured to inhibit firing of the laser in response to a saccade and to allow the laser to treat the eye in response to an absence of a detected saccade.

In some embodiments, the gate is configured to inhibit firing associated with a change in color of the fixation stimulus.

In some embodiments, the gate is configured to inhibit firing of the laser for a period of time after a change in the color of the fixation stimulus.

In some embodiments, a fixation of the eye is evaluated and the gate is configured to allow treatment in response to eye movement below a threshold amount and to inhibit treatment in response to eye movement above a threshold value.

In some embodiments, the threshold value is determined in response to eye movement data of the eye during a fixation evaluation prior to firing the laser.

In some embodiments, the planned origin is $U_c(t)$, which is the umbo proxy mapped to the corneal plane as described herein. In some embodiments, the measured surrogate is $S_c(t)$, which may be located at one or more of the pupil, the limbus or the vertex, and the beam command is $B_c(t)$.

In some embodiments, a firing gate is defined as $G(t) \in \{0,1\}$ such that the laser only emits when fixation, e.g. entrainment, is detected and no saccade is present detected. In some embodiments, the laser only emits when $G(t)=1$, for example when:

A. Fixation-ON state is confirmed such as with fixation stability and neurovisual lock-in as described herein; AND B. $\| U_c(t)-\hat{U}_c(t-\tau)\| \le T$ with $\tau$ the end-to-end latency and T is a threshold (e.g., 10-20 μm at cornea). In some embodiments, the end-to-end latency, r, refers to an amount time for the system to measure the eye position and adjust the laser beam position in response to the position of the eye in a closed loop configuration.

In some embodiments, during Fixation=OFF or when a saccade detector triggers (e.g. velocity/acceleration above threshold or), the parameter set $G(t)=0$ and the laser treatment pauses. One of ordinary skill in the art of eye tracking will know suitable parameters to use to detect a saccade. In some embodiments a saccade is detected when the eye moves above a threshold amount between successive video frames, for example when a centroid of the pupil moves above a threshold amount between successive video frames.

At a step 2070, a predictor for residual latency is utilized. In some embodiments, the predictor comprises a predictor to compensate for residual latency.

In some embodiments, a future position of the eye is predicted in the response to the position of the eye, and a position of the laser treatment is adjusted in response to the predicted future position.

In some embodiments, a closed loop eye tracking system has a latency and the future position is predicted in response to the position of the eye and the latency.

In some embodiments, the predictor is a bounded predictor such as (e.g., $\alpha$-$\beta$-$\gamma$ or Kalman with anatomical priors) on $U_c(t)$ to synthesize $\tilde{U}_c(t+\tau)$.

In some embodiments, this predictor is related to the state of G(t), for example command $B_c(t)=\tilde{U}_c(t+\tau)$only when G(t)=1.

In some embodiments, this use of the predictor handles drift, e.g. low frequency eye movements, while not chasing saccades.

At a step 2075 the laser beam position is adjusted and the tissue treated in accordance with the updated position.

In some embodiments, a scanner is configured to offset the laser beam in response to movement of the eye in response to the absence of a saccade.

In some embodiments, the scanner is configured to maintain a position of the scanner in response to a detected saccade.

At a step 2080, the system relocks on the umbo surrogate.

In some embodiments, a laser treatment profile is centered on an umbo surrogate prior to the gate inhibiting firing of the laser, and the laser system is realigned with the umbo surrogate after the gate inhibits firing of the laser. Work in relation to the present disclosure this step of realignment with the umbo surrogate, e.g. re-locking, may be helpful in reducing errors in some instances.

In some embodiments, after a detected saccade or cadence reset, instead of following Sc(t), the surrogate is re-established. In other words, the system does not follow the previously established Sc (t).

In some embodiments, the parallax/Vernier routine as described herein is used to reacquire $U_c$ (for example edge-kiss symmetry). In some embodiments, once the umbo surrogate has been established, the gate is reopened and G(t)=1. In some embodiments, the gate is opened if $\| U_c-\hat{U}_c\| \leq T$ for a dwell time D(e.g., 100-300 ms).

At a step 2090 the treatment resumes.

Referring again to step 2010, in some embodiments, the fixation stimulus comprises a dynamically varying stimulus to entrain fixation of the eye.

In some embodiments, the variable color fixation stimulus transitions from the first color to the second color with a frequency. In some embodiments, the frequency comprises a variable frequency. In some embodiments, the variable frequency comprises a first frequency at a first time and a second frequency at a second time, the second frequency slower than the first frequency.

In some embodiments, the frequency comprises a frequency of a chromatic cadence. In some embodiments, the chromatic cadence comprises a duty cycle of the second color, a frequency of the second color and a timing of the second color overlaid on the first color, for example.

In some embodiments, the first color comprises a first duty cycle and the second color comprises a second duty cycle and wherein one or more of the first duty cycle or the second duty cycle varies.

In some embodiments, the first duty cycle remains substantially fixed and the second duty cycle decreases. In some embodiments, the first duty cycle remains substantially fixed at 100% and the second duty cycle varies to less than 50%.

While the fixation stimulus can be provided in many ways, in some embodiments the second color is superimposed on the first color.

In some embodiments, a dynamic cadence is used to entrain fixation of the eye. In some embodiments, the dynamic cadence comprises a progressive ON-phase elongation, for example.

In some embodiments, after an initial fixation acquisition, the system no longer maintains a fixed frequency or duty cycle of the stimulus, such as a fixed red Purkinje cue at a fixed 1.5 Hz. In some embodiments, the system adapts the ON/OFF cycle as the patient's fixation becomes stable, for example by increasing or decreasing the duty cycle of one or more of the light sources. Work in relation to the present disclosure suggests that this may progressively entrain the oculomotor system, decreasing micro-saccades over time. Alternatively or in combination, this may increase treatment efficiency, by spending less time in OFF (non-ablation) phases once fixation has been determined to be stable, for example.

In some embodiments, the fixation cadence comprises a first substantially constant illumination with a first color, e.g. green, overlaid with a second color, e.g. red with an ON/OFF cycle that evolves over time. In some embodiments, there is a progressive ON-phase elongation and a progress OFF-phase shortening. In some embodiments, there is a gating window around each transition (e.g. $\pm\tau=2$ ms). In some embodiments, the gating window inhibits firing of the laser around each transition. In some embodiments, there is a saccade responsive blanking and dwell confirmation. In some embodiments, the fixation target transitions to a steady state substantially continuous mode.

TABLE 1

| | | | |
|---|---|---|---|
| Variable cadence of the fixation target/stimulus. | | | |
| Phase | Purpose | Typical cadence | Description/ behavior |
| Phase I— Entrainment | Teach the eye exactly where to look | 1.5 Hz (ON ≈ 330 ms/ OFF ≈ 330 ms) | Green fixation constant; red Purkinje cue flashes over it for ~5 cycles. System measures fixation repeatability and establishes the umbo proxy. |
| Phase II— Transition | Begin treatment, maintain saccade suppression | 1.0 Hz (ON ≈ 500 ms/ OFF ≈ 500 ms) | Laser tracking continues, but ablation is only allowed during ON segments; OFF intervals ensure predictive re-lock between pulses. |
| Phase III— Progressive extension | Efficiency increase without loss of control | ON duration gradually increases (e.g., 600 → 900 → 1200 ms), OFF shrinks correspondingly | Controller monitors fixation variance. As variance ≤ threshold for N cycles, ON window elongates automatically; OFF = blanking window + τ + safety margin. |

TABLE 1-continued

Variable cadence of the fixation target/stimulus.

| Phase | Purpose | Typical cadence | Description/ behavior |
|---|---|---|---|
| Phase IV— Continuous or micro- blanked mode | Fully stabilized phase | ON ≈ continuous; OFF ≈ 2 ms blank per τ | Once fixation RMS ≤ 10 μm @ cornea, system holds steady laser ON, inserting only the latency- covering blank per τ between micro- segments. |

In some embodiments, a fixation and emission control method comprises an intermittent luminous cue that is initially cycled at a first frequency to establish ocular fixation, and the duration of its ON state is progressively increased, while OFF intervals are proportionally shortened, in response to detected fixation stability below a defined positional variance threshold; during all OFF intervals laser emission is inhibited, and during ON intervals emission is permitted only when instantaneous corneal-plane error is ≤T μm for a dwell D, for example. In some embodiments, the fixation tolerance T is within a range from about 10 μm to about 25 μm, for example. In some embodiments, the dwell time D comprises about 300 ms, for example. In other words, the fixation is set to ON if the fixation is stable, e.g. less than T, for 300 ms, for example. In some embodiments, the Tolerance T comprises an RMS value of the eye position, for example.

In some embodiments, fixation is evaluated at times away from a change in color of the of the fixation stimulus to reduce the influence of saccadic eye movement, which may be related to changes in color of the fixation stimulus. Work in relation to the present disclosure suggests that a saccade may last from 20 ms to 100 ms. In some embodiments, the fixation may not be evaluated for a window of time within about 20 ms to about 100 ms of the change in color of the fixation stimulus, for example.

In some embodiments, the frequency reduction follows a predetermined or adaptive schedule based on cumulative fixation variance, number of completed entrainment cycles, or surgeon manual override. Alternatively or in combination, after N entrainment cycles, the system may transition to substantially continuous ON operation with micro-blanking intervals of ≤τ ms synchronized to the tracker latency. In some embodiments, τ comprises a period of the cadence of the fixation cycle.

Work in relation to the present disclosure suggests that human fixation stability improves with repetitive visual-motor entrainment; as the ON phase lengthens, the patient's neural suppression of saccades may become automatic. In some embodiments, the progressive shortening of OFF periods keeps attention active while reclaiming duty cycle for treatment, providing full-rate ablation once stability is established. In some embodiments, patients experience this as a "target that blinks slower and steadier" a natural sign of progress further reinforcing fixation behavior, for example.

Referring again to step 2060, in some embodiments, saccade-aware/responsive gating comprises a firing gate $G(t) \in \{0,1\}$. The firing gate may comprise a binary control signal that changes over time.

$$G(t) = 1: \text{the laser is allowed to fire.}$$

$$G(t) = 0: \text{the laser is turned off.}$$

In some embodiments, "Gating" means the laser output is conditionally enabled based on an eye state.

In some embodiments, Fixation-ON/Fixation-OFF comprises a binary output that is generated in response to eye position data.

Fixation-ON: the eye is stable and intentionally focused on a target.

Fixation-OFF: the eye is not stably fixating (e.g., during saccades or loss of attention).

In some embodiments, the fixation state is related to a chromatic cadence among colors, such as a cadence of green and red illumination as described herein. In some embodiments, the cadence refers to repeated timing of durations of each of a plurality of colors and the repeated timing of transitions between colors.

Referring again to step 2070, in some embodiments, $U_c(t)$ refers to the current eye position, such as one or more of a corneal, a pupil or a limbal eye position, for example. In some embodiments, a measured eye position vector at time t is determined at the location. In some embodiments, $\hat{U}_c(t-\tau)$ refers to a latency shifted estimate of the position of the eye. In some embodiments, this refers to a previous estimate of eye position from time $t-\tau$. In some embodiments the hat "^" refers to estimated or filtered values. In some embodiments, this term accounts for system latency related to a combination of camera acquisition time (e.g. at least one frame), processing time to determine the eye position, and time to move the actuator such as a scanning mirror as described herein.

In some embodiments, the latency τ refers to the end-to-end delay between when the eye moves and when the system can respond. In some embodiments, this includes sensing, computation, and beam steering delays.

In some embodiments, Norm $\| U_c(t) - \hat{U}_c(t-\tau) \|$ refers to the magnitude of the difference between two eye positions. In practice this may refer to "How far has the eye moved since the last usable estimate?", which may be a Euclidean distance.

In some embodiments, the threshold T refers to a tolerance limit (e.g., 10-20 μm at the cornea).

In some embodiments, if the eye has moved more than T, the movement is considered unacceptable or uncontrolled.

In some embodiments, this prevents firing during rapid eye motion.

In some embodiments, a saccade detector refers to a module that detects rapid eye movements. The saccade detector can be based on a velocity threshold (eye moving too fast), an acceleration threshold, or cadence disruption (e.g. a loss of rhythmic fixation signal), for example.

In some embodiments, when the saccade detector is triggered, it forces $G(t0=0$, for example immediately to 0.

In some embodiments, the position of the laser beam position, e.g. the laser beam path is frozen in response to a detected saccade. In some embodiments, the laser's aim or emission is held constant or disabled. For example, the position of the scanning mirror to deflect the beam may be fixed when a saccade has been detected.

In some embodiments, this inhibits chasing the eye during saccades.

In some embodiments, a predictor for residual latency is provided. In some embodiments, the predictor comprises a bounded predictor. In some embodiments, the predictor comprises a predictive model that 1) estimates where the eye will be after latency τ; and 2) is constrained so it does not extrapolate wildly. In some embodiments, "Bounded" means the that predictor refuses to follow fast or implausible motion (like saccades).

In some embodiments, the predictor for residual latency comprises an $\alpha$-$\beta$-$\gamma$ filter predictor. The $\alpha$-$\beta$-$\gamma$ filter predictor comprises a motion predictor using: $\alpha$: position correction, $\beta$: velocity correction, and $\gamma$: acceleration correction.

In some embodiments, this predictor is used for smooth, low-frequency motion such as head movement or fixation drift.

In some embodiments, the predictor for residual latency comprises a Kalman filter with anatomical priors. In some embodiments, this predictor comprises a probabilistic estimator combining: noisy measurements, a motion model, and prior knowledge about realistic eye behavior (e.g., max velocity).

In some embodiments, the prior knowledge comprises data related to prior eye movements and may be used as a constraint to decrease the likelihood of unrealistic predictions.

In some embodiments, $\tilde{U}_c(t+\tau)$ refers to a predicted future position, such as a forward-projected estimate of where the eye will be after latency. In some embodiments, the tilde "~" refers to the position as a predicted position, not a measured position.

In some embodiments, the beam command $B_c(t)$ refers to the commanded beam position sent to the laser steering system. In some embodiments, this comprises an offset of the eye position from the initial position combined an offset of the laser beam for a particular pulse of the laser system. In some embodiments, this is defined as: $B_c(t)=\tilde{U}_c(t+\tau)$. In some embodiments, this command is only issued when the gate is open ($G(t)=1$).

In some embodiments, the system is configured to handle drift while not chasing saccades, e.g. handle drift while refusing to chase saccades. In some embodiments, the slow eye drift is predicted and compensated as described herein, and fast movements are ignored because the gate closes, for example.

Referring again to step 2080, in some embodiments, the system is configured to lock into the umbo surrogate after the saccadic eye movement has stopped. In some embodiments, the system is configured to re-lock onto the umbo surrogate by using a reference position, such as a pupil position and offset of the treatment location relative to the pupil position. Alternatively or in combination, the system can be configured to re-establish the location umbo surrogate as described herein, for example with Vernier acuity, e.g. edge kiss symmetry, or by determining the 3D location of the first Purkinje image, for example.

In some embodiments, $S_c(t)$ refers to the saccade trajectory, which represents the path of the eye during a saccade. In some embodiments, this is explicitly not followed, because saccades are too fast and to track reliably.

In some embodiments, the system is configured to determine the location of the umbo surrogate with one or more of a parallax or Vernier acuity routine, for example.

In some embodiments, a high-precision reacquisition method uses symmetry or alignment cues as described herein, for example, such as edge-kiss symmetry to align visual features until symmetry is restored.

In some embodiments, the relocking step 2080 is used to re-establish accurate eye position after saccadic motion, for example.

Referring again to step 240, in some embodiments the pause ends and the treatment resumes when the gate is reopened. In some embodiments, $G(t)=1$ reenables laser firing. In some embodiments, this only happens when stability is confirmed again.

In some embodiments, the dwell time D refers to a minimum continuous stability period (e.g., 100-300 ms). In some embodiments, this may help to ensure stable fixation is stead and not transient and may help to decrease rapid flickering between ON/OFF states.

In some embodiments, the re-lock condition is defined as $\|U_c-\hat{U}_c\|\leq T$ for time D. In some embodiments, the eye must remain within the spatial threshold T continuously, for the full dwell time D. In some embodiments, only then is the system considered reliably re-locked.

At a step 2095 the treatment is completed.

At a step 2097 treatment statistic such as treatment metrics are generated. The statistics may comprise any suitable statistics, such as RMS movement of the eye, for example. In some embodiments, the statistics are related to the gating of the system and percentages of the time that the system is on. In some embodiments, a metric related to RMS error during the Fixation-ON configuration of the system. In some embodiments $RMS_{ON}$ is related to the error of the beam at the cornea and the umbo surrogate at the cornea during fixation on windows, e.g. $RMS_{ON}(B_c-U_c)$ in $\mu m$ at the cornea during Fixation-ON windows, for example.

In some embodiments, the treatment statistics comprises a saccade immunity metric, which is a fraction of pulses inhibited during saccades. Work in relation to the present disclosure suggests that this should ideally be ~100%.

In some embodiments, a recentering metric corresponds to a time-to-relock after a saccade. In some embodiments, the time to relock should be less than 300 ms.

Work in relation to the present disclosure suggests that it may be helpful to provide alignment errors in relation to error at the retina. Work in relation to the present disclosure suggests that the retinal mis-aim is ~3.1 time the corneal mis-aim. For example, a 10 $\mu m$ corneal error budget corresponds to ~31 $\mu m$ retinal tolerance at the umbo. In some embodiments, the tolerance for the alignment with the umbo surrogate at the cornea is within a range from 0-10 $\mu m$ to provide retinal placement within a range from 0-31 $\mu m$ at the retina, such as inside a $\pm 20$ $\mu m$ ultra-fidelity zone of an umbo, for example.

The steps of the method 2000 of controlling laser firing as shown in FIG. 20 can be modified in many ways and may provide improved accuracy.

In some embodiments, the fixation target comprise a cadence frequency: $f_c \approx 0.5$ Hz(period $T_c \approx 2$ s).

In some embodiments, the duty cycle is ON=1.2–1.6 s, and OFF=0.4–0.8 s. In some embodiments, the user interface is configured to allow the surgeon to adjust the duty cycle. In some embodiments, the duty cycle corresponds to a second light source overlaid on a first light source. For example the first light source may comprise a substantially continuous light source, e.g. a green light source, and the second light source may comprise the light source with duty cycle. IN some embodiments, the laser system comprises a user interface configured to allow the user such as a surgeon to adjust the duty cycle and choose a duty cycle that is appropriate for an individual patient.

In some embodiments, the processor is configured to provide blanking (i.e. safety) windows to cover lag and transients and decrease laser firing during saccades or other undesirable eye movement, for example.

In some embodiments, Pre-ON blank: $\tau$(e.g., 2 ms) before the red cue turns ON, inhibit pulses. In some embodiments, $\tau$ refers to the latency of the closed loop tracking system as described herein.

Post-ON verify dwell: require $\|B_c-U_c\|\leq T$ for D=100–300 ms before allowing pulses.

Pre-OFF blank: stop pulses τ before the red cue turns OFF (avoid catching a voluntary blink or impending micro-saccade).

In some embodiments, this approach provides benefits for the accuracy of the treatment provided. In some embodiments, the laser firing is decreased inside the controller's "blind spot", e.g. the crossing the ON/OFF boundary of the fixation color cycling during the cadence. In some embodiments, the laser only fires after a stable dwell inside the corneal tolerance window, e.g. less than 10 μm corneal tolerance window, or less than 20 μm corneal tolerance window. In some embodiments, the pulse cloud accumulates with a mean-zero value around the umbo proxy rather, than stepping with saccades and errors introduced by attempting to follow saccadic eye movement.

Although FIG. 20 shows a method 2000 of controlling laser firing in accordance with some embodiments, one of ordinary skill in the art will recognize many adaptations and variations as described herein. The steps can be performed in any order. Some of the steps can be repeated. Some of the steps can be omitted. Some of the steps may comprise sub steps of other steps, for example. In some embodiments, one or more steps of method 2000 are combined with one or more steps of another method as described herein, for example. Also, the processor can be configured to perform the step of any method or system function disclosed herein, such as any step of method 2000, for example.

FIGS. 21A to 21D shows a series of fixation stimuli as perceived by the patient.

Figures 21A, 21B, 21C, 21D:
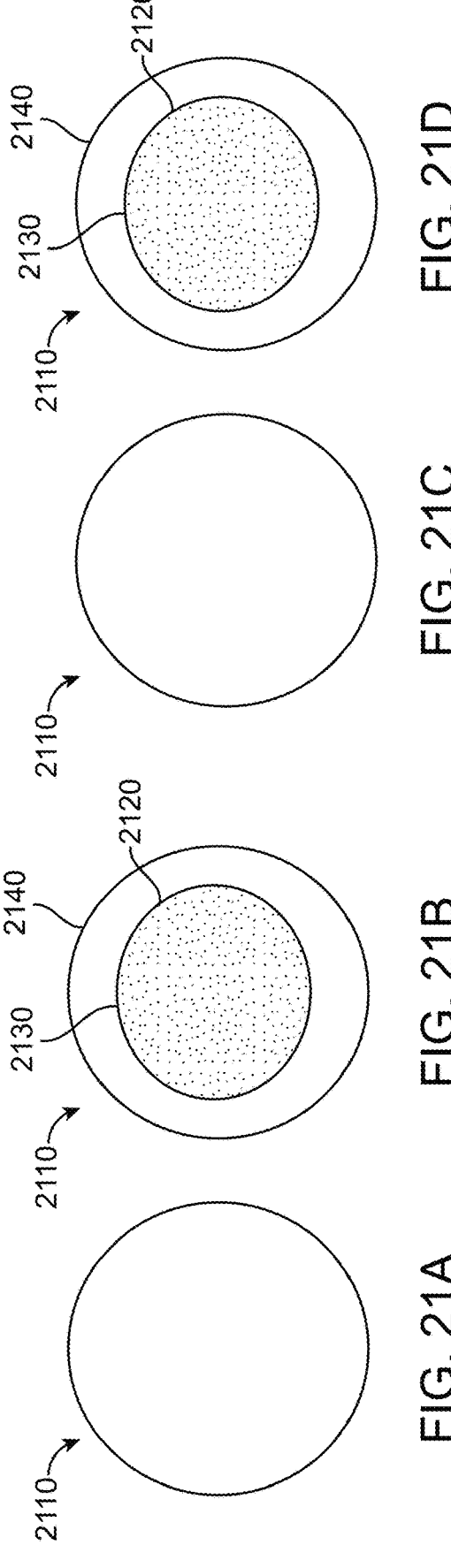
FIGS. 21A to 21D show a series of fixation stimuli, in accordance with some embodiments.

FIG. 21A shows a fixation stimulus during a time interval in which a first light beam 2110 is on and a second light beam 2120 is off. In some embodiments, the first light beam 2110 is substantially on for approximately 100% of the time for a series of cycles of the fixation stimulus, although the duty cycle may be lower as described herein.

FIG. 21B shows a fixation stimulus during a time interval in which a first light beam 2110 is on and a second light beam 2120 is on. The second light beam 2120 is shown within the first light beam 2110. Alternatively, the first light beam 2110 may be located within the second light beam 2120, for example. In some embodiments, a boundary 2130 of the second light beam 2120 extends around the second light beam so as to define a boundary between the first light beam and the second light beam. Although reference is made to first and second light beams, the first light beam and the second light beam may comprise a shared beam path, for example a shared beam path of light emitting diodes of a display.

FIG. 21C shows a fixation stimulus during a time interval in which a first light beam 2110 is on and a second light beam 2120 is off.

FIG. 21D shows a fixation stimulus during a time interval in which a first light beam 2110 is on and a second light beam 2120 is on.

In some embodiments, the duty cycle of the second beam can be varied while still maintaining spatial overlap. For example, the first overlapping beam configuration of FIG. 21B may comprise a first duty cycle, for example within a range from 30 percent to 70 percent, and the second overlapping beam configuration of FIG. 21D may comprise a second duty cycle within a range from 0.05% to 10% for example.

Work in relation to the present disclosure suggests that the variation of the color of the beam may be helpful in identifying the achromatic axis of the eye of the patient. In some embodiments, the umbo surrogate comprises the achromatic axis of the eye. In the overlapping configurations of FIGS. 21B and 21D, the second beam will appear symmetrically with respect to the first beam when the eye has been aligned on the achromatic axis. In some embodiments, when the eye has not been sufficiently aligned with respect to the achromatic axis, the first beam may not appear symmetrically with respect to the first beam and may shift in relation to the second beam for example, which may provide an indicator of alignment, for example when the patient confirms that the second beam does not move relative to the first beam.

Figure 22:
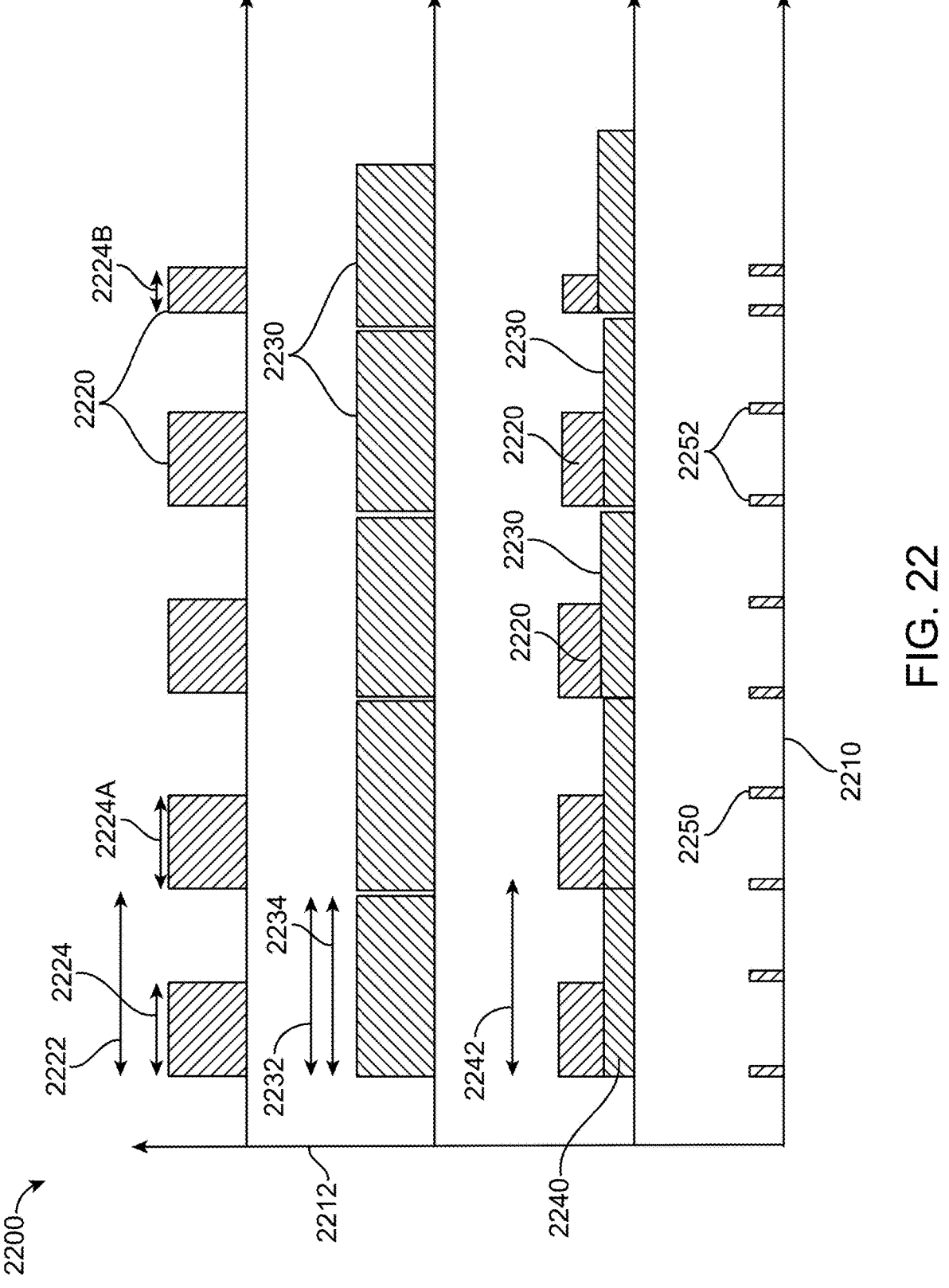
FIG. 22 shows chromatic cycling of a combined series of light pulses of different colors as seen by the patient.

FIG. 22 shows chromatic cycling 2200 of a combined series of light pulses 2240 of different colors of the fixation stimulus. The combined series of light pulses may comprise temporally and spatially overlapped light pulses, for example as shown with reference to FIG. 21. The combined stimulus 2240 may comprise a combined series of light pulses of one or more of the fixation beam or the aiming beam, for example. Alternatively, the series of light pulses may comprise a series of light pulses from a fixation stimulus such as a display or a polychromatic LED, for example. In some embodiments, the combined series of light pulses comprises light from the fixation beam combined with light from the aiming beam. Alternatively, the combined series of light pulses may comprise a series of light pulses from fixation light beam source comprising a display.

In some embodiments, the combined series of light pulses is configured to provide illumination of the retina with a duty cycle within a range from 75 percent to 100%, for example. In some embodiments, a first light source remains continuously illuminated while a second light sources turns on and off with a duty cycle, such as a variable duty cycle.

While the combined series of light pulses can be generated in many ways, the combined series of light pulses may comprise light from a first source such as the aiming beam and light from a second source such as fixation beam. Alternatively or in combination, the poly chromatic series of light pulses may comprise light pulses may comprise light pulses from a display, in which the display changes a color of light emitted from the display with a first color at a location on the display to a second color at the location of the display, and the location on the display remains substantially fixed for the first color and the second color, for each illumination cycle. In some embodiments, the series of light pulses is provided by a first beam with a first color and a second beam with a second color, in which the beam paths are combined with a beam splitter, for example. The beams may emit light in an interleaved manner along the beam paths, for example. In some embodiments, the series of pulses do not overlap temporally, such that only a single color is emitted at any time during the first and second series of pulses.

In some embodiments, a first series light pulses 2220 comprise light from a first source such as light from the aiming beam and a second series of light pulses 2230 comprise light from the fixation beam. In some embodiments, the processor is configured to turn the first light source and the second light source on and off at fixed intervals. In some embodiments, the fixation beam and the aiming beam are turned on and off at fixed intervals.

As shown in FIG. 22, the intensity 2212 of pulses 2220 of light from the first light source can be turned on and off with period 2222 with a duty cycle 2224 over time 2210. The intensity 2222 of pulses 2230 of light from the second light source such as the fixation beam can be turned on and off with period 2232 with a duty cycle 2234 over time 2210. In some embodiments, the duty cycle 2234 comprises approximately 100%, and the illumination may be substantially continuous.

The cycle of the combined fixation stimulus 2240 comprises a period 2242 for each cycle. The duty cycle 2224 can be varied to provide variable overlap in the illumination of the first light source and the second light source. The duty cycle 2224 can be varied to provide a varying fixation stimulus. In some embodiments, the duty cycle 2224 changes from a first duty cycle 2224A at a first time to a second duty cycle 2224B at a second time. In some embodiments, the duty cycle 2224 decreases in response to stabilized fixation of the eye, so as to provide feedback to the subject. In some embodiments, first light source and the second light source are configured to overlap temporally, to provide spatial overlap from the first optical path and the second optical path as described herein, for example.

Although reference is made to the first light source and the second light source comprising the aiming beam and the fixation beam, in some embodiments, the first light source may comprise a first light color emitted from a display and the second light source may comprise a second color emitted, from a display, for example with both emitted from substantially the same location of the display.

In some embodiments, a timing gate 2250 is associated with the timing of the changes in the color of the fixation stimulus. In some embodiments, the gate is configured to inhibit pulses of the laser beam during times 2252 associated with a change in the color of the stimulus. Alternatively or in combination, the gate 2250 may be configured to inhibit pulses during a time that the first light source is on, for example.

Figures 23A, 23B, 23C:
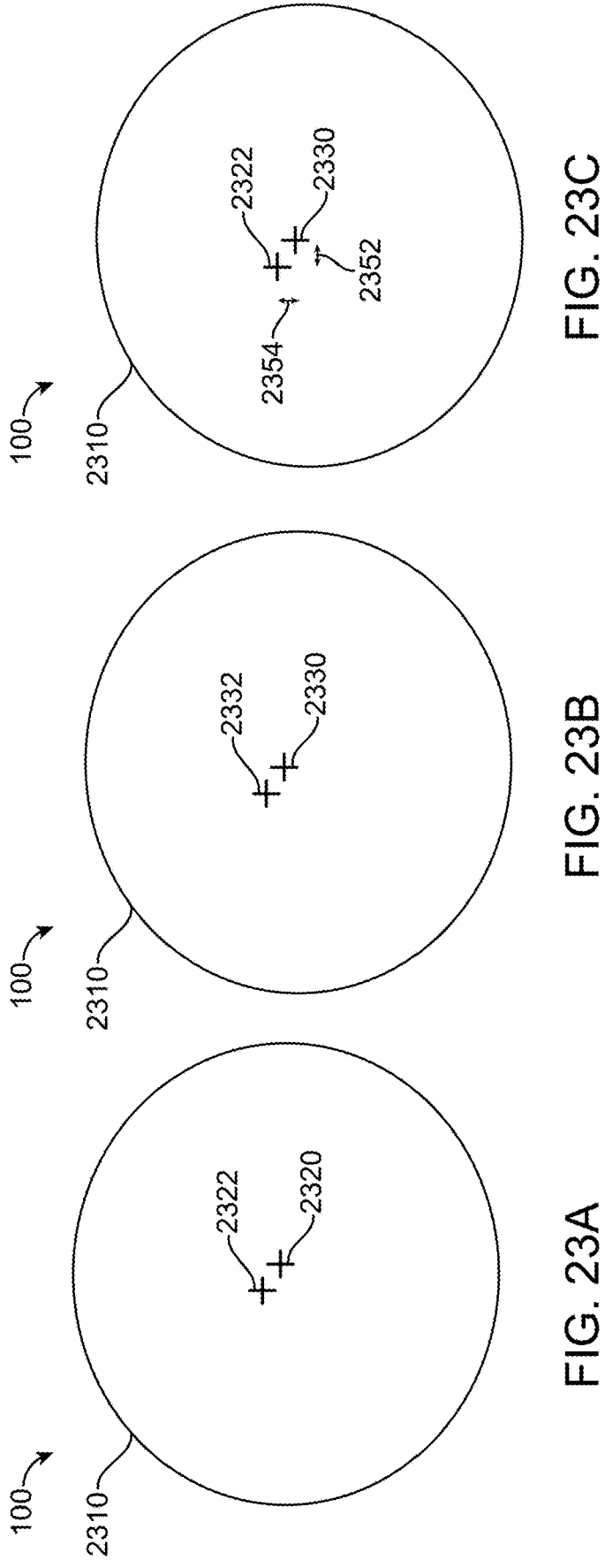
FIGS. 23A to 23C show illumination data used to determine the location of the umbo surrogate under mesopic or scotopic positions relative to the pupil center under photopic illumination.

FIGS. 23A to 23C show illumination data used to determine the location of the umbo surrogate under mesopic or scotopic positions relative to the pupil center under photopic illumination. This relative position can be programmed into the therapy device such as a laser system in order to center the therapy on the umbo surrogate.

FIG. 23A shows an eye 100 under mesopic or scotopic illumination, and a location of the pupil center 2320 and the umbo surrogate 2322 under mesopic or scotopic as described herein.

FIG. 23B shows an eye 100 under photopic illumination, and a location of the pupil center 2330 and the umbo surrogate 2332 under photopic illumination as described herein.

FIG. 23C shows an eye 100 under photopic illumination, and a location of the pupil center 2330 under photopic illumination and the umbo surrogate 2322 under mesopic or scotopic illumination relative to the pupil as described herein. The offset between the photopic pupil center 2330 and the mesopic or scotopic umbo surrogate 2322 may comprises delta X 2352 and delta Y 2354 coordinates, for example. Alternatively, the coordinates may comprise polar coordinates, for example. In some embodiments, the coordinates are provided with respect to the surface of the cornea.

While the offset between the mesopic or scotopic umbo surrogate 2322 and the photopic pupil can be determined in many ways, in some embodiments the offset is determined on a first device as described herein. In some embodiments, the offset determined on the first device is provided to the second therapy device, which receives the offset and centers the therapy on the scotopic or mesopic umbo surrogate location, which has been determined relative to the photopic pupil.

Although reference made to providing the offset of the umbo surrogate 2322 under mesopic or scotopic illumination relative to the photopic pupil 2330, in some embodiments the offset is provided to the therapy device in relation to the limbus 2310 or other suitable marker as described herein. In some embodiments, the location of the umbo surrogate 2322 under mesopic or scotopic illumination is determined in relation to the limbus 2310, and the location of the surrogate 2322 relative to limbus 2310 is provided to the therapy device while the eye is under photopic illumination.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

In some embodiments, the location of the umbo surrogate 2322 under mesopic or scotopic illumination is determined on a diagnostic device such as one or more of a wavefront system, a corneal topography system or an autorefractor. The treatment profile is determined in response to the location of the umbo surrogate 2322 and the data from the one or more of the of the wavefront system, the corneal topography system or the autorefractor. In some embodiments, the treatment profile is determined so as to be centered on the location umbo surrogate under mesopic or scotopic illumination, for example.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, firmware, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of" Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

As used herein, the terms proxy and surrogate are interchangeable.

The present disclosure includes the following numbered clauses.

1. A method of aligning an eye of a subject with an instrument, the method comprising: placing the subject on a support; directing a fixation beam toward an umbo of the eye, the fixation beam comprising a first color; instructing the subject to fixate on the fixation beam; directing an aiming beam to a cornea of the eye to a first location corresponding to a center of the pupil while the subject fixates on the fixation beam, the aiming beam comprising a second color different from the first color of the fixation beam; moving the aiming beam to a second location, the second location aligned with a reflection of the fixation beam, the second location different from the first location; and altering an illumination intensity of one or more of the first beam or the second beam to change a color perceived by the subject while the fixation beam is aligned with the aiming beam; and confirming that the instrument is aligned with the umbo by asking the subject to confirm that the first beam and the second beam appear at a same location when illumination intensity changes among the first beam with the first color and the second beam with the second color.

2. The method of clause 1, wherein the steps of altering and confirming are performed at least two times.

3. The method of any preceding clause, wherein the first color comprises red, blue, green or yellow and the second color comprises a different one of the red, blue, green or yellow.

4. The method of any preceding clause, wherein the aiming beam overlaps with the fixation beam and a region of overlap comprises intermittent or superimposed colors, and optionally a color intermediate to the first color or the second color.

5. The method of any preceding clause, wherein the region of overlap is located on the umbo and the subject perceives the intermittent or superimposed colors at the same location for the fixation beam and the aiming beam and optionally a color intermediate to the first color and the second color.

6. The method of any preceding clause, wherein the user perceives the intermittent or superimposed colors at the region of overlap from a microscope image and optionally perceives the intermediate color at the same location.

7. The method of any preceding clause, wherein the aiming beam is turned off while the fixation beam remains on to alter the illumination intensity of the one or more of the first beam or the second beam.

8. The method of any preceding clause, further comprising determining an amount of offset between the first location and the second location and optionally wherein the amount of offset comprises one or more of X, Y coordinates and or polar coordinates.

9. The method of any preceding clause, wherein the reflection of the fixation beam comprises a Purkinje image of the fixation beam.

10. The method of any preceding clause, wherein the aiming beam is substantially parallel to the fixation beam at the first location and the second location and optionally parallel to within about 0.5 degrees and optionally to within 0.1 degrees.

11. The method of any preceding clause, wherein the aiming beam is scanned from the first location to the second location with a lens and one or more mirrors in a telecentric configuration while the fixation beam remains fixed.

12. The method of any preceding clause, wherein aiming beam and the reflection of the fixation beam are viewed stereoscopically with a first optical path and a second optical path.

13. The method of any preceding clause, wherein the aiming beam and the reflection are viewed with alternating images from the first optical path and the second optical path.

14. The method of any preceding clause, wherein a surgeon views the Purkinje image along the first optical path with a first eye while the second optical path blocked and then views the Purkinje image along the second optical path with a second eye while the first optical path blocked.

15. The method of any preceding clause, wherein the reflection appears at as a Purkinje image at a first location relative to the aiming beam along the first optical path and at a second location relative to the aiming beam along the second optical path.

16. The method of any preceding clause, wherein the aiming beam is adjusted to appear between the first location of the Purkinje image and the second location of the Purkinje image.

17. The method of any preceding clause, wherein the aiming beam is adjusted to appear equidistant between the first location and the second location.

18. The method of any preceding clause, wherein the aiming beam is adjusted to a location between with first location and the second location of the Purkinje image with vernier acuity.

19. The method of any preceding clause, wherein, when the aiming beam is aligned with the reflection of the fixation beam, the aiming beam is located between the first location of the Purkinje image from the first optical path and the second location of the Purkinje image from the second optical path.

20. The method of any preceding clause, wherein a separation distance between the first location of the Purkinje image from the first optical path and the second location of the Purkinje image from the second optical path remains substantially fixed while the aiming beam is moved and brought into alignment.

21. The method of any preceding clause, wherein the separation distance is related to a distance between a first entrance pupil along the first optical path and a second entrance pupil along the second optical path, a curvature of the cornea, and a distance from one or more of the first entrance pupil or the second entrance pupil to the cornea.

22. A system to determine alignment an eye of a subject, the system comprising: a stereo microscope comprising an objective lens, a first ocular, a second ocular, a first parallax optical path to provide a first parallax image at the first ocular and a second parallax optical path to provide a second parallax image at the second ocular, the stereo microscope configured to image a cornea, an iris and a Purkinje image of the eye; an optical switch located along the first parallax optical path and the second parallax optical path to selectively block transmission of the first parallax image along the first optical path or the second parallax image along the second optical path; a fixation light source to generate a fixation beam to illuminate an umbo of the eye; a processor coupled to the optical switch to selectively provide the first parallax image to a first eye of a user or the second parallax image to a second eye to the user.

23. The system or method of any preceding clause, wherein a first two dimensional (2D) sensor array is coupled to the first optical path with a first beam splitter to capture the first parallax image and a second 2D sensor array is coupled to the optical path with a second beam splitter to capture the second parallax image of the eye.

24. The system or method of any preceding clause, wherein the first beam splitter is coupled to the first optical path between the objective lens and the optical switch to capture the first parallax image when the optical switch is closed along the first optical path, and wherein the second beam splitter is coupled to the second optical path between the objective lens and the optical switch to capture the second parallax image when the optical switch is closed along the second optical path.

25. The system or method of any preceding clause, wherein the processor is configured to generate a combined image from first parallax image data and second parallax image data.

26. The system or method of any preceding clause, wherein the combined image comprises a first Purkinje marker corresponding to a first location of the Purkinje image in the first parallax image and a second Purkinje marker corresponding to a second location of the Purkinje image in the second parallax image.

27. The system or method of any preceding clause, wherein combined image comprises a marker corresponding to a central location of the pupil and optionally wherein the central location comprises a centroid of the pupil.

28. The system or method of any preceding clause, wherein the combined image comprises the iris and the Purkinje image.

29. The system or method of any preceding clause, wherein the processor is configured to generate a real time video stream of combined images from the first parallax image data and the second parallax image data.

30. The system or method of any preceding clause, wherein the processor is coupled to a display to provide real time video stream on a display.

31. The system or method of any preceding clause, wherein the microscope is configured to image the cornea of the eye in focus, and the iris and the Purkinje image out of focus.

32. The system or method of any preceding clause, wherein the locations of the iris and the Purkinje image shift between the first parallax image and the second parallax image and a location of the cornea remains substantially fixed in the first parallax image and the second parallax image.

33. The system or method of any preceding clause, further comprising an aiming beam to focus a spot on a cornea of the eye, and wherein locations of the iris and the Purkinje image shift between the first parallax image and the second parallax image and locations of the spot in the first parallax image and the second parallax image remain substantially fixed.

34. The system or method of any preceding clause, wherein the processor is coupled to a mirror configured to move the focused spot into alignment with a first parallax image of the Purkinje image and a second parallax image of the Purkinje image.

35. The system or method of any preceding clause, wherein the fixation beam and the aiming beam overlap on an umbo of the eye when the aiming beam aligned with the fixation beam.

36. The system or method of any preceding clause, wherein the processor is configured to adjust an intensity of one or more of the aiming beam or the fixation beam to change a perceived color at a location of overlap on the umbo.

37. The system or method of any preceding clause, further comprising a first sensor array coupled to the first optical path to capture the first parallax image and a second sensor array coupled to the second optical path to capture the second parallax image.

38. The system or method of any preceding clause, wherein the processor is configured to generate a combined image from the first parallax image and the second parallax image.

39. The system or method of any preceding clause, wherein a location of an aiming beam focused on the cornea remains fixed in the combined image and the Purkinje image and the iris are offset in the first image relative and the second image relative to each other.

40. The system or method of any preceding clause, wherein the processor is configured to toggle between the first parallax image and the second parallax image with a frequency within a range from 0.5 Hz to 2 Hz.

41. The system or method of any preceding clause, wherein the processor is configured to toggle between the first parallax image and the second parallax image with a frequency less than a frequency of on and off cycles of the fixation beam.

42. The system or method of any preceding clause, wherein the processor is configured to change a color of the fixation beam from a first color to a second color different from the first color.

43. The system or method of any preceding clause, wherein the processor is configured to determine a location of a center of the pupil and optionally wherein the center of the pupil comprises a centroid of the pupil.

44. The system or method of any preceding clause, wherein the processor is configured to determine a distance from the center of the pupil to the Purkinje image and optionally wherein a location of the Purkinje image corresponds to a first location of the Purkinje image from the first parallax image and a second location of the Purkinje image from the second parallax image.

45. The system or method of any preceding clause, wherein the optical switch comprises one or more of a plurality of shutters, a rotating aperture wheel, an electronic shutter, an optoelectronic shutter, a liquid crystal shutter or an optoelectronic shutter.

46. The system or method of any preceding clause, wherein the processor is configured to triangulate a location of the Purkinje image in response to the first parallax image and the second parallax image.

47. The system or method of any preceding clause, wherein the processor is configured to triangulate a central location of the pupil in response to the first parallax image and the second parallax image.

48. The system or method of any preceding clause, wherein the processor is configured to triangulate a position of an aiming beam focused on a cornea in response to the first parallax image data and the second parallax image data.

49. A system to determine alignment of an eye of a subject, the system comprising: a light source configured to emit a fixation light beam toward an umbo of the eye along a fixation optical path; a parallax imaging system comprising a first parallax optical path and a second parallax optical path, the first parallax optical path on a first side of the fixation optical path to capture a first parallax image of the eye, the first parallax image comprising a pupil of the eye and a Purkinje image of the fixation light beam, the second parallax optical path located on a second side of the fixation optical path to capture a second parallax image of the eye, the second parallax image comprising the pupil and the Purkinje image; and a processor coupled to the parallax imaging system, the processor configured to determine a location of the Purkinje image in response to the first parallax image and the second parallax image.

50. The system or method of any preceding clause, wherein the processor is configured to output a point corresponding to a location of the Purkinje image and a second point corresponding to a location of a center of the pupil in response to the first parallax image and the second parallax image.

51. The system or method of any preceding clause, wherein the processor is configured to output a map comprising a first marker corresponding to the location of the Purkinje image and second marker corresponding to the location of a center of the pupil and optionally wherein map comprises a circular marker corresponding to a boundary between an iris and the pupil.

52. The system or method of any preceding clause, wherein the processor is configured to triangulate the location of the Purkinje image in response to a first location of the Purkinje image in the first parallax image and a second location of the Purkinje image in the second parallax image in order to determine the location of the Purkinje image.

53. The system or method of any preceding clause, wherein the processor is configured to triangulate the location of the pupil in response to a first location of the pupil in the first parallax image and a second location of the pupil in the second parallax image in order to determine the location of the pupil.

54. The system or method of any preceding clause, wherein the processor is configured to triangulate the Purkinje image in accordance with a triangle extending between a first entrance pupil of the first parallax optical path and a second entrance pupil of the second parallax imaging path, in which a vertex of the triangle corresponds to the location of the Purkinje image.

55. The system or method of any preceding clause, wherein the processor is configured to triangulate the pupil in accordance with a triangle extending between a first entrance pupil of the first parallax optical path and a second entrance pupil of the second parallax imaging path, in which a vertex of the triangle corresponds to the location of the pupil.

56. The system or method of any preceding clause, wherein the processor is configured to determine a location of the Purkinje image relative to a location of the pupil in response to the first parallax image and the second parallax image.

57. The system or method of any preceding clause, wherein the processor is configured to determine a first location of the Purkinje image relative to the pupil in the first parallax image and a second location of the Purkinje image relative to the pupil in the second parallax image and determine the location of the Purkinje image relative to the pupil in response to the first relative position and the second relative position.

58. The system or method of any preceding clause, wherein the processor is configured to determine a centroid of the Purkinje image and a centroid of the pupil in the first parallax image to determine the first location of the Purkinje image relative to the pupil and to determine a centroid of the Purkinje image and a centroid of the pupil in the second parallax image to determine the second location of the Purkinje image relative to the pupil.

59. The system or method of any preceding clause, wherein the processor is configured to determine the location of the Purkinje image in response to a first location of the Purkinje image in the first parallax image and a second location of the Purkinje image in the second parallax image.

60. The system or method of any preceding clause, wherein the first location corresponds to a first centroid of the Purkinje image in the first parallax image and the second location corresponds to a second centroid of the Purkinje image in the second parallax image.

61. The system or method of any preceding clause, wherein the processor is configured to determine the location of the pupil in response to a first location of the pupil in the first parallax image and a second location of the pupil in the second parallax image.

62. The system or method of any preceding clause, wherein the first location corresponds to a first centroid of the pupil in the first parallax image and the second location corresponds to a second centroid of the pupil in the second parallax image.

63. The system or method of any preceding clause, wherein the processor is configured to determine the location of the pupil and the Purkinje image in each of the first parallax image and the second parallax image with a trained Artificial Intelligence (AI) algorithm.

64. A system to determine alignment of an eye with an instrument, the system comprising: a fixation light source configured to emit a fixation light beam along a fixation optical path toward an umbo of the eye, the fixation light source configured to cycle between a first color and a second color at fixed time intervals; a microscope to image one or more of a pupil of the eye, an iris of the eye, or a Purkinje image of the light source; a processor coupled to the microscope to capture an image of the eye at each of a plurality of cycles of the fixation light source and to determine a location of the Purkinje image of the fixation light source at each of said plurality of intervals to determine a stability of fixation of the eye.

65. The system or method of any preceding clause, wherein the processor is configured to capture an image of the eye at each of the first color and the second color to determine a stability of fixation between the first color and the second color.

66. The system or method of any preceding clause, wherein the processor is configured to generate a sound at intervals corresponding to cycles of the light source, sound the perceptible to the subject.

67. The system or method of any preceding clause, wherein the processor is configured to determine an offset of the Purkinje image from a center of the pupil.

68. The system or method of any preceding clause, wherein the microscope comprises an objective lens coaxially aligned with a fixation light beam in a coaxially sighted corneal light reflex configuration.

69. The system or method of any preceding clause, wherein the microscope comprises a stereoscopic microscope.

70. A system to determine alignment with an eye of a subject, the system comprising: a fixation light source configured to emit a fixation light beam along a fixation optical path toward an umbo of the eye; a parallax imaging system comprising a first camera coupled to a first parallax optical path and a second camera coupled to a second parallax optical path, the first parallax optical path on a first side of the fixation optical path to capture a first parallax image of the eye comprising a pupil of the eye, and a first reflection of the fixation light beam at a first location, the second parallax optical path located on a second side of the fixation optical path to capture a second parallax image comprising the pupil, and a second reflection of the light beam at a second location; and a processor coupled to the parallax imaging system, the processor configured to generate a combined image comprising data from the first parallax image and the second parallax image, the combined image data comprising data related to the first reflection, the second reflection, and the pupil.

71. The system or method of any preceding clause, wherein the first camera comprises a first two dimensional sensor array coupled to a first beam splitter located along the first optical path and the second camera comprises a second two dimensional sensor array coupled to a second beam splitter along the second optical path and optionally wherein the first camera and the second camera are coupled to a stereoscopic microscope.

72. The system or method of any preceding clause, further comprising: an aiming beam configured to focus to a spot on a cornea of the eye; wherein the first parallax image comprises the aiming beam; wherein the second parallax image of the aiming beam; wherein the combined image comprises the aiming beam; and wherein the processor is configured to receive a user input to bring the focused spot into alignment between the first reflection and the second reflection of the combined image.

73. The system or method of any preceding clause, wherein the user input is configured to allow the user to adjust a location of the aiming beam in relation to the first reflection and the second reflection in the combined image.

74. The system or method of any preceding clause, wherein the processor is configured to determine a centroid of the pupil and position the aiming beam at a first location corresponding to the centroid of the pupil and receive the user input to place the aiming beam at a second location corresponding to alignment with the first reflection and the second reflection.

75. The system or method of any preceding clause, wherein the user interface is configured to allow the user to move the aiming beam into an aligned configuration in the combined image, the aligned configuration comprising the aiming beam being located along a line extending between the first reflection and the second reflection and substantially equidistant from the first reflection and the second reflection and optionally such that the first reflection and the second reflection are symmetrically disposed on either side of the aiming beam.

76. The system or method of any preceding clause, wherein a separation distance between the first reflection and the second reflection remains substantially fixed in the combined image in response to the user adjusting the location of the aiming beam.

77. The system or method of any preceding clause, wherein the first reflection and the second reflection appear tethered to each other with the substantially fixed separation distance in response to the aiming beam moving in the combined image.

78. The system or method of any preceding clause, wherein the separation distance remains substantially fixed to within about 10%.

79. The system or method of any preceding clause, wherein the separation distance corresponds to a distance between a first entrance pupil along the first optical path and a second entrance pupil along the second optical path.

80. The system or method of any preceding clause, wherein the first entrance pupil comprises one or more of a first entrance pupil of a first camera lens, a first entrance pupil of an objective lens, or a first entrance pupil of a first eye of a user and the second entrance pupil comprises one or more of a second entrance pupil of a second camera lens, a second entrance pupil of the objective lens, or a second entrance pupil of a second eye of the user.

81. The system or method of any preceding clause, wherein the second eye of the user comprises a contralateral eye of the user.

82. The system or method of any preceding clause, wherein in an aligned configuration, the aiming beam is located along a line extending between the first reflection and the second reflection.

83. The system or method of any preceding clause, wherein in an aligned configuration, the aiming beam is located substantially equidistant between the first reflection and the second reflection and optionally equidistant to about 10 percent (%).

84. The system or method of any preceding clause, wherein in an aligned configuration, the first reflection and the second reflection are located adjacent to the aiming beam in the combined image.

85. The system or method of any preceding clause, wherein the aiming beam overlaps with the first reflection and the second reflection in the combined image.

86. The system or method of any preceding clause, wherein a first gap extends between the first reflection and the aiming beam on a first side of the aiming beam and a second gap extends between the second reflection and the aiming beam on a second side of the aiming beam.

87. The system or method of any preceding clause, wherein a user interface is configured move the aiming beam along a line extending between the first reflection and the second reflection toward an aligned configuration.

88. The system or method of any preceding clause, wherein the user input is configured to allow a user to align the first reflection, the second reflection and the aiming beam with vernier acuity.

89. The system or method of any preceding clause, wherein the first reflection corresponds to a first location of a Purkinje image in the first parallax image and the second reflection corresponds to a second location of the Purkinje image in the second parallax image.

90. The system or method of any preceding clause, wherein the combined image data comprises data of the aiming beam, the first reflection, the second reflection and the pupil.

91. The system or method of any preceding clause, wherein first reflection and the second reflection comprise a first color and the aiming beam comprise a second color different from the first color.

92. The system or method of any preceding clause, wherein at an overlapping region of the aiming beam and one or more of the first reflection or the second reflection, the processor is configured to combine a luminance and a chrominance of the aiming beam and the one or more of the first reflection or the second reflection at the overlapping region.

93. The system or method of any preceding clause, wherein first color comprises one or more of red, orange, yellow, green, blue, indigo, or violet, and the second color comprises a different one of the one or more of red, orange, yellow, green, blue, indigo, or violet.

94. The system or method of any preceding clause, wherein first color comprises red, blue or green and the second color comprises a different one of the red, blue or green.

95. The system or method of any preceding clause, wherein the first color is configured to stimulate a first chromatic neural pathway of the user corresponding to the first color and the second color is configured to stimulate a second chromatic neural pathway of the user corresponding to the second color.

96. The system or method of any preceding clause, wherein the processor is configured to combine a chromatic luminance intensity of the first reflection marker or the second reflection marker with a chromatic luminance intensity of the aiming marker in response to an overlap.

97. The system or method of any preceding clause, wherein an overlapping region of the first reflection or the second reflection with the aiming beam comprises a composite color comprising the first color and the second color.

98. The system or method of any preceding clause, wherein the overlapping region comprises a combined luminance.

99. The system or method of any preceding clause, wherein the combined luminance at the overlapping region is greater than a luminance the aiming beam at the overlapping region, or a luminance of the first reflection or a luminance of the second reflection at the overlapping region.

100. The system or method of any preceding clause, wherein the processor is configured to generate a combined image comprising first and second overlapping regions, respectively, of the first reflection and the second reflection with the aiming beam.

101. The system or method of any preceding clause, wherein the first and second overlapping regions each comprises a composite color.

102. The system or method of any preceding clause, wherein the first and second overlapping regions each comprises a combined luminance.

103. The system or method of any preceding clause, wherein the processor is configured to display the reflection marker at a first location and a second reflection marker at a second location of the computer generated image with a variable offset from the one or more of the pupil or the aiming beam, and wherein the user input is configured to allow the user to place the aiming beam toward a line extending between the first location and the second location.

104. The system or method of any preceding clause, wherein the processor is configured to generate a combined image in response to the combined image data.

105. The system or method of any preceding clause, wherein the first reflection comprises a first computer generated marker and the second reflection comprises a second computer generated marker.

106. The system or method of any preceding clause, wherein a first reflection marker and a second location marker are located, respectively, at first and second locations of the computer generated image, the first and second locations of the computer generated image corresponding to the first location in the first parallax image and the second location in the second parallax image.

107. The system or method of any preceding clause, wherein the processor is configured to overlay the first parallax image on the second parallax image to generate the combined image.

108. The system or method of any preceding clause, wherein the processor is configured to register the first parallax image with the second parallax image to generate the combined image.

109. The system or method of any preceding clause, wherein the processor is configured to register the first parallax image with the second parallax image in response to a first location of a tissue structure in the first parallax image and a second location of the tissue structure in the second parallax image.

110. The system or method of any preceding clause, wherein the tissue structure comprises one or more of a pupil of the eye, an iris of the eye, blood vessels of the eye, a cornea of the eye or a Purkinje image of the eye.

111. The system or method of any preceding clause, wherein the processor is configured to determine a center of the pupil and display a marker corresponding to the center of the pupil in the combined image and optionally wherein the center of the pupil comprises a centroid of the pupil.

112. The system or method of any preceding clause, wherein the processor is configured to determine an offset between a center of the pupil and a reflection of the fixation target in each of the first parallax image and the second parallax image and optionally wherein the center of the pupil comprises a centroid of the pupil.

113. The system or method of any preceding clause, wherein the processor is configured to receive an input configured to move an alignment beam in four directions in relation to the display to perform alignment.

114. The system or method of any preceding clause, wherein the processor is configured to provide a user interface that includes a visual symmetry indicator displaying the first reflection of the fixation light beam and the second reflection of the fixation light beam in relation to an aiming beam focused on a cornea of the eye.

115. The system or method of any preceding clause, wherein a pair of "lock" events is recorded upon edge-kiss confirmation in two distinct cycles of the blinking fixation beam and an aiming beam, and wherein the system computes a mean of those coordinates as a final alignment location of the aiming beam.

116. The system or method of any preceding clause, wherein the processor is configured to provide a marker corresponding to a central location between the first reflection and the second reflection in response to the first parallax image and the second parallax image, wherein the marker indicates an inferred visual axis target corresponding to the umbo.

117. The system or method of any preceding clause, wherein the processor is configured to provide a white dashed ring indicating an inferred visual axis, in which a centration of the white dashed ring is based on a mean location of each of the first reflection and the second reflection and optionally wherein the mean location comprises one or more of an XY coordinate system or a radial coordinate system.

118. The system or method of any preceding clause, wherein a locations of the first reflection and the second reflection correspond to coaxially sighted corneal light reflex (CSCLR).

119. The system or method of any preceding clause, wherein the processor is configured to determine a first distance between the first reflection and an aiming beam and a second distance between the second reflection and the aiming beam.

120. The system or method of any preceding clause, wherein the processor is configured to adjust a position of the aiming beam in response to the first distance and the second distance.

121. The system or method of any preceding clause, wherein the processor is configured to place the alignment beam between the first reflection and the second reflection in the combined image.

122. The system or method of any preceding clause, wherein the processor is configured to direct an aiming beam toward a center of the pupil in response to the first parallax image and the second parallax image.

123. The system or method of any preceding clause, further comprising an aiming beam focused on a cornea of the eye, the aiming beam comprising a color different from a color of the fixation beam.

124. The system or method of any preceding clause, wherein the fixation beam comprises a first beam and the aiming beam.

125. The system or method of any preceding clause, wherein the processor is configured to adjust an intensity of one or more of the first beam or the aiming beam to adjust a color of the fixation beam.

126. The system or method of any preceding clause, wherein the fixation beam comprises a color intermediate to the first beam and the fixation beam during at least a portion of a cycle.

127. The system or method of any preceding clause, wherein the processor is configured to turn the aiming beam on and the fixation beam off during each of a plurality of cycles so as to provide an abrupt change in a color of the beam.

128. The system or method of any preceding clause, wherein the processor is configured to cycle one or more of the fixation beam or the alignment beam substantially on and substantially off at regular intervals to provide a perceived change in color of the fixation beam to the subject.

129. The system or method of any preceding clause, wherein the processor is configured to provide an audio cue to the subject, the audio cue corresponding to a change in perceived color of one or more of the fixation beam or the aiming beam.

130. The system or method of any preceding clause, wherein the alignment beam is substantially parallel with the fixation beam when aligned between the first reflection and the second reflection.

131. The system or method of any preceding clause, wherein the alignment beam appears at a location matching a perceived location of the fixation beam.

132. The system or method of any preceding clause, wherein the fixation beam comprises a laser beam and the alignment beam comprises a diode beam focused to a spot on a cornea.

133. The system or method of any preceding clause, wherein the fixation beam comprises a diode beam and the alignment beam comprises a diode beam focused to a spot on a cornea.

134. The system or method of any preceding clause, wherein the fixation beam comprises a laser beam and the alignment beam comprises a laser beam.

135. The system or method of any preceding clause, wherein the processor alternates between a first color of the fixation beam and a second color of the alignment beam to reduce fixation fatigue of the subject.

136. The system or method of any preceding clause, wherein a first color of the fixation beam corresponds to a fixation phase and a second color of the alignment beam corresponds to an alignment assessment phase.

137. The system or method of any preceding clause, wherein the processor is configured to cycle the fixation beam between a first color and a second color different from the first color at fixed intervals.

138. The system or method of any preceding clause, wherein the processor is configured to record the subject's fixation behavior during illumination with the first color and to move the aiming beam in response to a user input during illumination with the second color.

139. The system or method of any preceding clause, wherein a fixation beam comprises a target on a display at a substantially fixed location on the display and optionally wherein the target comprises a dot.

140. The system or method of any preceding clause, wherein the fixation beam alternates between the first color and the second color at a substantially fixed location.

141. The system or method of any preceding clause, wherein for each of a plurality of cycles, the processor is configured to provide a first color for a first duration and a second color for a second duration.

142. The system or method of any preceding clause, wherein the first color comprises one or more colors of a first color palette and the second color comprises one or more colors of a second color palette, the first color palette different from the second color palette.

143. The system or method of any preceding clause, wherein for each of the plurality of cycles the fixation target is dark after the second duration and prior to a first duration of a next cycle.

144. The system or method of any preceding clause, wherein for each of the plurality of cycles the fixation beam is dark between the first duration and the second duration.

145. The system or method of any preceding clause, wherein the first duration comprises no more than 0.5 seconds to 2 seconds and the second duration comprises no more than 0.5 seconds to 2 seconds for each of the plurality of cycles.

146. The system or method of any preceding clause, wherein a cycling of the fixation beam occurs at a frequency of 0.5 Hz or less with a first color, and wherein an alignment phase corresponding to a second color of the fixation beam is limited to no more than 2 seconds to reduce saccadic error.

147. The system or method of any preceding clause, wherein the processor is configured to provide an auditory instruction to the subject to fixate on the fixation target and optionally indicating that the fixation target is at a fixed location for the first color and the second color.

148. The system or method of any preceding clause, wherein the processor is configured to provide an auditory cue synchronized to a color change between the first color and the second color to reinforce fixation timing and reduce blink disruption.

149. The system or method of any preceding clause, wherein the processor is configured to record a series of eye positions during one or more of a first duration of illumination with the first color or a second duration of illumination with the second color over a plurality of illumination cycles.

150. The system or method of any preceding clause, wherein the processor is configured to determine a stability of fixation in response to the series of eye positions.

151. The system or method of any preceding clause, wherein the processor is configured to determine that the eye of the subject has locked onto the fixation beam in response to the series of eye positions recorded over the plurality of illumination cycles.

152. The system or method of any preceding clause, wherein the processor is configured to determine that the subject has locked onto the fixation beam in response to the series of eye positions over a plurality of illumination cycles corresponding to movement of the eye less than a threshold amount.

153. The system or method of any preceding clause, wherein the processor is configured to record a fixation locked in location of one or more of a fixation beam, or an aiming beam, in relation to a center of the pupil, in response to the series of eye positions over the series of illumination cycles less than the threshold amount.

154. A system to track movement of an eye of a subject, the system comprising: a fixation light source configured to emit a fixation light beam along a fixation optical path toward an umbo of the eye; a parallax imaging system comprising a first camera coupled to a first parallax optical path and a second camera coupled to a second parallax optical path, the first parallax optical path on a first side of the fixation optical path to capture a first parallax image of the eye comprising a pupil of the eye, and a first reflection of the fixation light beam at a first location, the second parallax optical path located on a second side of the fixation optical path to capture a second parallax image comprising the pupil, and a second reflection of the light beam at a second location; and a processor coupled to the parallax imaging system, the processor configured to track movement of the eye in response to the first parallax image and the second parallax image.

155. The system or method of any preceding clause, wherein the processor is configured to cycle the fixation beam between a first color and a second color different from the first color.

156. The system or method of any preceding clause, wherein the processor is configured to record a series of eye positions during one or more of a first duration of illumination with the first color or a second duration of illumination with the second color over a plurality of illumination cycles.

157. The system or method of any preceding clause, wherein the processor is configured to determine that the eye of the subject has locked onto the fixation beam in response to the series of eye positions recorded over the plurality of illumination cycles.

158. The system or method of any preceding clause, wherein the processor is configured to determine that the subject has locked onto the fixation beam in response to the series of eye positions over a plurality of illumination cycles corresponding to movement of the eye less than a threshold amount.

159. The system or method of any preceding clause, wherein the processor is configured to determine that the subject has locked onto the fixation beam with neuro visual fixation in response to a statistical significance of a plurality of eye movements and optionally in response to a p-value below a threshold amount.

160. The system or method of any preceding clause, wherein the processor is configured to output an offset of a location of the eye in real time in response tracked positions of the eye and optionally wherein the output is formatted for use with a laser treatment system.

161. The system or method of any preceding clause, wherein the first parallax optical path comprises a first portion of an objective lens of a microscope and the second parallax optical path comprises a second portion of the objective lens.

162. The system or method of any preceding clause, wherein the microscope comprises one or more of an operating microscope or a slit lamp.

163. The system or method of any preceding clause, wherein the first parallax optical path is separated from the second optical path by a distance.

164. The system or method of any preceding clause, wherein the separation distance corresponds to an interpupillary distance of a user of the system.

165. The system or method of any preceding clause, wherein the separation distance corresponds to a distance between a first lens of a first camera and a second lens of a second camera.

166. The system or method of any preceding clause, wherein the separation distance corresponds to a distance between a first entrance pupil of an objective lens along the first optical path and a second entrance pupil of the objective lens along the second optical path.

167. The system or method of any preceding clause, wherein the processor is configured to vary illumination of the eye and determine a diameter of the pupil and an offset of one or more of a Purkinje image or an aiming beam at each of a plurality of illumination intensities in response to one or more of photopic, mesopic or scotopic illumination.

168. The system or method of any preceding clause, wherein the processor is configured to output a data file comprising the diameter and offset at each of the plurality of illumination intensities.

169. The system or method of any preceding clause, wherein the processor is configured to acquire alignment data at each of the plurality of illumination conditions.

170. The system or method of any preceding clause, wherein the processor is configured to determine an offset of the one or more of the Purkinje image or the aiming beam with mesopic illumination and photopic illumination.

171. The system or method of any preceding clause, wherein the processor is configured to output a data file corresponding to a difference between a mesopic location of the one or more of Purkinje image or the aiming beam under mesopic illumination and a photopic location of the one or more of the Purkinje image or the aiming beam under photopic illumination, in order to center an optical therapy on the mesopic location of the one or more of the Purkinje image or the aiming beam under mesopic illumination when the eye is aligned to the photopic location under photopic illumination.

172. The system or method of any preceding clause, wherein the processor is configured to determine a torsional angle of the eye with respect to an optical axis of the eye in response to an image of the iris, the image of the iris comprising one or more of the first parallax image, the second parallax image, the combined image, or an image from a coaxially aligned camera.

173. The system or method of any preceding clause, wherein the processor is configured to measure the torsional angle and record whether the patient is seated or supine when the torsional angle has been measured.

174. The system or method of any preceding clause, wherein the processor is configured to determine an offset of the torsional angle between seated and supine positions of the subject.

175. The system or method of any preceding clause, wherein the processor is configured to output an offset of the torsional angle between seated and supine positions of the subject to a data file.

176. The system or method of any preceding clause, wherein the first optical path and the second optical path are configured to focus at a common plane of the eye.

177. The system or method of any preceding clause, wherein the common plane is located away from a first Purkinje image.

178. The system or method of any preceding clause, wherein the common plane is located on a cornea of the eye.

179. The system or method of any preceding clause, wherein the common plane is located on a virtual image of the iris corresponding to an entrance pupil of the eye.

180. The system or method of any preceding clause, wherein the processor comprises a cyclotorsion postural compensation module configured to adjust for cyclotorsion variation between seated and supine positions.

181. The system or method of any preceding clause, wherein the processor is configured to output alignment data comprising one or more posture tags, cyclotorsional tags or lighting tags corresponding to a recorded fixation state.

182. The system or method of any preceding clause, wherein separate alignment data is captured under photopic, mesopic, and scotopic conditions, and wherein cyclotorsion coordinates are adjusted in response to an illumination-dependent astigmatic or iris structure shift.

183. The system or method of any preceding clause, wherein a change in cyclotorsion rotation of the eye is determined in response to alignment of a first image of an iris structure and a second image of the iris structure, the first image acquired before postural adjustment, the second image acquired after postural adjustment.

184. The system or method of any preceding clause, wherein the processor is configured to determine the change in cyclotorsion rotation in response to a rotational alignment between iris structure in a first image and the iris structure in a second image.

185. The system or method of any preceding clause, wherein the aiming beam comprises an aiming beam of a laser treatment system.

186. The system or method any preceding clause, wherein the system is configured to align an optical therapy such as a treatment with an umbo of the eye.

187. The system or method of any preceding clause, wherein an alignment precision is confirmed to be within one or more of ±100 microns, +50 microns, +20 microns or +10 microns and optionally confirmed with an input from a user.

188. The system or method of any preceding clause, wherein alignment coordinates are configured to be transmitted to a treatment device or optical platform.

189. The system or method of any preceding clause, wherein output umbo location data is configured to be provided to one or more of an optical system, a targeting system, a ranging system, a scopes, a weapon sighting system, a magnified sighting system, binoculars, binocular sighting systems, a binocular targeting system, a lens, a microscope, a stereo microscope, a radiation therapy device, a robotic surgery system, a laser vision correction (LVC) system, a femtosecond laser system, an excimer laser system, a lens manufacturing system, a lens, an intraocular lens (IOL) manufacturing system, an intraocular lens, an intraocular lens planning system, a contact lens manufacturing system, a contact lens planning system, a contact lens (CL), a scleral contact lens, a rigid gas permeable (RGP) lens, a soft contact CL, a hybrid RGP/soft CL, a hydrogel CL, a stabilized CL, an intraocular lenses (IOL), an intracorneal lens (ICL), a spectacle manufacturing system, a spectacle, a visual aid, or a visual appliance, in order to provide an umbo-centered optical treatment.

190. The system or method of any preceding clause, further comprising a posture-dependent centroid compensation module configured to measure and correct for translational shift in pupil centroid between diagnostic and treatment positions.

191. The system or method of any preceding clause, wherein the alignment data is stored in association with the subject's pupil diameter and lighting condition during each recording cycle.

192. The system or method of any preceding clause, wherein the processor is configured to output data comprising a plurality of pupil diameters at a plurality of illumination intensities, and a plurality of alignment marker locations referenced to a pupil center at each of the plurality of illumination intensities.

193. The system or method of any preceding clause, wherein a display comprises one or more of a computer display, a heads up display, an augmented reality display, virtual reality display, a stand-alone display, or a touch screen display configured to receive a user input.

194. The system or method of any preceding clause, further comprising a laser treatment system, wherein the laser treatment system is configured to treat at only one of a plurality of colors of a fixation beam.

195. The system or method of any preceding clause, wherein a user interface comprises an input configured to allow the user to adjust one or more of a color, a timing, a duration of a cycle, or a gap of illumination of one or more light sources of the stimulus presented to the subject over a plurality of illumination cycles.

196. A method of treating an eye of a subject with a laser, the method comprising:

providing a variable color fixation stimulus to the subject, the variable color fixation stimulus comprising a first color at a first time and a second color at a second time; and aligning the eye with the laser.

197. The method of clause 196, wherein the variable color fixation stimulus transitions from the first color to the second color with a frequency.

198. The method of clause 197, wherein the first color comprises a first duty cycle and the second color comprises a second duty cycle and wherein one or more of the first duty cycle or the second duty cycle varies.

199. The method of clause 198, wherein the first duty cycle remains substantially fixed and the second duty cycle decreases and optionally wherein the first duty cycle remains substantially fixed at 100% and the second duty cycle varies to less than 50%.

200. The method of clause 199, wherein the second color is superimposed on the first color.

201. The method of clause 197, wherein the frequency comprises a frequency of a chromatic cadence.

202. The method of clause 197, wherein the frequency comprises a variable frequency.

203. The method of clause 202, wherein the variable frequency comprises a first frequency at a first time and a second frequency at a second time, the second frequency slower than the first frequency.

204. The method of clause 196, wherein a stability of fixation of the eye is evaluated while the variable color fixation stimulus is provided to the eye.

205. The method of clause 204, wherein the stability of fixation of the is evaluated in response to the change in the color of the fixation stimulus for each of a plurality of cycles of the color of the fixation stimulus.

206. The method of clause 204, wherein the stability of fixation of the eye does not include eye movement data for a period of time after a change in the color of the fixation stimulus.

207. The method of clause 204, wherein the stability of fixation the eye is used to determine a tolerance of eye movement of a gate.

208. The method of clause 196, wherein the second stimulus appears inside the first stimulus.

209. The method of clause 196, wherein the variable color fixation stimulus is aligned with an achromatic axis of the eye.

210. The method of clause 196, wherein the variable color fixation stimulus is focused to a spot on the cornea to increase a depth of field of the variable color fixation stimulus.

211. The method of clause 196, wherein a center of a treatment profile of the laser is aligned with a location of an umbo surrogate in response to the location of a center of a pupil.

212. The method of clause 211, wherein the location of the umbo surrogate in relation to the center of the pupil has been provided by a separate diagnostic instrument.

213. The method of clause 196, wherein a location of an umbo surrogate is determined in relation to a center of a pupil and a center of a treatment profile of the laser is aligned with the location of the umbo surrogate in response to the location of the center of the pupil.

214. The method of clause 196, wherein a location of an umbo surrogate under mesopic illumination is determined in relation to a center of a pupil under photopic illumination and a center of a treatment profile of the laser is aligned with the location of the umbo surrogate under scotopic or mesopic illumination in response to a center of a pupil under photopic illumination.

215. The method of clause 196, wherein a patient interface of a femtosecond laser engages the eye.

216. The method of clause 215, wherein the interface of the femtosecond laser engages the eye in response to stability of the eye within a threshold amount.

217. A method of treating an eye with a laser, the method comprising:

measuring a position of the eye;

evaluating a firing gate of the laser in response to the position of the eye, wherein the gate is configured to inhibit firing of the laser in response to a saccade and to allow the laser to treat the eye in response to an absence of a detected saccade.

218. The method of clause 217, wherein a variable color fixation stimulus is provided to the eye.

219. The method of clause 218, wherein the gate is configured to inhibit firing associated with a change in color of the fixation stimulus.

220. The method of clause 218, wherein the gate is configured to inhibit firing of the laser for a period of time after a change in the color of the fixation stimulus.

221. The method of clause 217, wherein a fixation of the eye is evaluated and the gate is configured to allow treatment in response to eye movement below a threshold amount and to inhibit treatment in response to eye movement above a threshold value.

222. The method of clause 221, wherein the threshold value is determined in response to eye movement data of the eye during a fixation evaluation prior to firing the laser.

223. The method of clause 217, wherein a future position of the eye is predicted in the response to the position of the eye, and a position of the laser treatment is adjusted in response to the predicted future position.

224. The method of clause 223, wherein a closed loop eye tracking system has a latency and the future position is predicted in response to the position of the eye and the latency.

225. The method of clause 217, wherein a scanner is configured to offset the laser beam in response to movement of the eye in response to the absence of a saccade.

226. The method of clause 225, wherein the scanner is configured to maintain a position of the scanner in response to a detected saccade.

227. The method of clause 217, wherein a laser treatment profile is centered on an umbo surrogate prior to the gate inhibiting firing of the laser and wherein the laser system is realigned with the umbo surrogate after the gate inhibits firing of the laser.

228. The system or method of any preceding clause, further comprising:

determining a location of a cornea or a lens of the eye corresponding to a location of an umbo of the eye; and placing the optical therapy at the location of the cornea or the lens of the eye corresponding to the location of the umbo.

229. The system or method of any preceding clause, wherein a location of a center of treatment on the cornea has been chosen to place a central effect of the treatment on the umbo of the eye.

230. A computer readable medium, which when executed by a processor, is configured to perform the method of any preceding clause.

231. A system for treating an eye of a subject with a laser, the system comprising:

a laser to treat the eye; and a processor configured to perform the method of any preceding clause.

232. The system or method of any preceding clause wherein an optical therapy is aligned with an achromatic axis of the umbo of the eye and optionally wherein the optical therapy comprises a laser treatment profile aligned with the achromatic axis of the umbo of the eye.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A method of treating an eye of a subject with a laser, the method comprising:

providing a variable color fixation stimulus to the subject, the variable color fixation stimulus comprising a first color at a first time and a second color at a second time; and aligning the eye with the laser;

wherein a stability of fixation of the eye is evaluated while the variable color fixation stimulus is provided to the eye;

wherein the stability of fixation the eye is used to determine a tolerance of eye movement of a gate.

2. The method of claim 1, wherein the variable color fixation stimulus transitions from the first color to the second color with a frequency.

3. The method of claim 2, wherein the first color comprises a first duty cycle and the second color comprises a second duty cycle and wherein one or more of the first duty cycle or the second duty cycle varies.

4. The method of claim 3, wherein the first duty cycle remains substantially fixed and the second duty cycle decreases and optionally wherein the first duty cycle remains substantially fixed at 100% and the second duty cycle varies to less than 50%.

5. The method of claim 4, wherein the second color is superimposed on the first color.

6. The method of claim 2, wherein the frequency comprises a frequency of a chromatic cadence.

7. The method of claim 2, wherein the frequency comprises a variable frequency.

8. The method of claim 7, wherein the variable frequency comprises a first frequency at a first time and a second frequency at a second time, the second frequency slower than the first frequency.

9. The method of claim 1, wherein the stability of fixation of the eye is evaluated in response to a change in the color of the variable color fixation stimulus for each of a plurality of cycles of the color of the fixation stimulus.

10. The method of claim 1, wherein the stability of fixation of the eye does not include eye movement data for a period of time after a change in the color of the variable color fixation stimulus.

11. The method of claim 1, wherein a second stimulus appears inside a first stimulus.

12. The method of claim 1, wherein the variable color fixation stimulus is aligned with an achromatic axis of the eye.

13. The method of claim 1, wherein the variable color fixation stimulus is focused to a spot on a cornea to increase a depth of field of the variable color fixation stimulus.

14. The method of claim 1, wherein a center of a treatment profile of the laser is aligned with a location of an umbo surrogate in response to the location of a center of a pupil.

15. The method of claim 14, wherein the location of the umbo surrogate in relation to the center of the pupil has been provided by a separate diagnostic instrument.

16. The method of claim 1, wherein a location of an umbo surrogate is determined in relation to a center of a pupil and a center of a treatment profile of the laser is aligned with the location of the umbo surrogate in response to the location of the center of the pupil.

17. The method of claim 1, wherein a patient interface of a femtosecond laser engages the eye.

18. A method of treating an eye of a subject with a laser, the method comprising:

providing a variable color fixation stimulus to the subject, the variable color fixation stimulus comprising a first color at a first time and a second color at a second time; and aligning the eve with the laser;

wherein a location of an umbo surrogate under scotopic or mesopic illumination is determined in relation to a center of a pupil under photopic illumination and a center of a treatment profile of the laser is aligned with the location of the umbo surrogate under scotopic or mesopic illumination in response to the center of the pupil under photopic illumination.

* * * * *